US009334275B2

(12) United States Patent
Yoshikai et al.

(10) Patent No.: US 9,334,275 B2
(45) Date of Patent: May 10, 2016

(54) PROCESSES FOR PREPARING INDOLES

(71) Applicant: Nanyang Technological University, Singapore (SG)

(72) Inventors: Naohiko Yoshikai, Singapore (SG); Ye Wei, Singapore (SG)

(73) Assignee: NANYANG TECHNOLOGICAL UNIVERSITY, Singapore (SG)

(*) Notice: Subject to any disclaimer, the term of this patent is extended or adjusted under 35 U.S.C. 154(b) by 0 days.

(21) Appl. No.: 14/360,250

(22) PCT Filed: Dec. 19, 2012

(86) PCT No.: PCT/SG2012/000481
§ 371 (c)(1),
(2) Date: May 22, 2014

(87) PCT Pub. No.: WO2013/095304
PCT Pub. Date: Jun. 27, 2013

(65) Prior Publication Data
US 2015/0005494 A1 Jan. 1, 2015

Related U.S. Application Data

(60) Provisional application No. 61/577,528, filed on Dec. 19, 2011.

(51) Int. Cl.
*C07D 209/04* (2006.01)
*C07D 487/04* (2006.01)
*C07D 401/04* (2006.01)
*C07D 405/04* (2006.01)
*C07D 209/08* (2006.01)
*C07D 209/12* (2006.01)
*C07D 209/18* (2006.01)
*C07D 209/42* (2006.01)
*C07D 209/60* (2006.01)
*C07D 209/10* (2006.01)

(52) U.S. Cl.
CPC .......... *C07D 487/04* (2013.01); *C07D 209/08* (2013.01); *C07D 209/10* (2013.01); *C07D 209/12* (2013.01); *C07D 209/18* (2013.01); *C07D 209/42* (2013.01); *C07D 209/60* (2013.01); *C07D 401/04* (2013.01); *C07D 405/04* (2013.01)

(58) Field of Classification Search
CPC .. C07D 209/08; C07D 209/12; C07D 209/14; C07D 209/42; C07D 471/04
USPC .......................................... 548/469; 544/144
See application file for complete search history.

(56) References Cited

U.S. PATENT DOCUMENTS 5,811,551 A    9/1998    Chen et al.

FOREIGN PATENT DOCUMENTS

GB    2 316 404 A        2/1998
GB    2316404 A    *    2/1998    ........... C07C 229/30

OTHER PUBLICATIONS

Shi, Z., C. Zhang, S. Li, D. Pan, S. Ding, Y. Cui, and N. Jiao. "Indoles from Simple Anilines and Alkynes: Palladium-Catalyzed C—H Activation Using Dioxygen as the Oxidant", Angewandte Chemie International Edition (2009), 48, pp. 4572-4576.*
Ackermann et al., "TiCl$_4$/t-BuNH$_2$ as the sole catalyst for a hydroamination-based Fischer indole synthesis," *Tetrahedron Letters* 45:9541-9544, 2004.
Ackland et al., "Conversion of (2-methyl-1-azabuta-1,3-diene)tricarbonyliron(0) complexes into (enamine)tricarbonyliron(0) complexes," *J. Chem. Soc., Perkin Trans. 1*:813-817, 1998.
Alex et al., "Zinc-Promoted Hydrohydrazination of Terminal Alkynes: An Efficient Domino Synthesis of Indoles," *Angew. Chem. Int. Ed.* 47:2304-2307, 2008.
Barluenga et al., "Modular Synthesis of Indoles from Imines and o-Dihaloarenes or o-Chlorosulfonates by a Pd-Catalyzed Cascade Process," *J. Am. Chem. Soc. 131*:4031-4041, 2009.
Bartoli et al., "A New Approach to the Synthesis of 2-Substituted Indoles: Reaction of Dimetallated Ortho-Trimethylsilylmethylanilides with Esters," *Tetrahedron 46*(4):1379-1384, 1990.
Bernini et al., "Copper-Catalyzed C—C Bond Formation through C—H Functionalization: Synthesis of Multisubstituted Indoles from N-Aryl Enaminones," *Angew. Chem. Int. Ed.* 48:8078-8081, 2009.
Cacchi et al., "Synthesis and Functionalization of Indoles Through Palladium-catalyzed Reactions," *Chem. Rev. 105*:2873-2920, 2005.
Cao et al., "Intermolecular Alkyne Hydroaminations Involving 1,1-Disubstituted Hydrazines," *Organic Letters 4*(17):2853-2856, 2002.
Chen et al., "Synthesis of Indoles via a Palladium-Catalyzed Annulation between Iodoanilines and Ketones," *J. Org. Chem.* 62:2676-2677, 1997.
Chen et al., "Palladium-Catalyzed Synthesis of 2-Fluoroalkyl-3-methylene-3H-indoles Through a Domino Carbopalladation/C—H Activation Process," *Adv. Synth. Catal.* 353:325-330, 2011.
Deprez et al., "Room Temperature Palladium-Catalyzed 2-Arylation of Indoles," *J. Am. Chem. Soc.* 128:4972-4973, 2006.
Desmarets et al., "Facile Synthesis and Characterization of Naphthidines as a New Class of Highly Nonplanar Electron Donors Giving Robust Radical Cations," *J. Org. Chem.* 71:1351-1361, 2006.
Du et al., "Electrosynthesis of Substituted 1H-Indoles from o-Nitrostyrenes," *Organic Letters 13*(15):4072-4075, 2011.
Gamble et al., "Synthesis of reaction-ready 6,6'-biindole and 6,6'-biisatin via palladium(II)-catalysed intramolecular C—H functionalisation," *Chem. Commun.* 46:4076-4078, 2010.
Gao et al., "Cobalt-Phenanthroline Catalysts for the *ortho* Alkylation of Aromatic Imines under Mild Reaction Conditions," *Angew. Chem. Int. Ed.* 50:6888-6892, 2011.

(Continued)

*Primary Examiner* — Nyeemah A. Grazier
*Assistant Examiner* — Sagar Patel
(74) *Attorney, Agent, or Firm* — Seed IP Law Group PLLC

(57) ABSTRACT

Methods for the synthesis of an indole in provided. Methods comprise oxidizing a N-aryl imine in the presence of a palladium-based catalyst, an oxidant, and a solvent.

20 Claims, 3 Drawing Sheets

(56) References Cited

OTHER PUBLICATIONS

Gautier et al., "Asymmetric reduction of ketimines with trichlorosilane employing an imidazole derived organocatalyst," *Org. Biomol. Chem.* 7:229-231, 2009.

Geary et al., "Modular Construction of 2-Substituted Benzo[b]furans from 1,2-Dichlorovinyl Ethers," *Organic Letters* 11(23):5478-5481, 2009.

Gribble, "Recent developments in indole ring synthesis—methodology and applications," *J. Chem. Soc., Perkin Trans. 1*:1045-1075, 2000.

Guan et al., "Preparation of indoles via iron catalyzed direct oxidative coupling," *Chem. Commun.* 46:2823-2825, 2010.

Han et al., "Spiro[4,4]-1,6-nonadiene-Based Phosphine-Oxazoline Ligands for Iridium-Catalyzed Enantioselective Hydrogenation of Ketimines," *Angew. Chem. Int. Ed.* 48:5345-5349, 2009.

Hughes, "Progress in the Fischer Indole Reaction, A Review," *Organic Preparations and Procedures Int.* 25(6):607-632, 1993.

Humphrey et al., "Practical Methodologies for the Synthesis of Indoles," *Chem. Rev.* 106:2875-2911, 2006.

Imamoto et al., "Enantioselective Hydrogenation of Acyclic Aromatic N-Aryl Imines Catalyzed by an Iradium Complex of (S,S)-1,2-Bis(tert-butylmethylphosphino)ethane," *Organic Letters* 8(11):2289-2292, 2006.

Jin et al., "Well-defined NHC—Pd complex-mediated intermolecular direct annulations for synthesis of functionalized indoles (NHC=N-hetero-cyclic carbene)," *Appl. Organometal. Chem.* 25:502-507, 2011.

Kasaya et al., "Aromatic Enamide/Ene Metathesis toward Substituted Indoles and Its Application to the Synthesis of Indomethacins," *Eur. J. Org. Chem.*:4606-4613, 2009.

Kino et al., "Pd-catalyzed coupling of arylamines and 2-bromo-3,3,3-trifluoropropene," *Journal of Molecular Catalysis A: Chemical* 282:34-51, 2008.

Kutlescha et al., "The potassium hydride mediated trimerization of imines," *Chem. Commun.* 47:4183-4185, 2011.

Lai et al., "Intra- and Intermolecular Hydroamination of Alkynes Catalyzed by ortho-Metalated Iridium Complexes," *Organometallics* 26:1062-1068, 2007.

Larock et al., "Synthesis of Indoles via Palladium-Catalyzed Heteroannulation of Internal Alkynes," *J. Am. Chem. Soc.* 113:6689-6690, 1991.

Lee et al., "Cobalt-Catalyzed, Room-Temperature Addition of Aromatic Imines to Alkynes via Directed C—H Bond Activation," *J. Am. Chem. Soc.* 133:17283-17295, 2011.

Liu et al., "Synthesis of Substituted 1,2-Dihydroquinolines and Quinolines from Aromatic Amines and Alkynes by Gold(I)-Catalyzed Tandem Hydroamination-Hydroarylation under Microwave-Assisted Conditions," *Organic Letters* 9(14):2645-2648, 2007.

Malkov et al., "Asymmetric Reduction of Imines with Trichlorosilane, Catalyzed by Sigamide, an Amino Acid-Derived Formamide: Scope and Limitations," *J. Org. Chem.* 74:5839-5849, 2009.

Moessner et al., "Diphenylphosphanylsulfoximines as Ligands in Iridium-Catalyzed Asymmetric Imine Hydrogenations," *Angew. Chem. Int. Ed.* 44:7564-7567, 2005.

Mršić et al., "Iridium/Monodentate Phosphoramidite Catalyzed Asymmetric Hydrogenation of N-Aryl Imines," *J. Am. Chem. Soc.* 131:8358-8359, 2009.

Nazaré et al., "A Flexible, Palladium-Catalyzed Indole and Azaindole Synthesis by Direct Annulation of Chloroanilines and Chloroaminopyridines with Ketones," *Angew. Chem. Int. Ed.* 43:4526-4528, 2004.

Neumann et al., "Exploring the Oxidative Cyclization of Substituted N-Aryl Enamines• Pd-Catalyzed Formation of Indoles from Anilines," *Chem. Eur. J.* 17:7298-7303, 2011.

Samec et al., "Efficient Ruthenium-Catalyzed Aerobic Oxidation of Amines by Using a Biomimetic Coupled Catalytic System," *Chem. Eur. J.* 11:2327-2334, 2005.

Sarma et al., "Indium catalyzed tandem hydroamination/hydroalkylation of terminal alkynes," *Chem. Commun.* 47:9525-9527, 2011.

Shen et al., "Dirhodium(II)-Catalyzed Intramolecular C—H Amination of Aryl Azides," *Angew. Chem. Int. Ed.* 47:5056-5059, 2008.

Shi et al., "Indoles from Simple Anilines and Alkynes: Palladium-Catalyzed C—H Activation Using Dioxygen as the Oxidant," *Angew. Chem. Int. Ed.* 48:4572-4576, 2009.

Somei et al., "Simple indole alkaloids and those with a nonrearranged monoterpenoid unit," *Nat. Prod. Rep.* 20:216-242, 2003.

Somei et al., "Simple indole alkaloids and those with a nonrearranged monoterpenoid unit," *Nat. Prod. Rep.* 21:278-311, 2004.

Sridharan et al., "Microwave-Assisted, Solvent-Free Bischler Indole Synthesis," *Synlett* 1:0091- 0095, 2006.

Stuart et al., "Indole Synthesis via Rhodium Catalyzed Oxidative Coupling of Acetanilides and Internal Alkynes," *J. Am. Chem. Soc.* 130:16474-16475, 2008.

Wagaw et al., "A Palladium-Catalyzed Method for the Preparation of Indoles via the Fischer Indole Synthesis," *Journal of the American Chemical Society* 121(44):10251-10263, 1999.

Wei et al., "Palladium-Catalyzed Aerobic Oxidative Cyclization of N-Aryl Imines. Indole Synthesis from Anilines and Ketones," *J. Am. Chem. Soc.* 134:9098-9101, 2012.

Würtz et al., "Palladium-Catalyzed Oxidative Cyclization of N-Aryl Enamines: From Anilines to Indoles," *Angew. Chem. Int. Ed.* 47:7230-7233, 2008.

Xu et al., "Efficient copper-catalyzed coupling of aryl chlorides, bromides and iodides with aqueous ammonia," *Chem. Commun.*:3035-3037 , 2009.

Yoshikai et al., "Iron-Catalyzed Chemoselective ortho Arylation or Aryl Imines by Directed C-H Bond Activation," *Angew. Chem. Int. Ed.* 48:2925-2928, 2009.

Yu et al., "PIDA-Mediated Oxidative C—C Bond Formation: Novel Synthesis of Indoles from N-Aryl Enamines," *Organic Letters* 11(11):2417-2420, 2009.

Zhao et al., "Transfer of Amido Groups from Isolated Rhodium(I) Amides to Alkenes and Vinylarenes," *J. Am. Chem. Soc.* 127:12066-12073, 2005.

\* cited by examiner

PROCESSES FOR PREPARING INDOLES

CROSS-REFERENCE TO RELATED APPLICATION

This application claims the benefit of priority of U.S. provisional application No. 61/577,528 filed on 19 Dec. 2011, the content of which is incorporated herein by reference in its entirety for all purposes.

TECHNICAL FIELD

The invention relates to methods for the synthesis of indoles.

BACKGROUND

Indoles are industrially useful substances as starting material for the preparation of perfumes, amino acids such as tryptophane, and stabilizers for high polymers. They are also important intermediates in the dyestuffs industry. Indoles are also contained in numerous drugs that are already on the market in the pharmaceutical agent or as an intermediate compound en route to the final target compound.

Substituted indoles have frequently been referred to as privileged structures since they are capable of binding to multiple receptors with high affinity, and thus have applications across a wide range of therapeutic areas. As a result, indole ring system is an important building block or intermediate in the synthesis of many pharmaceutical agents. Notably, indole-3-carbinol, found in cruciferous vegetables, inhibits carcinogenesis at the initiation stage and has been shown to inhibit carcinogenesis in several animal species.

Various attempts have been carried out for the synthesis of indoles. For example, one of the most prevalent processes to prepare indoles is the Fischer indole synthesis, which involves producing indoles from a phenylhydrazine and an aldehyde or ketone. However, the process suffers from drawbacks such as the need for acidic and harsh conditions, as well as limited commercial availability of hydrazines. Other known processes include the Bischler indole synthesis and the Larock indole synthesis. However, these known processes are accompanied by one or more problems in that the indole product yield is not high due to formation of by-products, expensive raw materials, and/or need for complex preparation steps.

In view of the above, there remains a need for improved methods to synthesize indoles that address at least one of the above-mentioned problems.

SUMMARY

In a first aspect, the invention refers to a method for the synthesis of an indole. The method comprises oxidizing a N-aryl imine in the presence of a palladium-based catalyst, an oxidant, and a solvent.

In various embodiments, the method is for the synthesis of an indole of Formula (I) or a salt thereof,

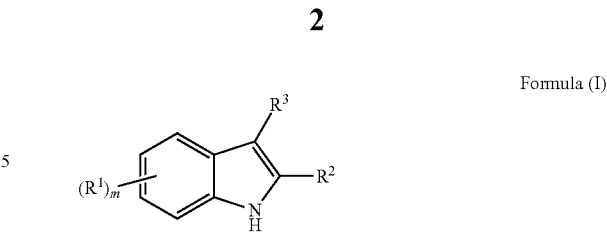

Formula (I)

the method comprising oxidizing a N-aryl imine of Formula (II)

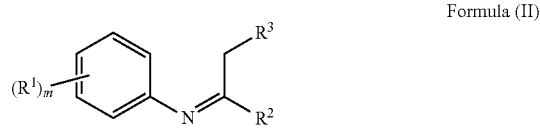

Formula (II)

in the presence of a palladium-based catalyst, an oxidant and a solvent,
wherein
$R^1$ at each occurrence, $R^2$ and $R^3$ are independently selected from the group consisting of hydrogen, optionally substituted $C_1$-$C_{20}$ alkyl, optionally substituted $C_2$-$C_{20}$ alkenyl, optionally substituted $C_2$-$C_{20}$ alkynyl, optionally substituted monocyclic, condensed polycyclic or bridged polycyclic $C_5$-$C_{20}$ aryl, optionally substituted $C_3$-$C_{20}$ mono-, or poly-cycloalkyl, optionally substituted $C_3$-$C_{20}$ mono-, or poly-cycloalkenyl; optionally substituted 2-20-membered heteroalkyl, optionally substituted 2-20-membered heteroalkenyl, optionally substituted 2-20-membered heteroalkynyl, optionally substituted 5-20-membered monocyclic, condensed polycyclic or bridged polycyclic heteroaryl, optionally substituted 3-20-membered mono-, or poly-heterocycloalkyl, and optionally substituted 3-20-membered mono-, or poly-heterocycloalkenyl; halogen, —CN, —NO$_2$, —C(halo), —C(O)R, —C(O)OR, —NC(O)R, —NRR', —OR, wherein R and R' are independently selected from the group consisting of hydrogen, optionally substituted $C_1$-$C_{20}$ alkyl, optionally substituted $C_5$-$C_{20}$ aryl, and halogen;
m is 0, 1, 2, 3, or 4;
wherein
$R^1$ at each occurrence is positioned on the phenyl ring in 3-, 4-, 5-, or 6-position with respect to the bond linking the phenyl to the —N—H group according to Formula (I) or the —N=C group according to Formula (II).

BRIEF DESCRIPTION OF THE DRAWINGS

The invention will be better understood with reference to the detailed description when considered in conjunction with the non-limiting examples and the accompanying drawings, in which:

FIG. 1 is a $^1$H NMR analysis spectrum illustrating intramolecular competition reaction based on Scheme 3a.

DETAILED DESCRIPTION

Figure 1:
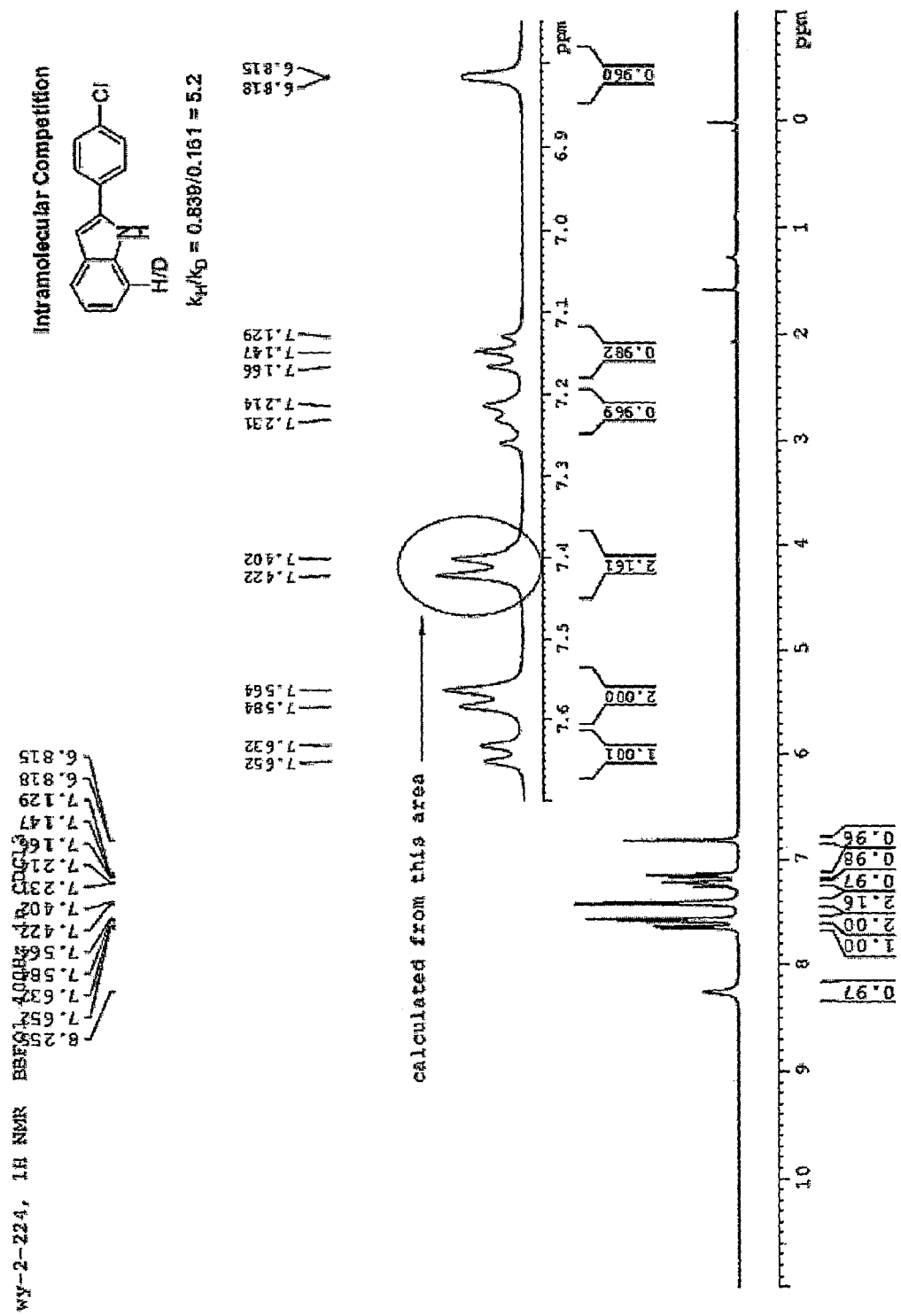

In a first aspect, the present invention refers to a method for the synthesis of an indole.

As used herein, the term "indole" refers to a bi-cyclic heteroaryl comprised of fused phenyl and pyrrole groups. The indole may be substituted or unsubstituted. Examples of indole include, but are not limited to, 1H-indole, 1-methyl-1H-indole, 2-methyl-1H-indole, 3-methyl-1H-indole, 4-methyl-1H-indole, 5-methyl-1H-indole, 6-methyl-1H-indole, 7-methyl-1H-indole, 4-amino-1H-indole, 5-amino-1H-indole, 6-amino-1H-indole, 7-amino-1H-indole, 4-hydroxy-1H-indole, 5-hydroxy-1H-indole, 6-hydroxy-1H-indole, 7-hydroxy-1H-indole, 4-methoxy-1H-indole, 5-methoxy-1H-indole, 6-methoxy-1H-indole, 7-methoxy-1H-indole, 4-chloro-1H-indole, 5-chloro-1H-indole, 6-chloro-1H-indole, 7-chloro-1H-indole, 4-carboxy-1H-indole, 5-carboxy-1H-indole, 6-carboxy-1H-indole, 7-carboxy-1H-indole, 4-nitro-1H-indole, 5-nitro-1H-indole, 6-nitro-1H-indole, 7-nitro-1H-indole, 4-nitrile-1H-indole, 5-nitrile-1H-indole, 6-nitrile-1H-indole, 7-nitrile-1H-indole, 2,5-dimethyl-1H-indole, 1,2-dimethyl-1H-indole, 1,3-dimethyl-1H-indole, 2,3-dimethyl-1H-indole, 5-amino-2,3-dimethyl-1H-indole, 7-ethyl-1H-indole, 5-(aminomethyl)indole, 2-methyl-5-amino-1H-indole, 3-hydroxymethyl-1H-indole, 6-isopropyl-1H-indole, and 5-chloro-2-methyl-1H-indole.

In various embodiments, the method of the first aspect is for the synthesis of an indole of Formula (I) or a salt thereof,

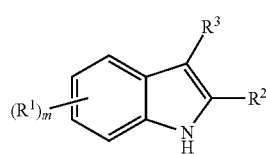

Formula (I)

the method comprising oxidizing a N-aryl imine of Formula (II)

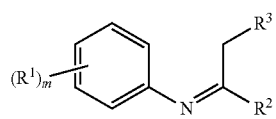

Formula (II)

in the presence of a palladium-based catalyst, an oxidant and a solvent, wherein $R^1$ at each occurrence, $R^2$ and $R^3$ are each independently selected from the group consisting of hydrogen, optionally substituted $C_1$-$C_{20}$ alkyl, optionally substituted $C_2$-$C_{20}$ alkenyl, optionally substituted $C_2$-$C_{20}$ alkynyl, optionally substituted monocyclic, condensed polycyclic or bridged polycyclic $C_5$-$C_{20}$ aryl, optionally substituted $C_3$-$C_{20}$ mono-, or poly-cycloalkyl, optionally substituted $C_3$-$C_{20}$ mono-, or poly-cycloalkenyl; optionally substituted 2-20-membered heteroalkyl, optionally substituted 2-20-membered heteroalkenyl, optionally substituted 2-20-membered heteroalkynyl, optionally substituted 5-20-membered monocyclic, condensed polycyclic or bridged polycyclic heteroaryl, optionally substituted 3-20-membered mono-, or poly-heterocycloalkyl, and optionally substituted 3-20-membered mono-, or poly-heterocycloalkenyl; halogen, —CN, —NO$_2$, —C(halo), —C(O)R, —C(O)OR, —NC(O)R, —NRR', —OR, wherein R and R' are independently selected from the group consisting of hydrogen, optionally substituted $C_1$-$C_{20}$ alkyl, optionally substituted $C_5$-$C_{20}$ aryl, and halogen; m is 0, 1, 2, 3, or 4; wherein R at each occurrence is positioned on the phenyl ring in 3-, 4-, 5-, or 6-position with respect to the bond linking the phenyl to the —N—H group according to Formula (I) or the —N=C group according to Formula (II).

The term "optionally substituted" refers to a group in which none, one, or more than one of the hydrogen atoms has been replaced with one or more substituent group(s) independently selected from a $C_{1-6}$ aliphatic group, hydroxy, alkoxy, cyano, F, Cl, Br, I, nitro, silyl, and amino, including mono- and di-substituted amino groups. As an example, an optionally substituted alkyl group means that the alkyl group may be substituted or unsubstituted. Exemplary substituents include $C_1$-$C_{10}$ alkoxy, $C_5$-$C_{10}$ aryl, $C_5$-$C_{10}$ aryloxy, sulfhydryl, $C_5$-$C_{10}$ arylthio, halogen, hydroxyl, amino, sulfonyl, nitro, cyano, and carboxyl.

The term "aliphatic", alone or in combination, refers to a straight chain or branched chain hydrocarbon comprising at least one carbon atom. Aliphatics include alkyls, alkenyls, and alkynyls. Aliphatics include, but are not limited to, methyl, ethyl, propyl, isopropyl, butyl, isobutyl, tert.-butyl, pentyl, hexyl, ethenyl, propenyl, butenyl, ethynyl, butynyl, propynyl, and the like, each of which may be optionally substituted.

The term "optionally substituted $C_1$-$C_{20}$ alkyl" refers to a fully saturated aliphatic hydrocarbon. The $C_1$-$C_{20}$ alkyl group may be straight chain or branched chain, and may be substituted or unsubstituted. Exemplary substituents have already been mentioned above. Whenever it appears here, a numerical range, such as 1 to 20 or $C_1$-$C_{20}$ refers to each integer in the given range, e.g. it means that an alkyl group comprises only 1 carbon atom, 2 carbon atoms, 3 carbon atoms etc. up to and including 20 carbon atoms. Examples of alkyl groups may be, but are not limited to, methyl, ethyl, n-propyl, isopropyl, n-butyl, isobutyl, s-butyl, t-butyl, n-hexyl, n-heptyl, n-octyl, n-nonyl or n-decyl and the like.

The term "optionally substituted $C_2$-$C_{20}$ alkenyl" refers to an aliphatic hydrocarbon having one or more carbon-carbon double bonds. The $C_2$-$C_{20}$ alkenyl group may be straight chain or branched chain, and may be substituted or unsubstituted. $C_2$-$C_{20}$ alkenyl groups include, without limitation, vinyl, allyl, 1-propenyl, 1-butenyl, 2-butenyl, 3-butenyl, 2-methyl-1-propenyl, and 2-methyl-2-propenyl.

The term "optionally substituted $C_2$-$C_{20}$ alkynyl" refers to an aliphatic hydrocarbon having one or more carbon-carbon triple bonds. The $C_2$-$C_{20}$ alkynyl group may be straight chain or branched chain, and may be substituted or unsubstituted. Examples of alkynyl groups may be, but are not limited to, ethynyl, 1-propynyl, 2-propynyl, 1-butynyl, 2-butynyl, and 3-butynyl, and the like.

In the context of various embodiments, the term "optionally substituted $C_5$-$C_{20}$ aryl" refers to a group comprising an aromatic ring, wherein each of the atoms forming the ring is a carbon atom. Aromatic in this context means a group comprising a covalently closed planar ring having a delocalized π-electron system comprising 4w+2 π-electrons, wherein w is an integer of at least 1, for example 1, 2, 3 or 4. Aryl rings may be formed by 5, 6, 7, 8, 9, 10, 11, 12, 13, 14, 15, 16, 17, 18, 19 or 20 carbon atoms. The $C_5$-$C_{20}$ aryl may be substituted or unsubstituted. In various embodiments, such a group is a $C_5$-$C_{14}$ aryl, a $C_6$-$C_{12}$ aryl, a $C_6$ aryl, a $C_{10}$ aryl, a $C_{12}$ aryl, or a $C_{14}$ aryl.

The term "monocyclic aryl" refers to a monocyclic aromatic carbon ring. Examples of monocyclic aryl groups may be, but are not limited to, phenyl and the like. The term "condensed polycyclic aryl" refers to an aromatic carbon ring structure in which more than 1 monocyclic carbon rings are condensed or fused. Examples include naphthyl, anthracenyl, and phenanthryl. The term "bridged polycyclic aryl" refers to an aromatic carbon ring structure in which 1 aromatic carbon ring is connected to another aromatic carbon ring via a bridging group or atom, such as an alkyl group, O, S, or N, or via a direct bond. Examples include biphenyl, triphenyl, phenylnaphthyl, binaphthyl, diphenyl ether, diphenyl sulphide, diphenyl disulphide, and the like.

In the context of various embodiments, by "$C_3$-$C_{20}$ cycloalkyl" is meant a group comprising a non-aromatic ring (i.e. an alicyclic ring) wherein each of the atoms forming the ring is a carbon atom. The $C_3$-$C_{20}$ cycloalkyl may be formed by three, four, five, six, seven, eight, nine, or more than nine carbon atoms including twenty carbon atoms. The $C_3$-$C_{20}$ cycloalkyl may be substituted or unsubstituted. The term "mono-cycloalkyl" refers to a mono-alicyclic ring. Examples of $C_3$-$C_{20}$ mono-cycloalkyl may include, but are not limited to, cyclopropane, cyclobutane, cyclopentane, cyclohexane, cycloheptane, and cyclooctane. The term "poly-cycloalkyl" refers to a carbon ring structure in which more than 1 mono-alicyclic carbon rings are fused or bridged. Examples include bicyclobutane, bicyclopentane, tricyclopentane, tricyclohexane, and tetracyclodecane.

In the context of various embodiments, by "$C_3$-$C_{20}$ cycloalkenyl" is meant a group comprising a non-aromatic ring (i.e. an alicyclic ring) wherein each of the atoms forming the ring is a carbon atom and contains one or more double bonds. The $C_3$-$C_{20}$ cycloalkenyl may be formed by three, four, five, six, seven, eight, nine, or more than nine carbon atoms including twenty carbon atoms. The $C_3$-$C_{20}$ cycloalkenyl may be substituted or unsubstituted. The term "mono-cycloalkenyl" refers to a mono-alicyclic ring which contains one or more double bonds. Examples of $C_3$-$C_{20}$ mono-cycloalkenyl include cyclopropene, cyclobutene, cyclopentene, cyclohexene, cycloheptene, cyclooctene, 1,3-cyclohexadiene, and 1,4-cyclohexadiene, among others. The term "poly-cycloalkenyl" refers to a carbon ring structure in which more than 1 mono-alicyclic carbon rings are fused or bridged, and the structure has one or more double bonds. Examples of $C_3$-$C_{20}$ poly-cycloalkenyl include bicyclobutene, bicyclopentene, tricyclopentene, tricyclohexene, and tetracyclodecene.

In the context of various embodiments, the term "heteroalkyl" refers to an alkyl wherein one or more carbon atoms are replaced by a heteroatom. The term "heteroatom" refers to an atom other than carbon present in a main chain of a hydrocarbon. Heteroatoms are typically independently selected from oxygen, sulfur, nitrogen, and phosphorus.

In line with the above, the term "heteroalkenyl" refers to an alkenyl wherein one or more carbon atoms are replaced by a heteroatom. The term "heteroalkynyl" refers to an alkynyl wherein one or more carbon atoms are replaced by a heteroatom.

The terms "1 to 20-membered" or "2 to 20-membered", refer to the number of straight chain or branched chain atoms including carbon and heteroatoms. In various embodiments, the number of straight chain or branched chain atoms for a 1-20-membered heteroalkyl is from 1-14, from 1-8, from 1-6, from 2-10, from 2-6, from 3-12, from 3-8, or from 4-10. In various embodiments, the number of straight chain or branched chain atoms for a 2-20-membered heteroalkenyl or a 2-20-membered heteroalkynyl is independently from 2-14, from 2-10, from 2-8, from 3-12, from 3-8, or from 4-10.

In the context of various embodiments, the terms "5-20-membered heteroaryl", has the general above definition of "$C_5$-$C_{20}$ aryl", except in that the heteroaryl is now termed as 5-20-membered, as 1 to 4 of the carbon atoms may be replaced by heteroatoms. Examples of heteroatoms have already been mentioned above. Examples of heteroaryl groups include, but are not limited to, furan, benzofuran, thiophene, benzothiophene, pyrrole, pyridine, indole, oxazole, benzoxazole, isoxazole, benzisoxazole, thiazole, benzothiazole, imidazole, benzimidazole, pyrazole, indazole, tetrazole, quinoline, isoquinoline, pyridazine, purine, pyrazine, furazan, triazole, benzotriazole, pteridine, phenoxazole, oxadiazole, benzopyrazole, quinolizine, cinnoline, phthalazine, quinazoline or quinoxaline, and the like.

The terms "3-20-membered heterocycloalkyl" and "3-20-membered heterocycloalkenyl" have the general above definitions of "$C_3$-$C_{20}$ cycloalkyl" and "$C_3$-$C_{20}$ cycloalkenyl" respectively, except in the alicyclic ring at least one of the carbon atom in the ring is substituted with a heteroatom. The $C_3$-$C_{20}$ heterocycloalkyl or $C_3$-$C_{20}$ heterocycloalkenyl may be formed by three, four, five, six, seven, eight, nine, or more than nine atoms including twenty atoms. The $C_3$-$C_{20}$ heterocycloalkyls and $C_3$-$C_{20}$ heterocycloalkenyls may be substituted or unsubstituted. Examples of $C_3$-$C_{20}$ heterocycloalkyls and $C_3$-$C_{20}$ heterocycloalkenyls include, but are not limited to, lactams, lactones, cyclic imides, cyclic thioimides, cyclic carbamates, tetrahydrothiopyran, 4H-pyran, tetrahydropyran, piperidine, 1,3-dioxin, 1,3-dioxane, 1,4-dioxin, 1,4-dioxane, piperazine, 1,3-oxathiane, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, morpholine, trioxane, hexahydro-1,3,5-triazine, tetrahydrothiophene, tetrahydrofuran, pyrroline, pyrrolidine, pyrrolidone, pyrrolidione, pyrazoline, pyrazolidine, imidazoline, imidazolidine, 1,3-dioxole, 1,3-dioxolane, 1,3-dithiole, 1,3-dithiolane, isoxazoline, isoxazohdme, oxazoline, oxazolidine, oxazolidinone, thiazoline, thiazolidine, and 1,3-oxathiolane.

The term "halogen" or "halo" as used herein refers to fluorine, chlorine, bromine or iodine.

The term "N-aryl" refers to a nitrogen atom attached to an aryl. The term "imine" refers to a functional group or type of chemical compound containing a carbon-nitrogen double bond (N=C) with the nitrogen atom of an amine connected to an aryl group or an alkyl group but not hydrogen. The term imine group comprises both aldimines and ketimines. Accordingly, the term "N-aryl imine" refers to an imine in which the nitrogen is connected to a N-aryl group, and may alternatively be termed "N-aryl aldimine" or "N-aryl ketimine" depending on whether the C atom of the N=C group is bonded to one (aldimine) or two (ketimine) hydrocarbyl groups.

In various embodiments, m is 0, 1, 2, 3, or 4. When m=0, this means that $R^1$ is not present. $R^1$ at each occurrence may be positioned on the phenyl ring in 3-, 4-, 5-, or 6-position with respect to the bond linking the phenyl to the —N—H group on the indole. In terms of the N-aryl imine, this means that $R^1$ at each occurrence may be positioned on the phenyl ring in 3-, 4-, 5-, or 6-position with respect to the bond linking the phenyl to the —N=C group present on the N-aryl imine having reference to Formula (II).

It is specified herein that $R^1$ is not located on the phenyl ring in the 2-position with respect to the bond linking the phenyl ring to the —N—H group on the indole or the —N=C group on the N-aryl imine, so as not to block the cyclization process of the imine in forming the indole.

With reference to Formula (I) for example, when m=1, $R^1$ may be located on the phenyl ring in one of the 3-, 4-, 5-, or 6-position with respect to the bond linking the phenyl to the —N—H group on the indole. In some embodiments, $R^1$ is located on the phenyl ring in 4-position with respect to the bond linking the phenyl to the —N—H group on the indole. When m=2, for example, $R^1$ may be located on two of the 3-, 4-, 5-, or 6-position with respect to the bond linking the phenyl to the —N—H group on the indole, such as the 3- and 5-position, or the 4- and 6-position. In various embodiments, two $R^1$ may combine to form a ring selected from the group consisting of substituted or unsubstituted monocyclic, condensed polycyclic or bridged polycyclic $C_5$-$C_{20}$ aryl, substituted or unsubstituted $C_3$-$C_{20}$ mono-, or poly-cycloalkyl, substituted or unsubstituted $C_3$-$C_{20}$ mono-, or poly-cycloalkenyl, substituted or unsubstituted 5-20-membered monocyclic, condensed polycyclic or bridged polycyclic heteroaryl, substituted or unsubstituted 3-20-membered mono-, or poly-heterocycloalkyl, and substituted or unsubstituted 3-20-membered mono-, or poly-heterocycloalkenyl. When m=3, for example, $R^1$ may be located on three of the 3-, 4-, 5-, or 6-position with respect to the bond linking the phenyl to the —N—H group on the indole, such as the 3-, 4- and 5-position, or 4-, 5- and 6-position. When m=4, $R^1$ may be located on all of the 3-, 4-, 5-, and 6-position with respect to the bond linking the phenyl to the —N—H group on the indole.

In various embodiments, $R^1$ at each occurrence is independently selected from the group consisting of optionally substituted $C_1$-$C_{20}$ alkyl, optionally substituted 2-20-membered heteroalkyl, optionally substituted 3-20-membered mono-, or poly-heterocycloalkyl, optionally substituted monocyclic, condensed polycyclic or bridged polycyclic $C_5$-$C_{20}$ aryl, optionally substituted 5-20-membered monocyclic, condensed polycyclic or bridged polycyclic heteroaryl; halogen, —CN, —NO$_2$, —C(halo), —C(O)OR, —NC(O)R, —NRR', and —OR, wherein R and R' are independently selected from the group consisting of hydrogen, optionally substituted $C_1$-$C_{20}$ alkyl, optionally substituted $C_5$-$C_{20}$ aryl, and halogen.

For example, $R^1$ may be independently selected from the group consisting of alkyl, —(O)alkyl, —C(O)Oalkyl, —NCO(alkyl), aryl, halogen, haloalkyl, —CN, and —NO$_2$.

In more specific embodiments, $R^1$ may be independently selected from the group consisting of —CH$_3$, —OCH$_3$, —CO$_2$(C$_2$H$_5$), —NHCOCH$_3$, phenyl, —Cl, —Br, —CF$_3$, —CN, and —NO$_2$.

In various embodiments, $R^2$ is selected from the group consisting of optionally substituted $C_2$-$C_{20}$ alkenyl, optionally substituted 2-20-membered heteroalkenyl, optionally substituted monocyclic, condensed polycyclic or bridged polycyclic $C_5$-$C_{20}$ aryl, and optionally substituted 5-20-membered monocyclic, condensed polycyclic or bridged polycyclic heteroaryl.

In specific embodiments, $R^2$ may be one of

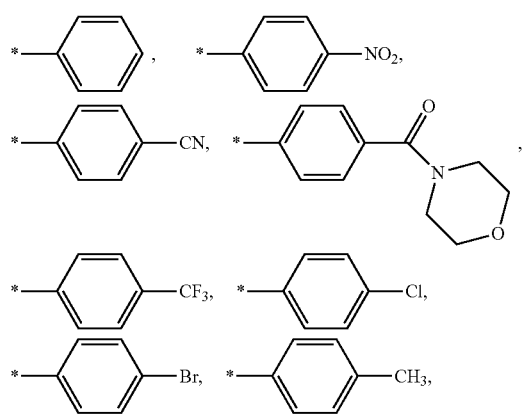

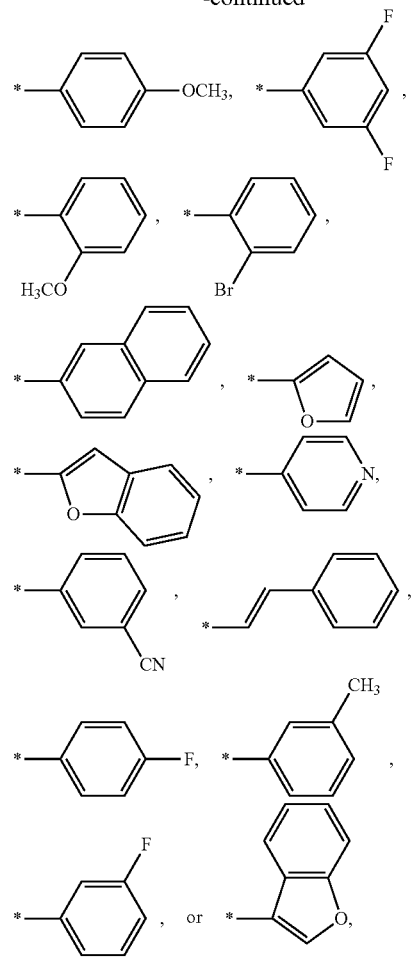

wherein * denotes the point in which $R^2$ is connected to the rest of the parent molecular moiety.

In some embodiments, $R^2$ is selected from the group consisting of optionally substituted $C_1$-$C_{20}$ alkyl, optionally substituted 2-20-membered heteroalkyl, optionally substituted $C_3$-$C_{20}$ mono-, or poly-cycloalkyl, optionally substituted 3-20-membered mono-, or poly-heterocycloalkyl, and —C(O)O-alkyl.

More specifically, $R^2$ may be one of 2-cyclopropyl-, 2-t-butyl-, —CH$_3$, or —CO$_2$(C$_2$H$_5$).

In various embodiments, $R^3$ is selected from the group consisting of optionally substituted $C_1$-$C_{20}$ alkyl, optionally substituted 2-20-membered heteroalkyl, optionally substituted $C_2$-$C_{20}$ alkenyl, optionally substituted 2-20-membered heteroalkenyl, optionally substituted monocyclic, condensed polycyclic or bridged polycyclic $C_5$-$C_{20}$ aryl, optionally substituted 5-20-membered monocyclic, condensed polycyclic or bridged polycyclic heteroaryl, and —CN. In specific embodiments, $R^3$ is —CN or phenyl.

In various embodiments, the indole is 2-aryl indole, 2-alkenyl indole, 2,3-diaryl indole, 2-aryl-3-alkenyl indole, 2-alkenyl-3-aryl indole, 2,3-dialkenyl indole, 2-aryl-3-alkyl indole, or 2-alkenyl-3-alkyl indole. The aryl, alkenyl, and alkyl as described herein refers also to their hetero-forms, i.e. heteroaryl, heteroalkenyl and heteroalkyl, and are optionally substituted. Examples of aryl, alkenyl, alkyl, heteroaryl, heteroalkenyl and heteroalkyl have been described above.

In specific embodiments, the indole is
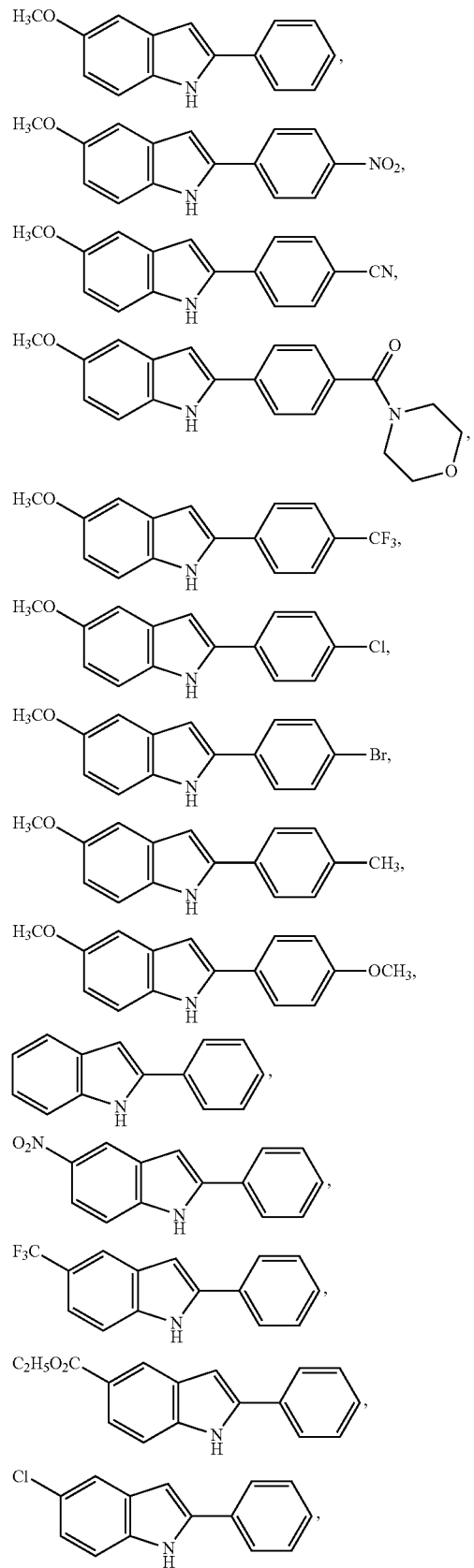
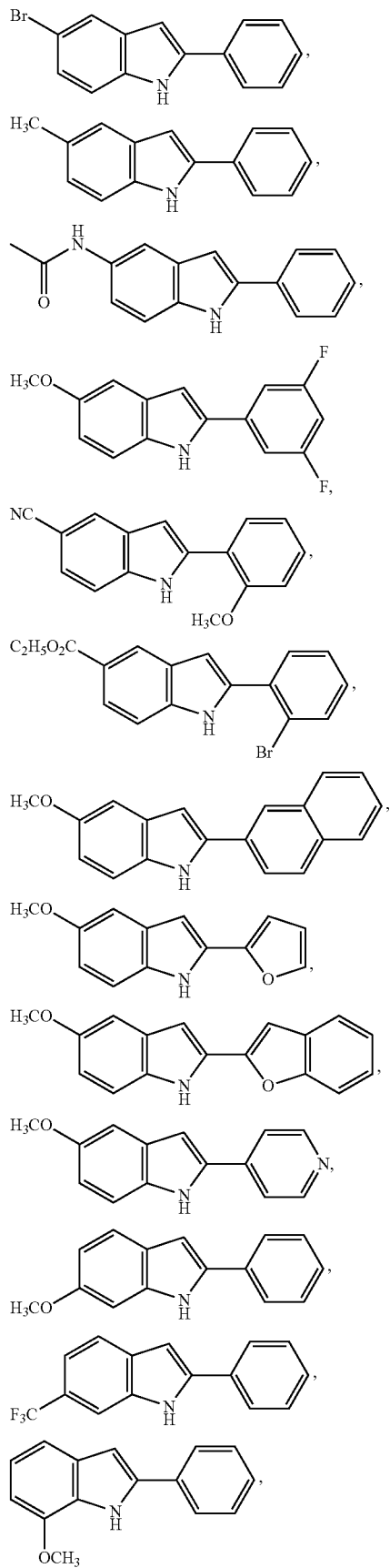

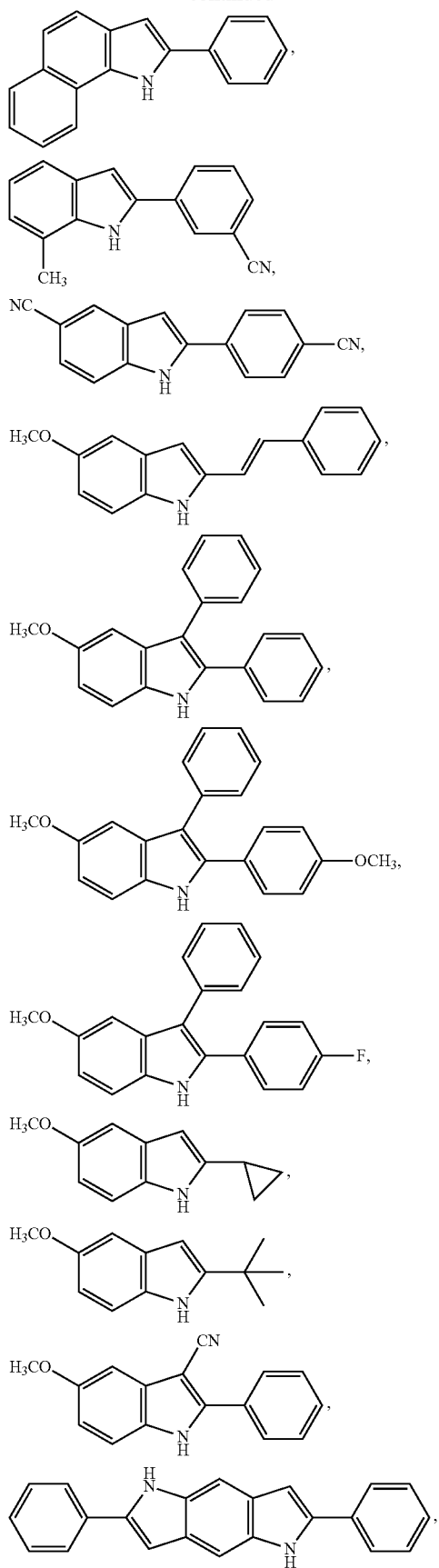
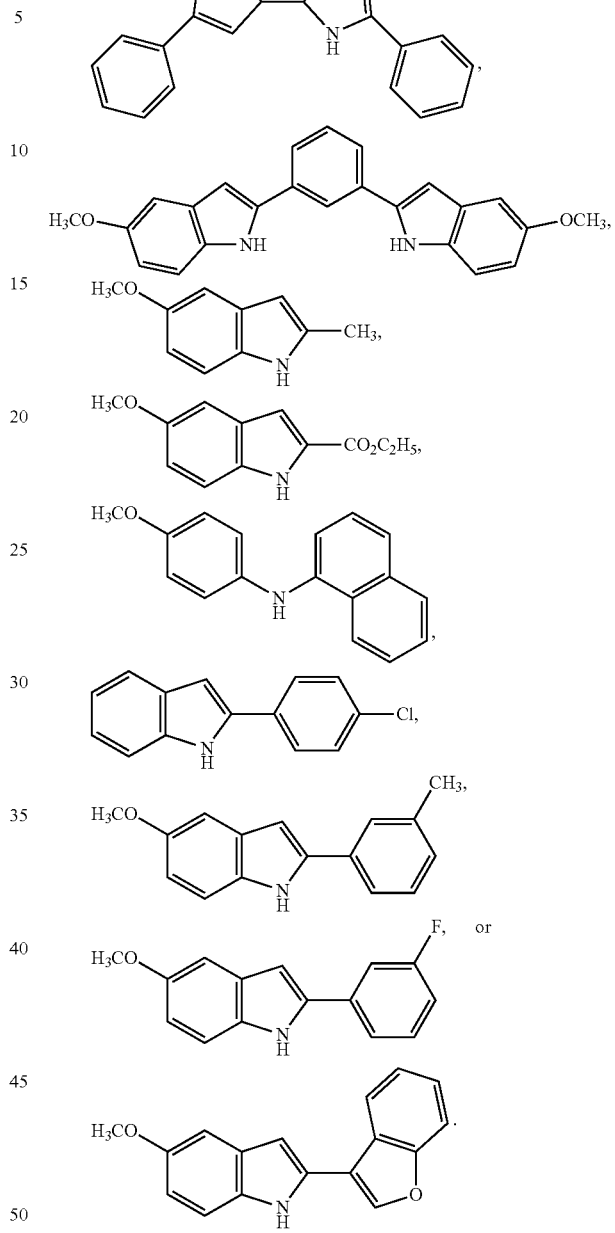

The method for the synthesis of an indole according to various embodiments of the invention includes oxidizing a N-aryl imine in the presence of a palladium-based catalyst.

In various embodiments, the palladium-based catalyst is selected from the group consisting of palladium metal, palladium (II) acetate, sodium palladium (II) chloride, palladium (II) acetylacetonate, palladium(II) trifluoroacetate, palladium hydroxide, palladium(II) bromide, palladium (II) chloride, palladium(II) cyanide, palladium(II) hexafluoroacetylacetonate, palladium(II) iodide, palladium(II) nitrate dehydrate, palladium(II) nitrate hydrate, palladium(II) oxide, palladium (II) propionate, palladium (II) sulfate, palladium (II) sulfide, or mixtures thereof. In some embodiments, the palladium-based catalyst comprises or consists essentially of palladium (II) acetate. In one embodiment, the palladium-based catalyst consists of palladium (II) acetate.

The amount of palladium-based catalyst may be in the range of about 0.1 mol % to about 20 mol % with respect to the amount of N-aryl imine, such as about 0.1 mol % to about 15 mol %, about 0.1 mol % to about 10 mol %, about 0.1 mol % to about 5 mol %, about 1 mol % to about 5 mol %, about 1 mol % to about 10 mol %, about 1 mol % to about 15 mol %, about 1 mol % to about 20 mol %, about 5 mol % to about 20 mol %, about 5 mol % to about 15 mol %, or about 10 mol %. In various embodiments, the amount of palladium-based catalyst is in the range of about 5 mol % to about 10 mol % with respect to the amount of N-aryl imine.

In addition to the palladium-based catalyst, the method according to various embodiments of the invention includes oxidizing the N-aryl imine in the presence of an oxidant.

In various embodiments, the oxidant is selected from the group consisting of copper (II) acetate, copper (II) chloride ($CuCl_2$), silver (I) acetate, silver (I) carbonate, iodobenzene diacetate ($PhI(OAc)_2$), 2,3-dichloro-5,6-dicyanobenzoquinone (DDQ), benzoquinone, tert-butylhydroperoxide, di-tert-butyl peroxide (tBuOOtBu), tert-butyl benzoyl peroxide (BzOOtBu), tert-butyl perbenzoate, molecular oxygen ($O_2$), air, or combinations thereof. One or more oxidants may be used in combination. For example, the oxidant may comprise air and copper (II) acetate. In some embodiments, the oxidant comprises or consists essentially of copper (II) acetate. In one embodiment, the oxidant consists of copper (II) acetate. In various embodiments, the oxidant may be air or molecular oxygen ($O_2$). Advantageously, use of air or molecular oxygen as the oxidant offers a much greener option in terms of impact to the environment as compared to use of chemical reagents as the oxidant.

Depending on the type of oxidant used, the amount of oxidant may be present in the range of about 0.5 equivalence to about 5 equivalence of the amount of N-aryl imine, such as about 0.5 to about 4, about 0.5 to about 3, about 0.5 to about 2, about 0.5 to about 1, about 1 to about 5, about 2 to about 5, about 3 to about 5, about 2, about 3, about 4, or about 5 equivalence. In some embodiments, the amount of oxidant is about 2 equivalence to about 3 equivalence of the amount of N-aryl imine. Referring to Formula (II), in one embodiment where $R^1$ is —$OCH_3$, $R^2$ is phenyl, and $R^3$ is hydrogen, the amount of copper (II) acetate present is about 3 equivalence of the amount of N-aryl imine.

The method according to various embodiments of the invention includes oxidizing the N-aryl imine in the presence of a solvent. In various embodiments, the solvent is selected from the group consisting of dimethylsulfoxide, dimethylformamide, dimethylacetamide, dioxane, and toluene. In some embodiments, the solvent comprises or consists essentially of dimethylsulfoxide. In one embodiment, the solvent consists of dimethylsulfoxide (DMSO).

The method may further comprise reacting in the presence of an additive. The additive may comprise a quaternary ammonium salt of Formula (III)

 Formula (III)

wherein
$R_4$ at each occurrence is independently selected from $C_1$-$C_{20}$ alkyl;
n is 1, 2, 3 or 4; and
X is selected from the group consisting of a halogen and —$OCOCH_3$.

Examples of $C_1$-$C_{20}$ alkyl and halogen have already been mentioned above.

In various embodiments, the additive is selected from the group consisting of $Bu_4NBr$, $Bu_4NCl$, $Bu_4NI$, and $Bu_4NOCOCH_3$. In some embodiments, the additive comprises or consists essentially of $Bu_4NBr$.

The amount of additive may be about 1 equivalence to about 3 equivalence of the amount of N-aryl imine, such as about 1 to about 2.5, about 1 to about 2, about 1.5 to about 3, about 2 to about 3, about 1 equivalence, about 2 equivalence, or about 3 equivalence.

In some embodiments, the additive may comprise a ligand for the palladium-based catalyst. The ligand may be included to facilitate action of the palladium-based catalyst in synthesis of the indole. For example, the use of strong σ-donating ligands such as trialkylphosphines may increase the electron density around the palladium metal, thereby accelerating the oxidative action of the catalyst. Given that this step may be the rate determining step, this may result in increase in rate of the catalytic reaction. The ligand used may also determine the mechanism at which the reaction takes place, since this may be affected by, for example, size of the ligand.

In various embodiments, the ligand is selected from the group consisting of pyridine, 2,2'-bipyridine, 1,10-phenanthroline, $PPh_3$, dppm, dppe, dppp, dcpe, $P(c\text{-hex})_3$, $P(tBu)_3$, $P(C_6F_5)_3$, $P(2,4,6\text{-Me}_3C_6H_2)_3$, and mixtures thereof.

The amount of ligand may be about 1 equivalence to about 2 equivalence of the amount of palladium present in the palladium-based catalyst, such as about 1 to about 1.5, about 1.5 to about 2, about 1 to about 1.2, about 1 equivalence, about 1.5 equivalence, or about 2 equivalence. This means that if palladium loading in the palladium-based catalyst is about 5 mol % to about 10 mol %, the amount of ligand in the additive may range from about 5 mol % to about 20 mol %.

In various embodiments, the method is carried out at a temperature in the range of about 0° C. to about 150° C., such as about 0° C. to about 100° C., about 0° C. to about 50° C., about 50° C. to about 150° C., about 100° C. to about 150° C., about 20° C. to about 60° C., or about 25° C. to about 40° C. In one embodiment, the method is carried out at a temperature of about 40° C. In another embodiment, the method is carried out at room temperature.

In various embodiments, the method is carried out at atmospheric pressure.

The method may be carried out over a short period to a long period. In various embodiments, the method may be carried out for a period of between about 1 hour and about 100 hours, such as between about 12 hours and about 48 hours, about 24 hours and about 48 hours, about 12 hours and about 24 hours, or about 24 hours.

The invention illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims and non-limiting examples. In addition, where features or aspects of the invention are described in terms of Markush groups, those skilled in the art will recognize that the invention is also thereby described in terms of any individual member or subgroup of members of the Markush group.

EXPERIMENTAL SECTION

Various embodiments relate to an operationally simple, palladium-catalyzed cyclization reaction of N-aryl imines, affording indoles via the oxidative linkage of two C—H bonds. The reaction may be carried out under mild conditions using molecular oxygen as the sole oxidant. The process allows quick and atom-economical assembly of indole rings from inexpensive and readily available anilines and ketones and tolerates a broad range of functional groups.

Example 1

Materials and Methods

Unless otherwise noted, materials were purchased from Aldrich, Alfa Aesar, and other commercial suppliers and were used as received. Anhydrous DMSO was distilled over $CaH_2$ and stored under $N_2$ or purchased from Aldrich without further purification.

All reactions dealing with air- and moisture-sensitive compounds were carried out in dry reaction vessels under a nitrogen atmosphere. Analytical thin-layer chromatography (TLC) was performed on Merck 60 F254 silica gel plates. $^1H$ and $^{13}C$ nuclear magnetic resonance (NMR) spectra were recorded on Bruker AV-400 (400 MHz) NMR spectrometers. $^1H$ and $^{13}C$ NMR spectra are reported in parts per million (ppm) downfield from an internal standard, tetramethylsilane (0 ppm) and $CHCl_3$ (77.0 ppm), respectively. Gas chromatographic (GC) analysis was performed on a Shimadzu GC-2010 system equipped with and FID detector and a capillary column, DB-5 (Agilent J&W, 0.25 mm i.d.×30 m, 0.25 μm film thickness). High-resolution mass spectra (HRMS) were obtained with a Q-T of Premier LC HR mass spectrometer. Melting points were determined using a capillary melting point apparatus and are uncorrected.

Example 2

Preparation of Starting Materials

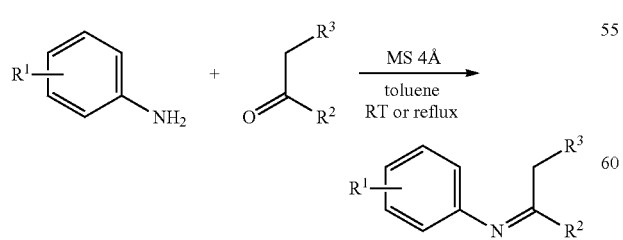

All imines were synthesized by condensation of the corresponding anilines and ketones according to literature procedures (Mrsic, N., Minnaard, A. J., Feringa, B. L., de Vries, J. G. *J. Am. Chem. Soc.* 2009, 131, 8358; Gautier, F. M, Jones, S., Martin, S. *J. Org. Biomol. Chem.* 2009, 7, 229) and purified by recrystallization from EtOAc/hexane or by flash chromatography on silica gel.

Below are summarized characterization data for newly synthesized imines. $^1H$ and $^{13}C$ NMR spectral data for the rest of the imines (1a (Samec, J. S. M; Ell, A. H.; Backvall, J. E. *Chem. Eur. J.* 2005, 11, 2327), 1b (Gautier, F. M; supra), 1c (Yoshikai, N.; Matsumoto, A.; Norinder, J.; Nakamura, E. *Angew. Chem. Int. Ed.* 2009, 48, 2925), 1d (Lee, P.-S.; Fujita, T; Yoshikai, N. *J. Am. Chem. Soc.* 2011, 133, 17283), 1e (Yoshikai, N.; supra), 1f (Moessner, C.; Bolm, C. *Angew. Chem. Int. Ed.* 2005, 44, 7564), 1g (Yoshikai, N.; supra), 1h (Kutlescha, K; Venkanna, G. T.; Kempe, R. *Chem. Commun.* 2011, 47, 4183), 1i (Imamoto, T; Iwadate, N.; Yoshida, K. *Org. Lett.* 2006, 8, 2289), 1j (Gautier, F. M; supra), 1k (Sarma, R.; Prajapati, D. *Chem. Commun.* 2011, 47, 9525), 1l (Zhao, P.; Krug, C.; Hartwig, J. F. *J. Am. Chem. Soc.* 2005, 127, 12066), 1n (Sarma, R.; supra), 1o (Han, Z.; Wang, Z.; Zhang, X; Ding, K *Angew. Chem. Int. Ed.* 2009, 48, 5345), 1p (Han, Z.; supra), 1r (Gao, K.; Yoshikai, N. *Angew. Chem. Int. Ed.* 2011, 50, 6888), 1u (Moessner, C.; supra), 1v (Malkov, A. V.; Vranková, K; Stoncius, S.; Kocovsky, P. *J. Org. Chem.* 2009, 74, 5839), 1w (Malkov, A. V.; supra), 1x (Malkov, A. V.; supra), 1y (Liu, X-Y; Ding, P.; Huang, J.-S.; Che, C.-M *Org. Lett.* 2007, 9, 2645), 1aa (Mrsic, N.; supra), 1ab (Sarma, R.; supra), 1ae (Ackland, M. J.; Danks, T. N.; Howells, M. E. *J. Chem. Soc. Perkin Trans.* 1 1998, 813), 1aj (Malkov, A. V.; supra), 1ak (Yu, W; Du, Y.; Zhao, K *Org. Lett.* 2009, 11, 2417), and 1ar (Yoshikai, N; supra)) showed good agreement with data in literature.

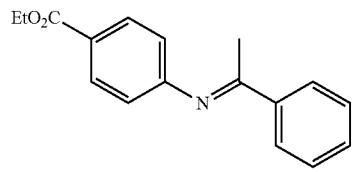 [SMILES: CCOC(=O)c1ccc(/N=C(\C)c2ccccc2)cc1]

(E)-Ethyl 4-((1-phenylethylidene)amino)benzoate (1m)

Yellow solid (60% yield); Mp=89-90° C.; $^1H$ NMR (400 MHz, $CDCl_3$): δ 8.07-8.04 (m, 2H), 7.98-7.96 (m, 2H), 7.49-7.43 (m, 3H), 6.85-6.82 (m, 2H), 4.38 (q, J=7.1 Hz, 2H), 2.23 (s, 3H), 1.40 (t, J=7.1 Hz, 3H); $^{13}C$ NMR (100 MHz, $CDCl_3$): δ 166.6, 165.7, 156.0, 138.9, 130.9, 130.8, 128.5, 127.3, 125.4, 119.1, 60.7, 17.6, 14.4; HRMS (ESI) Calcd for $C_{17}H_{17}NO_2$ [M+H]$^+$ 268.1338, found 268.1340.

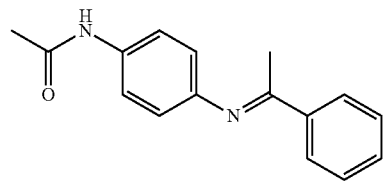 [SMILES: CC(=O)Nc1ccc(/N=C(\C)c2ccccc2)cc1]

(E)-N-(4-((1-phenylethylidene)amino)phenyl)acetamide (1q)

Yellow solid (71% yield); Mp=164-165° C.; $^1H$ NMR (400 MHz, $CDCl_3$) δ 7.97-7.94 (m, 2H), 7.49-7.43 (m, 5H), 7.37

(brs, 1H), 6.76 (d, J=8.5 Hz, 2H), 2.24 (s, 3H), 2.17 (s, 3H); $^{13}$C NMR (100 MHz, CDCl$_3$) δ 168.3, 166.1, 148.1, 139.5, 133.5, 130.5, 128.4, 127.2, 120.9, 120.0, 24.5, 17.5; HRMS (ESI) Calcd for C$_{16}$H$_{16}$N$_2$O [M+H]$^+$ 253.1341, found 253.1340.

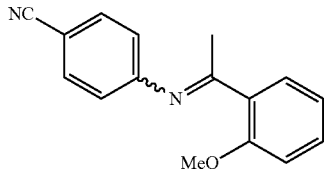 [SMILES: COc1ccccc1C(C)=Nc1ccc(C#N)cc1]

4-((1-(2-Methoxyphenyl)ethylidene)amino)benzonitrile (1s)

Yellow solid (65% yield); Approx. 1.5:1 mixture of E and Z isomers; $^1$H NMR (400 MHz, CDCl$_3$): Z isomer: δ 7.35 (d, J=8.0 Hz, 2H), 7.19 (t, J=7.4 Hz, 1H), 6.84 (d, J=7.0 Hz, 1H), 6.80 (d, J=7.0 Hz, 1H), 6.75 (d, J=8.2 Hz, 1H), 6.71 (d, J=8.2 Hz, 2H), 3.70 (s, 3H), 2.48 (s, 3H); E isomer: δ 7.62 (d, J=6.0 Hz, 2H), 7.58 (t, J=7.6 Hz, 1H), 7.40 (t, J=8.0 Hz, 1H), 7.02 (t, J=7.6 Hz, 1H), 6.96 (d, J=8.02 Hz, 1H), 6.90 (d, J=8.0 Hz, 2H), 3.88 (s, 3H), 2.19 (s, 3H); $^{13}$C NMR (100 MHz, CDCl$_3$): δ 170.2, 169.8, 157.4, 155.3, 155.2, 154.9, 133.1, 132.3, 131.2, 130.1, 130.0, 129.3, 127.5, 127.2, 120.8, 120.7, 120.3, 120.0 (×2), 119.2, 111.2, 110.6, 106.4, 106.1, 55.3, 55.0, 28.3, 21.4; HRMS (ESI) Calcd for C$_{16}$H$_{15}$N$_2$O [M+H]$^+$ 251.1184, found 251.1183.

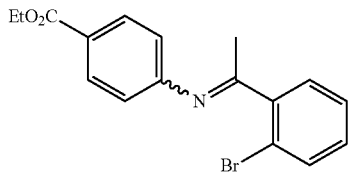 [SMILES: CCOC(=O)c1ccc(N=C(C)c2ccccc2Br)cc1]

Ethyl 4-((1-(2-bromophenyl)ethylidene)amino)benzoate (1t)

Approx. 1.2:1 mixture of E and Z isomers; Yellow solid (70% yield); $^1$H NMR (400 MHz, CDCl$_3$): Z isomer: δ 7.81-7.80 (m, 2H), 7.41-7.38 (m, 1H), 7.28-7.24 (m, 2H), 7.05 (td, J=7.6, 1.5 Hz, 1H), 6.80-6.78 (m, 2H), 4.27 (q, J=7.1 Hz, 2H), 2.53 (s, 3H), 1.32 (t, J=7.0 Hz, 3H); E isomer: δ 8.08-8.06 (m, 2H), 7.62 (d, J=8.0 Hz, 1H), 7.45-7.41 (m, 2H), 7.14 (t, J=7.4 Hz, 1H), 6.94-6.92 (m, 2H), 4.38 (q, J=7.1 Hz, 2H), 2.19 (s, 3H), 1.40 (t, J=7.1 Hz, 3H); $^{13}$C NMR (100 MHz, CDCl$_3$): δ 169.9, 169.7, 154.7, 154.6, 142.5, 140.1, 133.2, 132.7, 130.9, 130.2, 130.1, 129.7, 128.7, 128.2, 127.6, 127.2, 126.0, 125.5, 119.8, 119.3, 118.9, 60.8, 60.7, 28.1, 21.5, 14.4, 14.3; HRMS (ESI) Calcd for C$_{17}$H$_{16}$BrNO$_2$ [M+H]$^+$ 346.0443, found 346.0446.

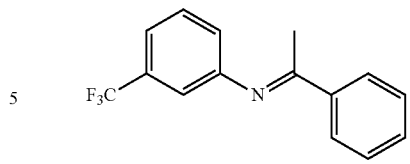

(E)-N-(1-Phenylethylidene)-3-(trifluoromethyl)aniline (1z)

Yellow oil (75% yield, eluent=hexane/EtOAc (95:5)); $^1$H NMR (400 MHz, CDCl$_3$): δ 7.98 (dd, J=7.7, 1.4 Hz, 2H), 7.50-7.45 (m, 4H), 7.36 (d, J=7.7 Hz, 1H), 7.01 (s, 1H), 6.98 (d, J=7.9 Hz, 1H), 2.25 (s, 3H); $^{13}$C NMR (100 MHz, CDCl$_3$): δ 166.6, 152.1, 139.0, 131.3 (q, $^2J_{C-F}$=32 Hz), 130.9, 129.5, 128.5, 127.3, 128.4 (q, $^1J_{C-F}$=277 Hz), 122.8, 119.9 (q, $^3J_{C-F}$=3.8 Hz), 116.3 (q, $^3J_{C-F}$=3.9 Hz), 17.6; HRMS (ESI) Calcd for C$_{15}$H$_{12}$F$_3$N [M+H]$^+$ 264.1000, found 264.1008.

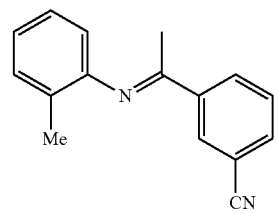 [SMILES: C/C(=N\c1ccccc1C)c1cccc(C#N)c1]

(E)-3-(1-(o-Tolylimino)ethyl)benzonitrile (1ac)

Yellow solid (82% yield); Mp=89-90° C.; $^1$H NMR (400 MHz, CDCl$_3$): δ 8.26 (s, 1H), 8.24 (d, J=8.0 Hz, 1H), 7.75 (d, J=7.7 Hz, 1H), 7.58 (t, J=7.8 Hz, 1H), 7.24-7.18 (m, 2H), 7.04 (td, J=7.5, 0.8 Hz, 1H), 6.62 (d, J=7.6 Hz, 1H), 2.19 (s, 3H), 2.10 (s, 3H); $^{13}$C NMR (100 MHz, CDCl$_3$): δ 162.8, 149.4, 140.4, 133.5, 131.3, 131.0, 130.5, 129.3, 127.1, 126.5, 123.8, 118.6, 118.1, 112.8, 17.8, 17.3; HRMS (ESI) Calcd for C$_{16}$H$_{14}$N$_2$ [M+H]$^+$ 235.1235, found 235.1233.

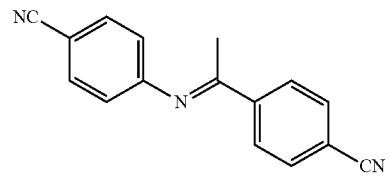 [SMILES: C/C(=N\c1ccc(C#N)cc1)c1ccc(C#N)cc1]

(E)-4-((1-(4-cyanophenyl)ethylidene)amino)benzonitrile (1ad)

Yellow solid (75% yield); Mp=176-177° C.; $^1$H NMR (400 MHz, CDCl$_3$) δ 8.10 (d, J=8.6 Hz, 2H), 7.76 (d, J=8.7 Hz, 2H), 7.67 (d, J=8.2 Hz, 2H), 6.86 (d, J=8.7 Hz, 2H), 2.26 (s, 3H); $^{13}$C NMR (100 MHz, CDCl$_3$) δ 164.7, 154.8, 142.1, 133.3, 132.2, 127.8, 119.6, 119.0, 118.2, 114.4, 107.2, 17.7; HRMS (ESI) Calcd for C$_{16}$H$_{11}$N$_3$ [M+H]$^+$ 246.1031, found 246.1026.

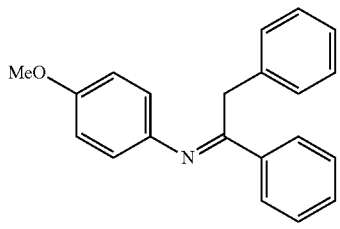 [SMILES: COc1ccc(/N=C(\Cc2ccccc2)c2ccccc2)cc1]

(E)-N-(1,2-Diphenylethylidene)-4-methoxyaniline (1af)

Yellow solid (65% yield); Mp=122-123° C.; $^1$H NMR (400 MHz, CDCl$_3$): δ 7.95-7.93 (m, 2H), 7.40-7.35 (m, 3H), 7.26-7.21 (m, 2H), 7.18-7.14 (m, 1H), 7.10 (d, J=7.6 Hz, 2H), 6.89-6.86 (m, 2H), 6.82-6.80 (m, 2H), 4.13 (s, 2H), 3.80 (s, 3H); $^{13}$C NMR (100 MHz, CDCl$_3$): δ 166.5, 156.1, 144.3, 138.6, 137.3, 130.2, 128.7, 128.4, 128.3, 128.0, 126.2, 120.5, 114.3, 55.5, 36.1; HRMS (ESI) Calcd for C$_{21}$H$_{19}$NO [M+H]$^+$ 302.1545, found 302.1548.

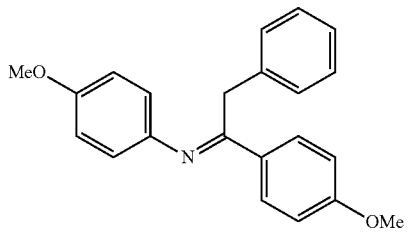 [SMILES: COc1ccc(/N=C(\Cc2ccccc2)c2ccc(OC)cc2)cc1]

(E)-4-Methoxy-N-(1-(4-methoxyphenyl)-2-phenyl-ethylidene)aniline (1ag)

Yellow solid (50% yield); Mp=114-115° C.; $^1$H NMR (400 MHz, CDCl$_3$): δ 7.88 (d, J=8.0 Hz, 2H), 7.27-7.21 (com, 2H), 7.14 (d, J=7.0 Hz, 1H), 7.08 (d, J=7.0 Hz, 2H), 6.86-6.83 (com, 4H), 6.77-6.65 (com, 2H), 4.07 (s, 2H), 3.78 (s, 3H), 3.76 (s, 3H); $^{13}$C NMR (100 MHz, CDCl$_3$): δ 165.4, 161.2, 155.9, 144.4, 137.6, 131.1, 129.6, 128.6, 128.3, 126.1, 120.5, 114.2, 113.6, 55.4, 55.2, 35.8; HRMS (ESI) Calcd for C$_{22}$H$_{21}$NO$_2$ [M+H]$^+$ 332.1651, found 332.1649.

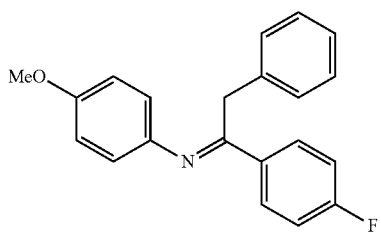 [SMILES: COc1ccc(/N=C(\Cc2ccccc2)c2ccc(F)cc2)cc1]

(E)-N-(1-(4-Fluorophenyl)-2-phenylethylidene)-4-methoxyaniline (1ah)

The title compound contained small amounts of impurities (<10%; see the attached $^1$H spectrum) that could not be removed by chromatographic separation. Without further purification, it was used for the cyclization reaction; $^1$H NMR (400 MHz, CDCl$_3$): δ 7.89 (dd, J=9.0, 5.7 Hz, 2H), 7.23 (d, J=7.5 Hz, 2H), 7.16 (d, J=7.0 Hz, 1H), 7.05-6.99 (com, 4H), 6.86 (d, J=9.0 Hz, 2H), 6.77 (d, J=9 Hz, 2H), 5.08 (s, 2H), 3.78 (s, 3H).

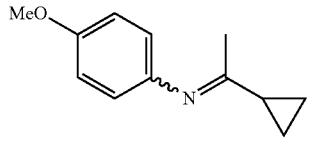

N-(1-cyclopropylethylidene)-4-methoxyaniline (1ai)

Yellow oil (76% yield); Approx. 3.1:1 mixture of E and Z isomers; $^1$H NMR (400 MHz, CDCl$_3$): δ 6.86-6.59 (m, 4H for both isomers), 3.77 (s, 3H), 3.76 (s, 3H), 1.79 (s, 3H), 1.72 (s, 3H), 0.97-0.70 (m, 5H for both isomers); $^{13}$C NMR (100 MHz, CDCl$_3$): δ 172.6, 172.5, 155.6, 155.5, 144.8, 144.3, 121.2, 120.8, 114.1, 114.1, 55.7, 55.4, 20.5, 20.2, 18.0, 14.8, 7.8, 6.8; HRMS (ESI) Calcd for C$_{12}$H$_{15}$NO [M+H]$^+$ 190.1232, found 190.1237.

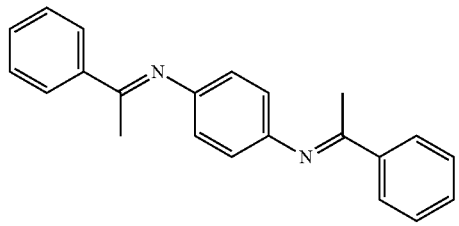 [SMILES: C/C(=N\c1ccc(/N=C(\C)c2ccccc2)cc1)c1ccccc1]

(N$^1$E,N$^4$E)-N$^1$,N$^4$-Bis(1-phenylethylidene)benzene-1,4-diamine (1al)

Yellow solid (80% yield); Mp=213-214° C.; $^1$H NMR (400 MHz, CDCl$_3$): δ 7.99-7.97 (com, 4H), 7.45-7.42 (com, 6H), 6.81 (s, 4H), 2.28 (s, 6H); $^{13}$C NMR (100 MHz, CDCl$_3$): δ 165.6, 147.1, 139.5, 130.3, 128.3, 127.1, 120.1, 17.3; HRMS (ESI) Calcd for C$_{22}$H$_{20}$N$_2$ [M+H]$^+$ 313.1705, found 313.1702.

(N$^1$E,N$^3$E)-N$^1$,N$^3$-bis(1-phenylethylidene)benzene-1,3-diamine (1am)

Pale yellow solid (70% yield); Mp=113-114° C.; $^1$H NMR (400 MHz, CDCl$_3$): δ 7.97 (com, 4H), 7.45-7.41 (com, 6H), 7.32 (t, J=7.6 Hz, 1H), 6.53 (dd, J=5.9, 1.8 Hz, 2H), 6.24 (t, J=1.8 Hz, 1H), 2.23, (s, 6H); $^{13}$C NMR (100 MHz, CDCl$_3$): δ 165.6, 152.5, 139.4, 130.4, 129.5, 128.3, 127.1, 114.2, 109.9, 17.4; HRMS (ESI) Calcd for C$_{22}$H$_{20}$N$_2$ [M+H]$^+$ 313.1705, found 313.1702.

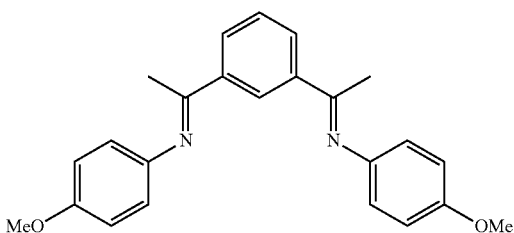 [SMILES: COc1ccc(/N=C(\C)c2cccc(/C(C)=N/c3ccc(OC)cc3)c2)cc1]

(N,N'E,N,N'E)-N,N'-(1,3-Phenylenebis(ethan-1-yl-1-ylidene))bis(4-methoxyaniline) (1an)

Yellow solid (70% yield); Mp=183-184° C.; $^1$H NMR (400 MHz, CDCl$_3$): δ 8.54 (t, J=1.7 Hz, 1H), 8.04 (dd, J=7.6, 2 Hz, 2H), 7.51 (t, J=7.6 Hz, 1H), 6.93-6.90 (m, 4H), 6.79-6.75 (m, 4H), 3.82 (s, 6H), 2.30 (m, 6H); $^{13}$C NMR (100 MHz, CDCl$_3$): δ 165.6, 155.9, 144.6, 139.9, 128.9, 128.3, 125.8, 120.7, 114.2, 55.4; HRMS (ESI) Calcd for C$_{24}$H$_{24}$N$_2$O$_2$ [M+H]$^+$ 373.1916, found 373.1916.

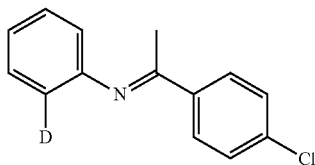 [SMILES: [2H]c1ccccc1/N=C(\C)c1ccc(Cl)cc1]

2-Deuterio-(E)-N-(1-(4-chlorophenyl)ethylidene)aniline: (1aq-d)

Prepared from 2-deuterio-aniline (deuterium incorporation >95%) (Würtz, S.; Rakshit, S.; Neumann, J. J.; Dröge, T; Glorius, F. *Angew. Chem. Int. Ed.* 2008, 47, 7230) and 4'-chloroacetophenone; Yellow solid (70% yield); Mp=93-94° C.; $^1$H NMR (400 MHz, CDCl$_3$): δ 7.91 (d, J=8.6 Hz, 2H), 7.41 (d, J=8.6 Hz, 2H), 7.38-7.34 (m, 2H), 7.10 (td, J=7.5, 1.0 Hz, 1H), 6.78 (dd, J=8.1, 0.8 Hz, 1H), 2.21 (s, 3H); $^{13}$C NMR (100 MHz, CDCl$_3$): δ 164.3, 151.3, 137.9 136.6, 129.0, 128.9, 128.6, 123.4, 119.3, 17.3 (two signals could not be observed because of $^{13}$C-$^2$H coupling); HRMS (ESI) Calcd for C$_{14}$H$_{11}$ClND [M+H]$^+$ 231.0799, found 231.0792.

Pentadeuterio-Aniline

Pentadeuterio-aniline was prepared by copper-catalyzed amination of bromobenzene-d$_6$ with aqueous ammonia according to the method reported by Wolf et al. (Xu, H.; Wolf C. *Chem. Commun.* 2009, 3035).

A 150 mL of Schlenk tube equipped with a stirrer bar was charged with bromobenzene-d$_5$ (20 mmol), Cu$_2$O (5 mol %), 15 mL of ammonium hydroxide solution (~25% NH$_3$ in H$_2$O, 10 equiv), and 15 mL of N-methylpyrrolidinone (NMP). The tube was sealed with a Teflon screw cap, and then stirred at 80° C. for 15 h. Upon completion, the reaction mixture was cooled to room temperature and extracted with diethyl ethyl and dried over Na$_2$SO$_4$, filtered, concentrated under reduced pressure. The residue was directly used for the imine synthesis without further purification.

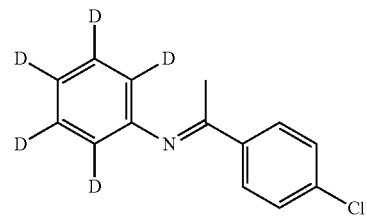 [SMILES: [2H]c1c([2H])c([2H])c(/N=C(\C)c2ccc(Cl)cc2)c([2H])c1[2H]]

2,3,4,5,6-Pentadeuterio-(E)-N-(1-(4-chlorophenyl)ethylidene)aniline: (1aq-d$_5$)

Prepared from pentadeuterio-aniline and 4'-chloroacetophenone; Yellow solid (58% yield); Mp=92-93° C.; $^1$H NMR (400 MHz, CDCl$_3$): δ 7.94-7.90 (m, 2H), 7.44-7.40 (m, 2H), 2.22 (s, 3H); $^{13}$C NMR (100 MHz, CDCl$_3$): δ 164.3, 151.2, 137.9, 136.6 128.6, 17.3 (except deuterated carbons); HRMS (ESI) Calcd for C$_{14}$H$_7$D$_5$ClN [M+H]$^+$ 235.1050, found 235.1046.

Example 3

Catalytic Oxidative Cyclization of N-Aryl Imines

TABLE 1

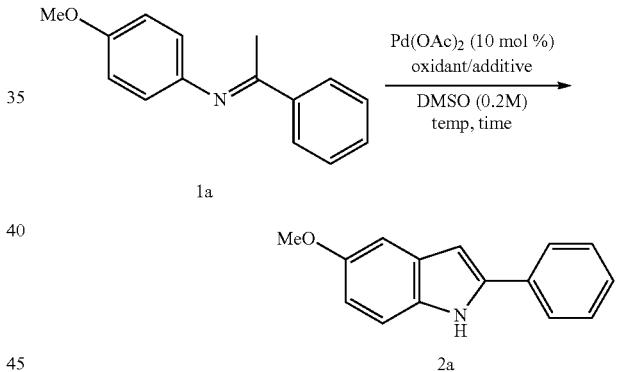

| Entry | Oxidant/additive/other changes | Temp (°C.) | Time (h) | Yield (%)$^b$ |
|---|---|---|---|---|
| 1 | O$_2$ (1 atm) | 40 | 16 | 27 |
| 2 | O$_2$ (4 atm) | 40 | 16 | 39 |
| 3 | O$_2$ (1 atm)/Bu$_4$NCl (1 equiv) | 40 | 16 | 24 |
| 4 | O$_2$ (1 atm)/Bu$_4$NBr (1 equiv) | 40 | 16 | 48 |
| 5 | O$_2$ (1 atm)/Bu$_4$NI (1 equiv) | 40 | 16 | 31 |
| 6 | O$_2$ (1 atm)/Bu$_4$NOAc (1 equiv) | 40 | 16 | 22 |
| 7 | O$_2$ (1 atm)/LiBr (2 equiv) | 40 | 16 | 45 |
| 8 | O$_2$ (1 atm)/MS 4A | 40 | 16 | 18 |
| 9 | O$_2$ (1 atm)/HOAc (2 equiv) | 40 | 16 | 17 |
| 10 | O$_2$ (1 atm)/NaOAc (1 equiv) | 40 | 16 | 15 |
| 11 | O$_2$ (1 atm)/3-nitropyridine (20 mol %) | 40 | 16 | 11 |
| 12 | O$_2$ (1 atm)/Bu$_4$NBr (2 equiv) | 25 | 16 | 76$^c$ |
| 13 | O$_2$ (1 atm)/Bu$_4$NBr (2 equiv) | 60 | 16 | 89$^c$ |
| 14 | open air/Bu$_4$NBr (2 equiv) | 60 | 16 | 67 |
| 15 | Cu(OAc)$_2$ (3 equiv) | 40 | 12 | 93$^c$ |
| 16 | CuCl$_2$ (3 equiv) | 40 | 12 | 0 |
| 17 | AgOAc (3 equiv) | 40 | 12 | 0 |
| 18 | BzOOtBu (3 equiv) | 40 | 12 | 23 |
| 19 | BQ (2 equiv) | 40 | 12 | 8 |
| 20 | tBuOOtBu (2 equiv) | 40 | 12 | 5 |
| 21 | PhI(OAc)$_2$ (3 equiv) | 40 | 12 | 0 |
| 22 | DDQ (2 equiv) | 40 | 12 | 0 |

TABLE 1-continued

Screening of Reaction Conditions[a]

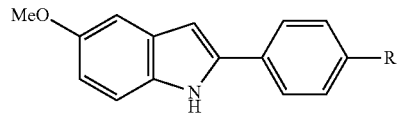

| Entry | Oxidant/additive/other changes | Temp (°C.) | Time (h) | Yield (%)[b] |
|---|---|---|---|---|
| 23 | Cu(OAc)$_2$ (3 equiv)/DMF instead of DMSO | 40 | 12 | 0 |
| 24 | Cu(OAc)$_2$ (3 equiv)/dioxane instead of DMSO | 40 | 12 | 0 |
| 25 | Cu(OAc)$_2$ (3 equiv)/MeCN instead of DMSO | 40 | 12 | 0 |
| 26[d] | Pd(OAc)$_2$ (10 mol %), Cu(OAc)$_2$ (3 equiv), K$_2$CO$_3$ (3 equiv) DMF (0.08M), 80° C. | | | 0 |
| 27[d] | CuI (5 mol %), phen (17.5 mol %), Li$_2$CO$_3$ (2 equiv) DMF, 100° C., air | | | 0 |
| 28[d] | PhI(OAc)$_2$ (1.3 equiv), DCE, 60° C. | | | 0 |
| 29[d] | FeCl$_3$ (10 mol %), Cu(OAc)2•CuCl$_2$ (3 equiv), K$_2$CO$_3$ (3 equiv) DMF, 120° C. | | | 0 |

[a]Reaction was performed on a 0.2 mmol scale unless otherwise noted.
[b]Determined by GC using n-tridecane as an internal standard.
[c]Isolated yield.
[d]Reaction conditions were adopted from literature (Yu, W., supra; Wiirtz, S, supra; Bernini, R., Fabrizi, G., Sferrazza, A., Cacchi, S. Angew. Chem., Int. Ed. 2009, 48, 8078; Guan, Z.-H., Yan, Z.-Y., Ren, Z.-H., Liva, X.-Y., Liang, Y.-M. Chem Commun 2010, 46, 2823).

Scheme 1: Indole Synthesis from N-Aryl Imines: Comparison of Aerobic and Copper(II)-Mediated Systems[a]

(First % and second % values indicated against each compound denote isolated yields obtained under Condition A and B respectively).

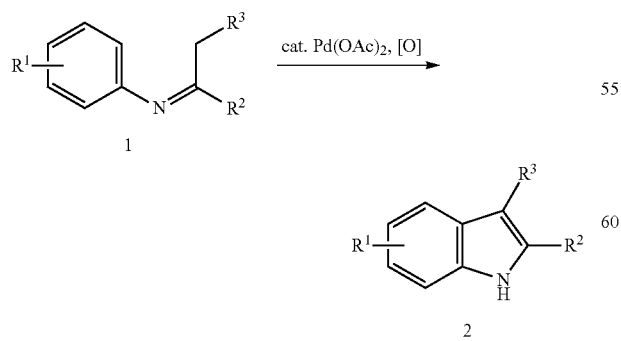

Conditions A: Pd(OAc)$_2$ (10 mol %), Bu$_4$NBr (2 equiv), O$_2$ (1 atm), DMSO, 60° C., 24 h
Conditions B: Pd(OAc)$_2$ (10 mol %), Cu(OAc)$_2$ (3 equiv), DMSO, 40° C., 5-24 h

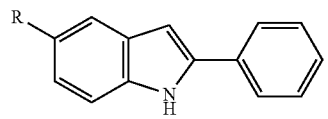

2a (R = H), 89%, 93%
2b (R = NO$_2$), 92%, 82%
2c (R = CN), 91%, 93%
2d (R = CONR′$_2$),[b] NA,[c] 81%
2e (R = CF$_3$), 86%, 86%
2f (R = Cl), 90%, 88%
2g (R = Br), 77%, 71%
2h (R = Me), 86%, 78%
2i (R = OMe), 82%, 75%

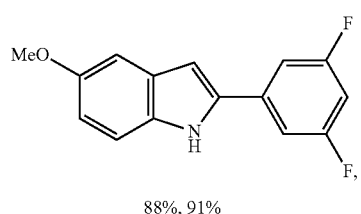

2j (R = H), 87%, 85%
2k (R = NO$_2$), 58%, 55%
2l (R = CF$_3$), 81%, 79%
2m (R = CO$_2$Et), 82%, 91%
2n (R = Cl), 88%, 83%
2o (R = Br), 93%, 91%
2p (R = Me), 92%, 92%
2q (R = NHAc), 64%, 64%

2r

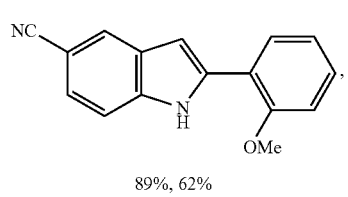

88%, 91%

2s

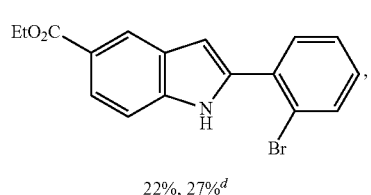

89%, 62%

2t

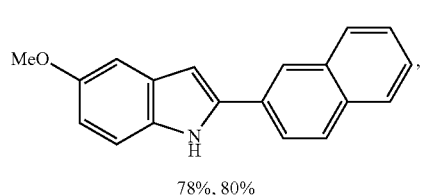

22%, 27%[d]

2u

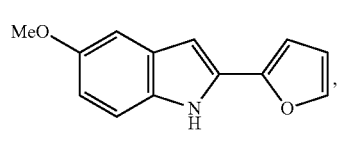

78%, 80%

2v

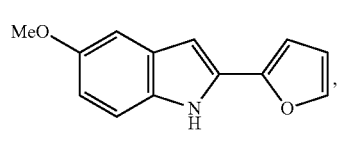

76%, 62%

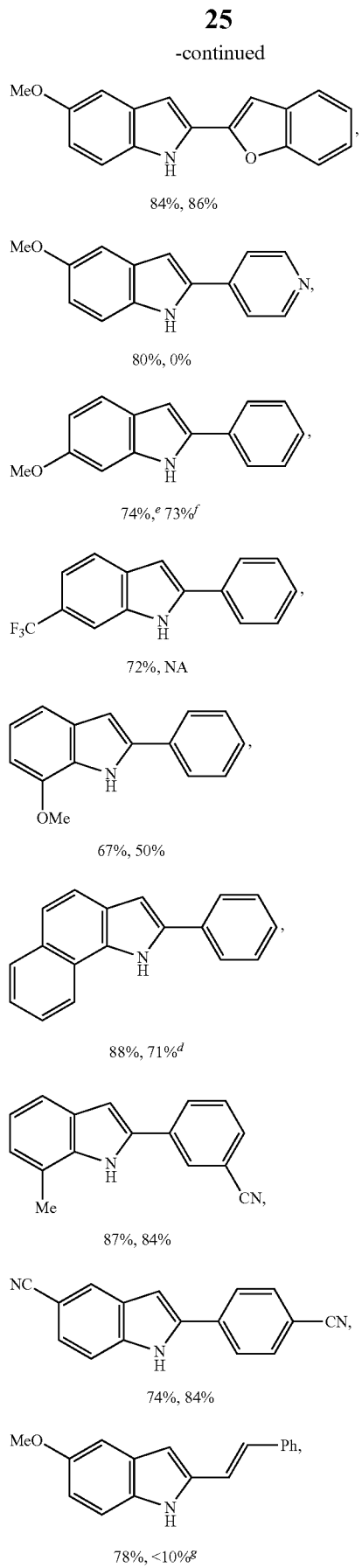

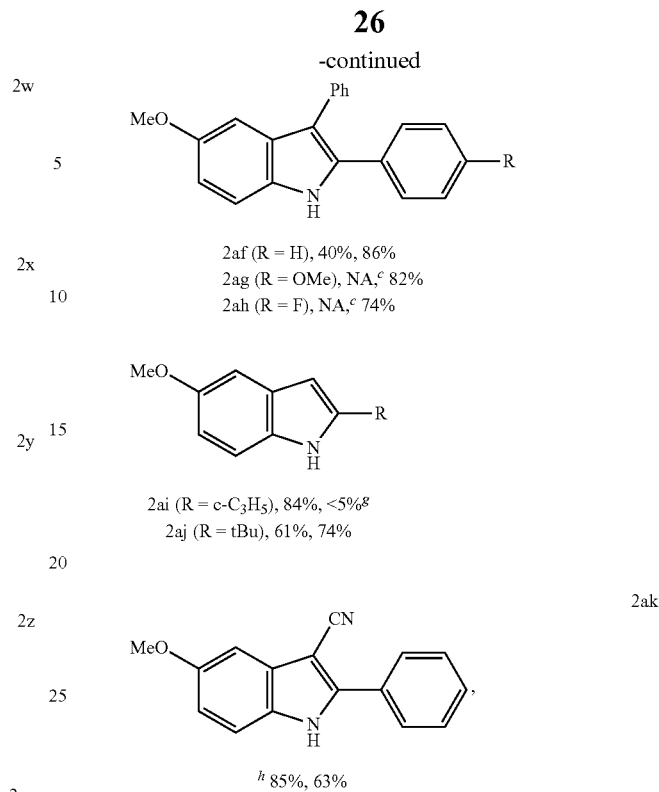

2af (R = H), 40%, 86%
2ag (R = OMe), NA,[c] 82%
2ah (R = F), NA,[c] 74%

2ai (R = c-C$_3$H$_5$), 84%, <5%[g]
2aj (R = tBu), 61%, 74%

[h] 85%, 63%

[a] Reaction was performed on a 0.2 mmol scale. [b] NR$_2$' = morpholino. [c] NA = Not examined. [d] 20 mol % of Pd(OAc)$_2$ was used. [e] A regioisomeric product was obtained in 7% yield. [f] A regioisomeric product was obtained in 5% yield. [g] Estimated by GC analysis. [h] The starting material was in the form of enamine.

Scheme 2: Two-fold Oxidative Cyclizations: Comparison of Aerobic and Copper(II)-Mediated Systems[a]

(First % and second % values indicated against each compound denote isolated yields obtained under Condition A and B respectively).

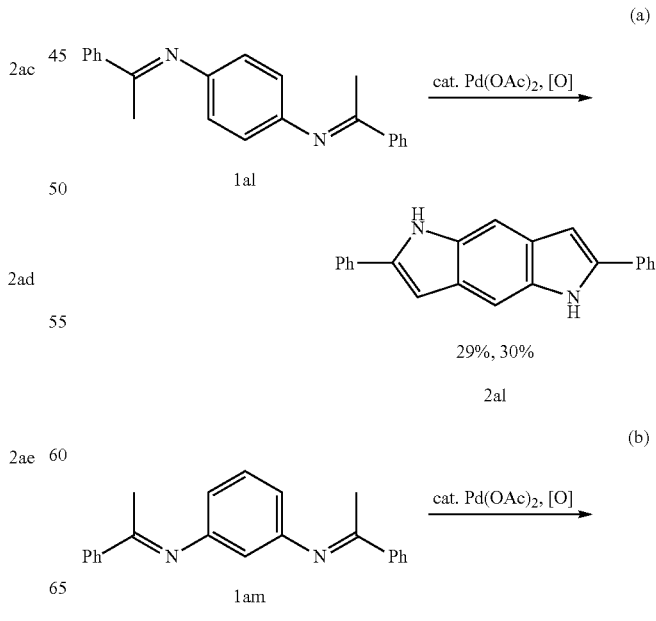

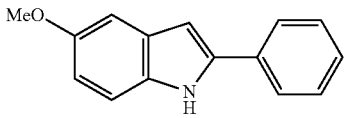 [SMILES: COc1ccc2[nH]c(-c3ccccc3)cc2c1]

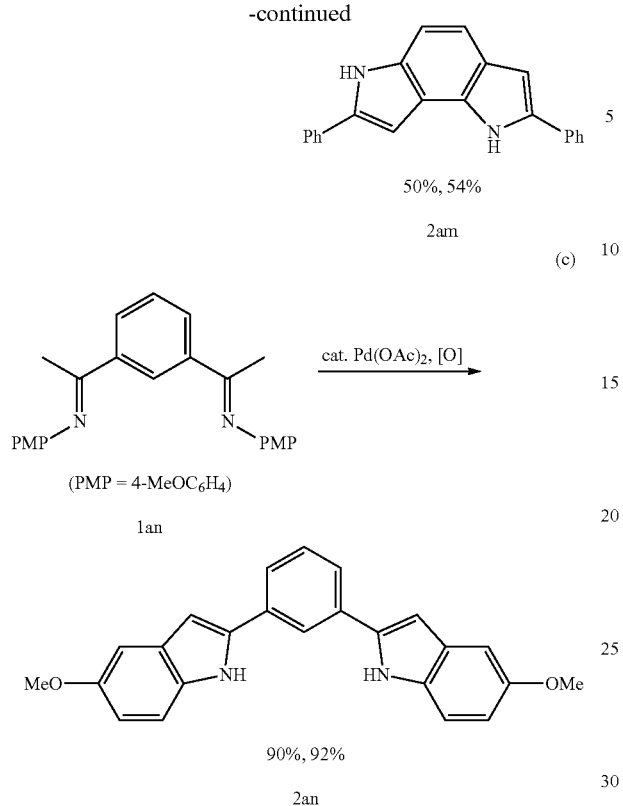

90%, 92%

2an

Conditions A: Pd(OAc)₂ (20 mol %), Bu₄NBr (4 equiv), O₂ (1 atm), DMSO, 60° C., 24 h
Conditions B: Pd(OAc)₂ (20 mol %), Cu(OAc)₂ (4-6 equiv), DMSO, 40° C., 24 h

[a]Reaction was performed on a 0.2 mmol scale.

Example 4

General Procedure for Pd/Bu₄NBr/O₂ System

A Schlenk tube equipped with a stirrer bar was charged with N-aryl imine (0.2 mmol), Pd(OAc)₂ (4.5 mg, 0.02 mmol, 10 mol %) and Bu₄NBr (129 mg, 0.4 mmol), followed by addition of DMSO (1 mL). The Schlenk tube was quickly evacuated, closed under vacuum, and then refilled with oxygen using an oxygen balloon. The resulting mixture was stirred at 60° C. for 24 h. Upon cooling to room temperature, the reaction mixture was diluted with 5 mL of ethyl acetate, followed by filtration through a pad of silica gel. The filtrate was concentrated under reduced pressure, and the residue was purified by flash chromatography on silica gel to afford the indole product.

Example 5

General Procedure for Pd/Cu System

A Schlenk tube equipped with a stirrer bar was charged with N-aryl imine (0.2 mmol), Pd(OAc)₂ (4.5 mg, 0.02 mmol, 10 mol %) and Cu(OAc)₂ (109 mg, 0.6 mmol, 3 equiv). The Schlenk tube was evacuated and refilled with N₂ for three times, followed by addition of DMSO (1 mL). The Schlenk tube was sealed with a Teflon screwcap and then the reaction mixture was stirred at 40° C. for 12 h. Upon cooling to room temperature, the reaction mixture was diluted with 5 mL of ethyl acetate, followed by filtration through a pad of silica gel. The filtrate was washed with water (10 mL), dried over Na₂SO₄, and then concentrated under reduced pressure. Purification of the residue by flash chromatography on silica gel was purified afforded the indole product.

5-Methoxy-2-phenyl-1H-indole (2a)

(Deprez, N. R.; Kalyani, D.; Krause, A.; Sanford, M S. *J. Am. Chem. Soc.* 2006, 128, 4972).

10 mmol-Scale Reaction (Eq 1):

A 100 mL round-bottom flask equipped with a stirrer bar was charged with (E)-4-methoxy-N-(1-phenylethylidene) aniline (10 mmol, 2.25 g), Pd(OAc)₂ (0.22 g, 1 mmol, 10 mol %) and Bu₄NBr (6.45 g, 20 mmol, 2 equiv), followed by addition of DMSO (50 mL). The flask was quickly evacuated, closed under vacuum, and then refilled with oxygen using an oxygen balloon. The resulting mixture was stirred at 60° C. for 24 h. Upon cooling to room temperature, the reaction mixture was diluted with 25 mL of ethyl acetate, followed by filtration through a pad of silica gel. The filtrate was concentrated under vacuum, and the residue was purified on silica gel to afford the title compound as an off-white solid (1.87 g, 84%).

50 mmol-Scale Reaction (Table 2, Entry 9):

A 500 mL round-bottom flask equipped with a stirrer bar was charged with (E)-4-methoxy-N-(1-phenylethylidene) aniline (50 mmol, 11.3 g), Pd(OAc)₂ (0.56 g, 2.5 mmol, 5 mol %) and Cu(OAc)₂ (18.2 g, 100 mmol, 2 equiv). The flask was evacuated and refilled with N₂ for three times, followed by addition of DMSO (250 mL). The flask was sealed with a glass stopper and then the reaction mixture was stirred at 40° C. for 48 h. Upon cooling to room temperature, the reaction mixture was diluted with 150 mL of ethyl acetate and filtered through a pad of silica gel using 100 mL of ethyl acetate as additional eluent. The filtrate was washed with water (3×250 mL), dried over Na₂SO₄, and concentrated under reduced pressure. The residue was purified by recrystallization (EtOAc/hexane) to afford the title compound as an off-white solid (9.7 g, 87%). The product showed the same degree of analytical purity compared with that obtained by a small-scale reaction.

Mp=169-170° C.; $^1$H NMR (400 MHz, CDCl₃): δ 8.26 (brs, 1H), 7.66-7.64 (m, 2H), 7.44 (t, J=7.2 Hz, 2H), 7.35 (t, J=7.4 Hz, 1H), 7.27 (d, J=8.6 Hz, 1H), 7.12 (d, J=2.3 Hz, 1H), 6.90 (dd, J=8.7, 2.4 Hz, 1H), 6.77 (d, J=1.9 Hz, 1H), 3.89 (s, 3H); $^{13}$C NMR (100 MHz, CDCl₃): δ 154.5, 138.6, 132.4, 132.0, 129.7, 129.0, 127.7, 125.1, 112.6, 111.6, 102.3, 99.8, 55.8; HRMS (ESI) Calcd for C₁₅H₁₃ON [M+H]⁺ 224.1075, found 224.1069. The $^1$H and $^{13}$C NMR spectral data are in good agreement with the literature data (Shen, M; Leslie, B. E.; Driver, T G. *Angew. Chem. Int. Ed.* 2008, 47, 5056).

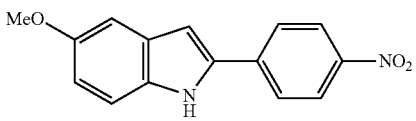 [SMILES: COc1ccc2[nH]c(-c3ccc([N+](=O)[O-])cc3)cc2c1]

5-Methoxy-2-(4-nitrophenyl)-1H-indole (2b)

Orange solid (92% yield, eluent=hexane/EtOAc (85:15)); Mp=200-201° C.; $^1$H NMR (400 MHz, acetone-$d_6$): δ 10.8 (brs, 1H), 8.29 (d, J=8.7 Hz, 2H), 8.06 (d, J=8.6 Hz, 2H), 7.35 (d, J=9.0 Hz, 1H), 7.10 (d, J=3.9 Hz, 2H), 6.86 (dd, J=8.7, 1.9 Hz, 1H), 3.82 (s, 3H); $^{13}$C NMR (100 MHz, acetone-$d_6$): δ 154.7, 146.3, 138.9, 135.8, 133.5, 129.5, 125.2, 124.2, 114.2, 112.3, 102.5, 101.8, 55.9; HRMS (ESI) Calcd for $C_{15}H_{12}N_2O_3$ [M+H]$^+$ 269.0926, found 269.0923.

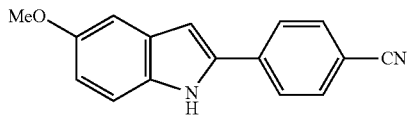 [SMILES: COc1ccc2[nH]c(-c3ccc(C#N)cc3)cc2c1]

4-(5-Methoxy-1H-indol-2-yl)benzonitrile (2c)

Pale yellow solid (91% yield, eluent=hexane/EtOAc (85:15)); Mp=195-196° C.; $^1$H NMR (400 MHz, CDCl$_3$): δ 8.33 (brs, 1H), 7.73-7.68 (m, 4H), 7.31 (d, J=8.8 Hz, 1H), 7.09 (d, J=2.2 Hz, 1H), 6.92 (dd, J=8.8, 2.4 Hz, 1H), 6.88 (J=1.3 Hz, 1H), 3.87 (s, 3H); $^{13}$C NMR (100 MHz, CDCl$_3$): δ 154.8, 136.6, 136.1, 132.8, 132.7, 129.4, 125.1, 118.9, 114.4, 112.0, 110.5, 102.4, 102.3, 55.8; HRMS (ESI) Calcd for $C_{16}H_{12}N_2O$ [M+H]$^+$ 249.1028, found 249.1031.

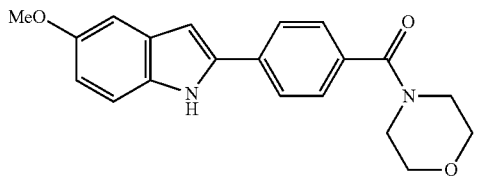 [SMILES: COc1ccc2[nH]c(-c3ccc(C(=O)N4CCOCC4)cc3)cc2c1]

(4-(5-Methoxy-1H-indol-2-yl)phenyl)(morpholino)methanone (2d)

The reaction was performed with the Pd/Cu system; Yellow solid (81% yield, eluent=hexane/acetone (60:40)); Mp=223-224° C.; NMR (400 MHz, CDCl$_3$): δ 8.79 (brs, 1H), 7.63 (d, J=8.2 Hz, 2H), 7.41 (d, J=8.2 Hz, 2H), 7.31 (d, J=8.8 Hz, 1H), 7.08 (d, J=2.2 Hz, 1H), 6.87 (dd, J=8.7, 2.3 Hz, 1H), 6.77 (d, J=1.4 Hz, 1H), 3.87 (s, 3H), 3.72-3.54 (m, 8H); $^{13}$C NMR (100 MHz, CDCl$_3$): δ 170.2, 154.6, 137.5, 134.2, 133.8, 132.4, 129.5, 128.0, 125.1, 113.2, 111.9, 102.2, 100.7, 66.9, 55.8 (signals of the carbon atoms bonded to the oxygen atom of the morpholine ring were not observed); HRMS (ESI) Calcd for $C_{20}H_{20}N_2O_3$ [M+H]$^+$ 337.1552, found 337.1549.

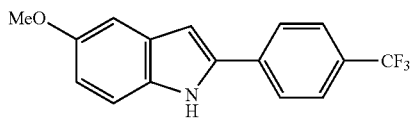 [SMILES: COc1ccc2[nH]c(-c3ccc(C(F)(F)F)cc3)cc2c1]

5-Methoxy-2-(4-(trifluoromethyl)phenyl)-1H-indole (2e)

White solid (86% yield, eluent=hexane/EtOAc (92:8)); Mp=196-197° C.; $^1$H NMR (400 MHz, CDCl$_3$): δ 8.26 (brs, 1H), 7.68 (d, J=8.4 Hz, 2H), 7.64 (d, J=8.5 Hz, 2H), 7.27 (d, J=8.8 Hz, 1H), 7.08 (d, J=2.3 Hz, 1H), 6.89 (dd, J=8.8, 2.4 Hz, 1H), 6.82 (d, J=1.4 Hz, 1H), 3.86 (s, 3H); $^{13}$C NMR (100 MHz, CDCl$_3$): δ 154.7, 136.8, 135.7, 132.4, 129.5, 129.3 (q, $^2J_{C-F}$=32.3 Hz), 126.0 (q, $^3J_{C-F}$=3.8 Hz), 124.1 (q, $^1J_{C-F}$=271.9 Hz), 125.0, 113.7, 111.9, 102.4, 101.5, 55.8; HRMS (ESI) Calcd for $C_{16}H_{12}F_3ON$ [M+H]$^+$ 292.0949, found 292.0947. The $^1$H and $^{13}$C NMR spectral data are in good agreement with the literature data (Shen, M, supra).

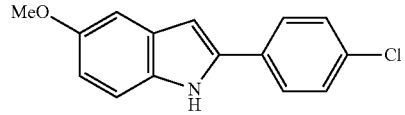 [SMILES: COc1ccc2[nH]c(-c3ccc(Br)cc3)cc2c1]

5-Methoxy-2-(4-chlorophenyl)-1H-indole (2f)

White solid (90% yield, eluent=hexane/EtOAc (92:8)); Mp=193-194° C.; $^1$H NMR (400 MHz, CDCl$_3$): δ 8.17 (brs, 1H), 7.53 (d, J=8.5 Hz, 2H), 7.38 (d, J=8.5 Hz, 2H), 7.26 (d, J=8.6 Hz, 1H), 7.07 (d, J=2.1 Hz, 1H), 6.86 (dd, J=8.8, 2.4 Hz, 1H), 6.72 (d, J=1.3 Hz, 1H), 3.85 (s, 3H); $^{13}$C NMR (100 MHz, CDCl$_3$): δ 154.6, 137.4, 133.4, 132.1, 130.9, 129.7, 129.2, 126.2, 113.0, 111.7, 102.3, 100.3, 55.8; HRMS (ESI) Calcd for $C_{15}H_{12}ONCl$ [M+H]$^+$ 258.0686, found 258.0683. The $^1$H and $^{13}$C NMR spectral data are in good agreement with the literature data (Bartoli, G.; Palmieri, G.; Petrini, M.; Bosco, M.; Dalpozzo, R. *Tetrahedron* 1990, 46, 1379).

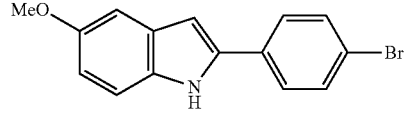 [SMILES: COc1ccc2[nH]c(-c3ccc(C)cc3)cc2c1]

5-Methoxy-2-(4-bromophenyl)-1H-indole (2g)

White solid (77% yield, eluent=hexane/EtOAc (92:8)); Mp=201-202° C.; $^1$H NMR (400 MHz, CDCl$_3$): δ 8.18 (brs, 1H), 7.56 (d, J=8.6 Hz, 2H), 7.50 (d, J=8.7 Hz, 2H), 7.30 (d, J=8.8 Hz, 1H), 7.08 (d, J=2.3 Hz, 1H), 6.87 (dd, J=8.8, 2.4 Hz, 1H), 6.75 (d, J=1.5 Hz, 1H), 3.86 (s, 3H); $^{13}$C NMR (100 MHz, CDCl$_3$): δ 154.6, 137.4, 132.1, 131.4, 129.6, 126.5, 121.4, 113.1 (two signals are overlapped), 111.7, 102.3, 100.4, 55.8; HRMS (ESI) Calcd for $C_{15}H_{12}ONBr$ [M+H]$^+$ 302.0181, found 302.0187.

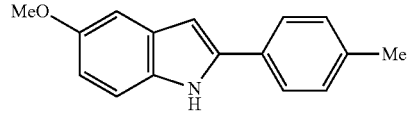

5-Methoxy-2-(p-tolyl)-1H-indole (2h)

White solid (86% yield, eluent=hexane/EtOAc (92:8)); Mp=186-187° C.; $^1$H NMR (400 MHz, CDCl$_3$): δ 8.17 (brs, 1H), 7.51 (d, J=8.2 Hz, 2H), 7.23-7.20 (m, 3H), 7.07 (d, J=2.3 Hz, 1H), 6.83 (dd, J=8.8, 2.5 Hz, 1H), 6.69 (d, J=1.4 Hz, 1H), 3.84 (s, 3H), 2.37 (s, 3H); $^{13}$C NMR (100 MHz, CDCl$_3$): δ 154.5, 138.9, 137.6, 131.9, 129.8, 129.7, 129.6, 125.0, 112.4,

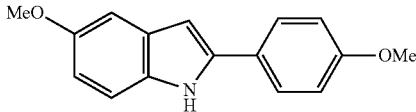 [SMILES: COc1ccc(-c2cc3cc(OC)ccc3[nH]2)cc1]

5-Methoxy-2-(4-methoxyphenyl)-1H-indole (2i)

White solid (82% yield, eluent hexane/EtOAc (90:10)); Mp=218-219° C.; $^1$H NMR (400 MHz, CDCl$_3$): δ 8.14 (brs, 1H), 7.57 (d, J=8.7 Hz, 2H), 7.26 (s, 1H), 7.07 (d, J=1.8 Hz, 1H), 6.97 (d, J=8.6 Hz, 2H), 6.83 (dd, J=8.7, 2.3 Hz, 1H), 6.65 (s, 1H), 3.86 (s, 3H), 3.85 (s, 3H); $^{13}$C NMR (100 MHz, CDCl$_3$): δ 159.3, 154.5, 138.7, 131.8, 129.9, 126.4, 125.3, 114.5, 112.0, 111.4, 102.2, 98.7, 55.9, 55.4; HRMS (ESI) Calcd for C$_{16}$H$_{15}$O$_2$N [M+H]$^+$ 254.1181, found 254.1188. The $^1$H and $^{13}$C NMR spectral data are in good agreement with the literature data (Geary, L. M; Hultin, P. G. *Org. Lett.* 2009, 11, 5478).

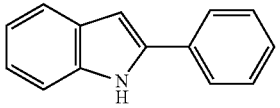

2-Phenyl-1H-indole (2j)

White solid (87% yield, eluent=hexane/EtOAc (92:8)); Mp=189-190° C.; NMR (400 MHz, CDCl$_3$): δ 8.29 (brs, 1H), 7.63 (t, J=6.6 Hz, 3H), 7.43 (t, J=7.9 Hz, 2H), 7.38 (d, J=7.9 Hz, 1H), 7.31 (t, J=7.5 Hz, 1H), 7.19 (td, J=7.1, 1.0 Hz, 1H), 7.12 (td, J=7.0, 0.7 Hz, 1H), 6.82 (d, J=1.3 Hz, 1H); $^{13}$C NMR (100 MHz, CDCl$_3$): 137.9, 136.8, 132.4, 129.3, 129.0, 127.7, 125.2, 122.3, 120.7, 120.3, 110.9, 100.0; HRMS (ESI) Calcd for C$_{14}$H$_{11}$N [M+H]$^+$ 194.0970, found 194.1974. The $^1$H and $^{13}$C NMR spectral data are in good agreement with the literature data (Shen, M, supra).

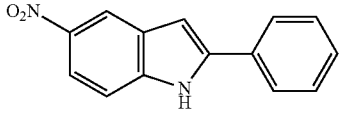

5-Nitro-2-phenyl-1H-indole (2k)

Yellow solid (58% yield, eluent=hexane/EtOAc (90:10)); Mp=199-200° C.; $^1$H NMR (400 MHz, CDCl$_3$): δ 8.76 (brs, 1H), 8.59 (d, J=2.1 Hz, 1H), 8.11 (dd, J=9.0, 2.3 Hz, 1H), 7.70 (d, J=8.1 Hz, 2H), 7.50 (t, J=7.8 Hz, 2H), 7.45-7.39 (m, 2H), 6.97 (d, J=1.4 Hz, 1H); $^{13}$C NMR (100 MHz, CDCl$_3$): δ 142.3, 141.1, 139.7, 131.1, 129.3, 128.8, 128.6, 125.4, 118.0, 117.7, 110.8, 101.7; HRMS (ESI) Calcd for C$_{14}$H$_{10}$N$_2$O$_2$ [M+H]$^+$ 239.0821, found 239.0829. The $^1$H and $^{13}$C NMR spectral data are in good agreement with the literature data (Lai, R.-Y.; Surekha, K.; Hayashi, A.; Ozawa, F.; Liu, Y.-H.; Peng, S.-M.; Liu, S.-T *Organometallics* 2007, 26, 1062).

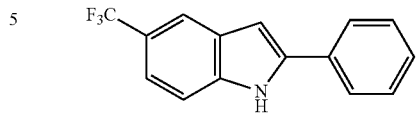

5-(Trifluoromethyl)-2-phenyl-1H-indole (2l)

White solid (81% yield, eluent=hexane/EtOAc (92:8)); Mp=153-154° C.; $^1$H NMR (400 MHz, CDCl$_3$): δ 8.46 (brs, 1H), 7.91 (s, 1H), 7.64 (d, J=7.4 Hz, 2H), 7.47-7.42 (m, 4H), 7.36 (t, J=7.3 Hz, 1H), 6.87 (d, J=1.9 Hz, 1H); $^{13}$C NMR (100 MHz, CDCl$_3$): δ 139.7, 138.1, 131.6, 129.2, 128.6, 128.4, 125.3 (q, $^1J_{C-F}$=272 Hz), 125.3, 122.7 (q, $^2J_{C-F}$=32.6 Hz), 119.0 (q, $^3J_{C-F}$=3.6 Hz), 118.3 (q, $^3J_{C-F}$=4.4 Hz), 111.1, 100.6; HRMS (ESI) Calcd for C$_{15}$H$_{10}$NF$_3$ [M+H]$^+$ 262.0844, found 262.0849. The $^1$H and $^{13}$C NMR spectral data are in good agreement with the literature data (Shen, M, supra).

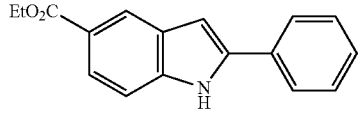

Ethyl 2-phenyl-1H-indole-5-carboxylate (2m)

White solid (82% yield, eluent=hexane/EtOAc (90:10)); Mp=184-185° C.; $^1$H NMR (400 MHz, CDCl$_3$): δ 8.76 (brs, 1H), 8.41 (s, 1H), 7.93 (dd, J=8.6, 1.4 Hz, 1H), 7.68 (d, J=7.5 Hz, 2H), 7.45 (t, J=7.5 Hz, 2H), 7.41 (d, J=8.6 Hz, 1H), 7.35 (t, J=7.4 Hz, 1H), 6.90 (d, J=1.2 Hz, 1H), 4.42 (q, J=7.1 Hz, 2H), 1.43 (t, J=7.2 Hz, 3H); $^{13}$C NMR (100 MHz, CDCl$_3$): δ 167.8, 139.4, 139.3, 131.8, 129.1, 128.8, 128.2, 125.3, 123.7, 123.5, 122.6, 110.6, 100.9, 60.7, 14.5; HRMS (ESI) Calcd for C$_{17}$H$_{15}$NO$_2$ [M+H]$^+$ 266.1181, found 266.1187.

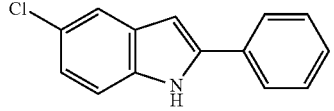 [SMILES: Clc1ccc2[nH]c(-c3ccccc3)cc2c1]

5-Chloro-2-phenyl-1H-indole (2n)

White solid (88% yield, eluent=hexane/EtOAc (92:8)); Mp=196-197° C.; $^1$H NMR (400 MHz, CDCl$_3$): δ 8.33 (br s, 1H), 7.63 (d, J=7.3 Hz, 2H), 7.57 (s, 1H), 7.43 (t, J=7.31 Hz, 2H), 7.33 (t, J=6.9 Hz, 1H), 7.27 (t, J=8.6 Hz, 1H), 7.12 (d, J=8.6 Hz, 1H), 6.75 (s, 1H); $^{13}$C NMR (100 MHz, CDCl$_3$): δ 139.3, 135.1, 131.8, 130.3, 129.1, 128.1, 125.8, 125.2, 122.5, 119.9, 111.8, 99.5; HRMS (ESI) Calcd for C$_{14}$H$_{10}$ClN [M+H]$^+$ 228.0580, found 228.0578. The $^1$H and $^{13}$C NMR spectral data are in good agreement with the literature data (Du, P.; Brosmer, J. L.; Peters, D. G. *Org. Lett.* 2011, 13, 4072).

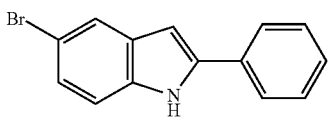

5-Bromo-2-phenyl-1H-indole (2o)

White solid (93% yield, eluent=hexane/EtOAc (92:8)); Mp=196-197° C.; $^1$H NMR (400 MHz, CDCl$_3$): δ 8.32 (brs, 1H), 7.73 (s, 1H), 7.63-7.60 (com, 2H), 7.43 (t, J=7.4 Hz, 2H), 7.33 (td, J=7.4, 1.5 Hz, 1H), 7.25-7.24 (com, 2H), 6.73 (s, 1H); $^{13}$C NMR (100 MHz, CDCl$_3$): δ 139.0, 135.3, 131.7, 130.9, 129.0, 128.1, 125.2, 125.1, 123.0, 113.4, 112.2, 99.4; HRMS (ESI) Calcd for C$_{14}$H$_{10}$NBr [M+H]$^+$ 272.0075, found 272.0085. The $^1$H and $^{13}$C NMR spectral data are in good agreement with the literature data (Deprez, N. R., supra).

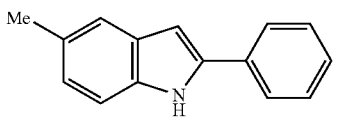 [SMILES: Cc1ccc2[nH]c(-c3ccccc3)cc2c1]

5-Methyl-2-phenyl-1H-indole (2p)

White solid (92% yield, eluent=hexane/EtOAc (92:8)); Mp=216-218° C.; $^1$H NMR (400 MHz, CDCl$_3$): δ 8.13 (brs, 1H), 7.55 (d, J=7.3 Hz, 2H), 7.33-7.31 (com, 3H), 7.23-7.14 (com, 2H), 6.91 (d, J=8.2 Hz, 1H), 6.65 (s, 1H), 2.34 (s, 3H); $^{13}$C NMR (100 MHz, CDCl$_3$): δ 137.9, 135.1, 132.5, 129.5, 129.4, 128.9, 127.5, 125.0, 123.9, 120.3, 110.5, 99.5, 21.5; HRMS (ESI) Calcd for C$_{15}$H$_{13}$N [M+H]$^+$ 208.1126, found 208.1121. The $^1$H and $^{13}$C NMR spectral data are in good agreement with the literature data (Shen, M, supra).

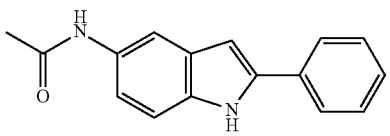 [SMILES: CC(=O)Nc1ccc2[nH]c(-c3ccccc3)cc2c1]

N-(2-Phenyl-1H-indol-5-yl)acetamide (2q)

Pale yellow solid (64% yield, eluent=hexane/EtOAc (20:80)); Mp=218-219° C.; $^1$H NMR (400 MHz, acetone-d$_6$): δ 10.60 (brs, 1H), 9.01 (brs, 1H), 8.00 (s, 1H), 7.85 (d, J=7.4 Hz, 2H), 7.44 (t, J=7.6 Hz, 2H), 7.33-7.27 (m, 3H), 6.85 (d, J=1.8 Hz, 1H), 2.08 (s, 3H); $^{13}$C NMR (100 MHz, acetone-d$_6$): δ 167.4, 138.6, 134.3, 132.7, 132.4, 129.2, 128.9, 127.3, 125.0, 115.5, 110.9; 110.7, 99.1, 23.4; HRMS (ESI) Calcd for C$_{16}$H$_{14}$N$_2$O [M+H]$^+$ 251.1184, found 251.1185.

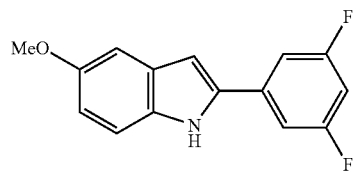 [SMILES: COc1ccc2[nH]c(-c3cc(F)cc(F)c3)cc2c1]

5-Methoxy-2-(3,5-difluorophenyl)-1H-indole (2r)

White solid (86% yield, eluent=hexane/EtOAc (92:8)); Mp=149-150° C.; $^1$H NMR (400 MHz, CDCl$_3$): δ 8.16 (brs, 1H), 7.26 (d, J=8.9 Hz, 1H), 7.11-7.07 (m, 3H), 6.89 (dd, J=8.9, 2.5 Hz, 1H), 6.76-6.70 (m, 2H), 3.85 (s, 3H); $^{13}$C NMR (100 MHz, CDCl$_3$): δ 163.6 (dd, $^1J_{C-F}$=248.3 Hz, $^3J_{C-F}$=13.8 Hz), 154.7, 136.2 (t, $^4J_{C-F}$=2.9 Hz), 135.6 (t, $^3J_{C-F}$=10.4 Hz), 132.3, 129.4, 113.9, 120.0, 107.7 (dd, $^2J_{C-F}$=19.0 Hz, $^4J_{C-F}$=7.3 Hz), 102.7 (d, $^2J_{C-F}$=25.6 Hz), 102.4, 101.6, 55.8; HRMS (ESI) Calcd for C$_{15}$H$_{11}$ONF$_2$ [M+H]$^+$ 260.0887, found 260.0891.

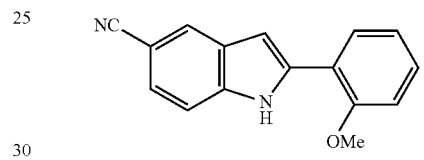

2-(2-Methoxyphenyl)-1H-indole-5-carbonitrile (2s)

White solid (89% yield, eluent=hexane/EtOAc (70:30)); Mp=145-146° C.; $^1$H NMR (400 MHz, CDCl$_3$): δ 9.99 (s, 1H), 7.94 (s, 1H), 7.81 (dd, J=7.8, 1.6 Hz, 1H), 7.45 (d, J=8.6 Hz, 1H), 7.39-7.32 (com, 2H), 7.11-7.04 (com, 2H), 6.91 (d, J=1.3 Hz, 1H), 4.03 (s, 3H); $^{13}$C NMR (100 MHz, acetone-d$_6$): δ 155.9, 138.5, 137.6, 129.6, 128.5, 127.8, 125.7, 124.6, 121.7, 121.1, 119.3, 120.0, 111.8, 102.7, 100.1, 55.9; HRMS (ESI) Calcd for C$_{16}$H$_{13}$N$_2$O [M+H]$^+$ 249.1028, found 249.1018.

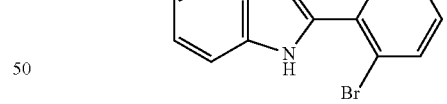

Ethyl 2-(2-bromophenyl)-1H-indole-5-carboxylate (2t)

White solid (22% yield, eluent=hexane/EtOAc (90:10)); Mp=157-158° C.; $^1$H NMR (400 MHz, CDCl$_3$): δ 8.84 (brs, 1H), 8.44 (s, 1H), 7.95 (dd, J=8.5, 1.6 Hz, 1H), 7.70 (dd, J=8.0, 1.0 Hz, 1H), 7.62 (dd, J=7.8, 1.6 Hz, 1H), 7.45-7.39 (m, 2H), 7.26-7.22 (m, 1H), 6.90 (d, J=1.4 Hz, 1H), 4.41 (q, J=7.1 Hz, 2H), 1.43 (t, J=7.2 Hz, 3H); $^{13}$C NMR (100 MHz, CDCl$_3$): δ 167.6, 138.7, 137.6, 134.1, 132.9, 131.5, 129.6, 127.8, 127.7, 124.0, 123.8, 122.7, 121.3, 110.7, 104.7, 60.6, 14.5; HRMS (ESI) Calcd for C$_{17}$H$_{14}$BrNO$_2$ [M+H]$^+$ 344.0286, found 344.0280.

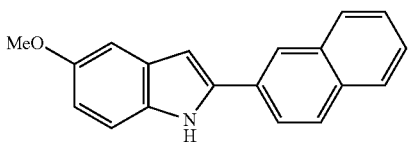 [SMILES: COc1ccc2[nH]c(-c3ccc4ccccc4c3)cc2c1]

5-Methoxy-2-(naphthalen-2-yl)-1H-indole (2u)

White solid (78% yield, eluent=hexane/EtOAc (92:8)); Mp=213-214° C.; $^1$H NMR (400 MHz, CDCl$_3$): δ 8.37 (brs, 1H), 8.03 (s, 1H), 7.90-7.79 (m, 4H), 7.52-7.45 (m, 2H), 7.31 (d, J=8.8 Hz, 1H), 7.11 (d, J=2.2 Hz, 1H), 6.90-6.87 (m, 2H), 3.88 (s, 3H); $^{13}$C NMR (100 MHz, CDCl$_3$): δ 154.6, 138.6, 133.6, 132.8, 132.3, 129.9, 129.8, 128.8, 128.0, 127.8, 126.7, 126.1, 123.7, 122.9, 112.9, 111.7, 102.3, 100.5, 55.9; HRMS (ESI) Calcd for C$_{19}$H$_{15}$NO [M+H]$^+$ 274.1232, found 274.1228.

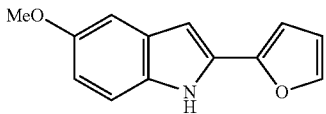 [SMILES: COc1ccc2[nH]c(-c3ccco3)cc2c1]

2-(Furan-2-yl)-5-methoxy-1H-indole (2v)

White solid (76% yield, eluent=hexane/EtOAc (92:8)); Mp=185-186° C.; $^1$H NMR (400 MHz, CDCl$_3$): δ 8.33 (brs, 1H), 7.43 (d, J=1.4 Hz, 1H), 7.23 (d, J=8.8 Hz, 1H), 7.05 (d, J=2.3 Hz, 1H), 6.84 (dd, J=8.8, 2.5 Hz, 1H), 6.66 (d, J=1.3 Hz, 1H), 6.59 (d, J=3.4 Hz, 1H), 6.49-6.47 (m, 1H), 3.85 (s, 3H); $^{13}$C NMR (100 MHz, CDCl$_3$): δ 154.6, 147.8, 141.7, 131.3, 129.9, 129.3, 112.8, 111.8, 111.6, 105.3, 102.2, 98.7, 55.8; HRMS (ESI) Calcd for C$_{13}$H$_{11}$NO$_2$ [M+H]$^+$ 214.0868, found 214.0872.

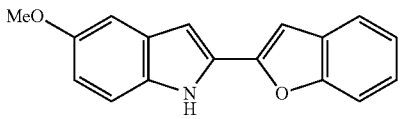 [SMILES: COc1ccc2[nH]c(-c3cc4ccccc4o3)cc2c1]

2-(Benzofuran-2-yl)-5-methoxy-1H-indole (2w)

White solid (84% yield, eluent=hexane/EtOAc (92:8)); Mp=185-186° C.; $^1$H NMR (400 MHz, CDCl$_3$): δ 8.54 (brs, 1H), 7.56 (d, J=7.2 Hz, 1H), 7.50 (d, J=7.7 Hz, 1H), 7.30-7.21 (m, 3H), 7.08 (d, J=2.2 Hz, 1H), 6.93-6.88 (m, 3H), 3.86 (s, 3H); $^{13}$C NMR (100 MHz, CDCl$_3$): δ 154.7, 154.5, 149.4, 131.7, 129.2, 129.2, 129.1, 124.4, 123.3, 120.9, 113.7, 111.9, 111.0, 102.2, 101.3, 101.0, 55.8; HRMS (ESI) Calcd for C$_{17}$H$_{13}$NO$_2$ [M+H]$^+$ 264.1025, found 264.1025.

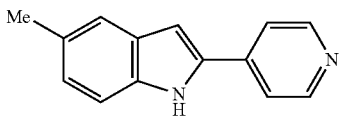 [SMILES: Cc1ccc2[nH]c(-c3ccncc3)cc2c1]

5-Methoxy-2-(pyridin-4-yl)-1H-indole (2x)

Yellow solid (80% yield, eluent=hexane/EtOAc (20:80)); Mp=207-208° C.; $^1$H NMR (400 MHz, CDCl$_3$): δ 8.68 (brs, 1H), 8.64 (d, J=4.7 Hz, 2H), 7.51 (d, J=4.6 Hz, 2H), 7.32 (d, J=8.9 Hz, 1H), 7.10 (d, J=2.3 Hz, 1H), 6.96 (d, J=1.5 Hz, 1H), 6.92 (dd, J=8.8, 2.4 Hz, 1H), 3.87 (s, 3H); $^{13}$C NMR (100 MHz, CDCl$_3$): δ 154.8, 150.4, 139.5, 135.2, 132.6, 129.3, 119.0, 114.5, 112.1, 102.6, 102.3, 55.8; HRMS (ESI) Calcd for C$_{14}$H$_{12}$N$_2$O [M+H]$^+$ 225.1028, found 225.1031.

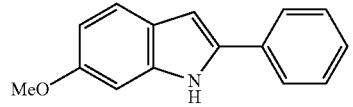

6-Methoxy-2-phenyl-1H-indole (2y)

White solid (74% yield, eluent=hexane/EtOAc (92:8)); Mp=177-178° C.; $^1$H NMR (400 MHz, CDCl$_3$): δ 8.22 (brs, 1H), 7.61 (d, J=7.8 Hz, 2H), 7.49 (d, J=8.7 Hz, 1H), 7.41 (t, J=7.6 Hz, 2H), 7.28 (t, J=7.4 Hz, 1H), 6.89 (s, 1H), 6.79 (dd, J=8.6, 1.9 Hz, 1H), 6.75 (s, 1H), 3.85 (s, 3H); $^{13}$C NMR (100 MHz, CDCl$_3$): δ 156.7, 137.7, 136.8, 132.6, 129.0, 127.3, 124.7, 123.6, 121.3, 110.2, 99.9, 94.5, 55.7; HRMS (ESI) Calcd for C$_{15}$H$_{13}$NO [M+H]$^+$ 224.1075, found 224.1085. The $^1$H and $^{13}$C NMR spectral data are in good agreement with the literature data (Shen M, supra).

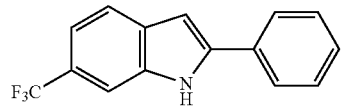 [SMILES: FC(F)(F)c1ccc2cc(-c3ccccc3)[nH]c2c1]

6-Trifluoromethyl-2-phenyl-1H-indole (2z)

White solid (72% yield, eluent=hexane/EtOAc (95:5)); Mp=171-172° C.; $^1$H NMR (400 MHz, CDCl$_3$): δ 8.52 (brs, 1H), 7.71-7.68 (m, 4H), 7.48 (t, J=7.8 Hz, 2H), 7.41-7.36 (m, 2H), 6.87 (d, J=1.5 Hz, 1H); $^{13}$C NMR (100 MHz, CDCl$_3$): δ 140.6, 135.6, 131.6, 129.2, 128.5, 125.2 (q, $^1J_{C-F}$=271.0 Hz), 125.4, 124.2 (q, $^2J_{C-F}$=31.9 Hz), 120.9, 117.1 (q, $^3J_{C-F}$=3.6 Hz), 117.0, 108.4 (q, $^3J_{C-F}$=4.0 Hz), 100.1; HRMS (ESI) Calcd for C$_{15}$H$_{10}$F$_3$N [M+H]$^+$ 262.0844, found 262.0847. The $^1$H and $^{13}$C NMR spectral data are in good agreement with the literature data (Shen M, supra).

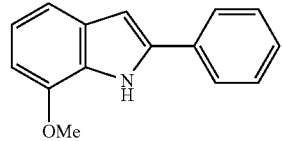 [SMILES: COc1cccc2cc(-c3ccccc3)[nH]c12]

7-Methoxy-2-phenyl-1H-indole (2aa)

White solid (67% yield, eluent=hexane/EtOAc (92:8)); Mp=94-95° C.; $^1$H NMR (400 MHz, CDCl$_3$): δ 8.58 (brs, 1H), 7.64 (dd, J=8.4, 1.0 Hz, 2H), 7.41 (t, J=7.3 Hz, 2H), 7.31-7.27 (com, 1H), 7.23 (d, J=8.1 Hz, 1H), 7.03 (t, J=7.7

Hz, 1H), 6.77 (d, J=2.3 Hz, 1H), 6.63 (d, J=7.7 Hz, 1H), 3.95 (s, 3H); $^{13}$C NMR (100 MHz, CDCl$_3$): δ 145.9, 137.5, 132.4, 130.4, 128.9, 127.5, 127.2, 125.1, 120.5, 113.3, 102.1, 100.2, 55.3; HRMS (ESI) Calcd for C$_{15}$H$_{13}$NO [M+H]$^+$ 224.1075, found 224.1085. The $^1$H and $^{13}$C NMR spectral data are in good agreement with the literature data (Candito, D. A., supra).

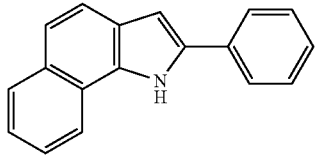 [SMILES: c1ccc(-c2cc3ccc4ccccc4c3[nH]2)cc1]

2-Phenylbenzo[g]indole (2ab)

White solid (88% yield, eluent=hexane/EtOAc (92:8)); Mp=171-172° C.; NMR (400 MHz, CDCl$_3$): δ 8.98 (brs, 1H), 8.03 (d, J=8.2 Hz, 1H), 7.91 (d, J=7.9 Hz, 1H), 7.71-7.68 (m, 3H), 7.54-7.50 (m, 2H), 7.47-7.40 (m, 3H), 7.31 (td, J=7.4, 1.0 Hz, 1H), 6.93 (d, J=2.3 Hz, 1H); $^{13}$C NMR (100 MHz, CDCl$_3$): δ 136.3, 132.5, 131.4, 130.6, 129.2, 129.1, 127.5, 125.6, 125.3, 125.0, 124.0, 121.6, 121.2, 120.6, 119.4, 101.7; HRMS (ESI) Calcd for C$_{18}$H$_{13}$N [M+H]$^+$ 244.1126, found 244.1122. The $^1$H and $^{13}$C NMR spectral data are in good agreement with the literature data (Wagaw, S., supra).

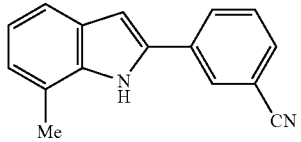 [SMILES: Cc1cccc2cc(-c3cccc(C#N)c3)[nH]c12]

3-(7-Methyl-1H-indol-2-yl)benzonitrile (2ac)

White solid (87% yield, eluent=hexane/EtOAc (92:8)); Mp=193-194° C.; $^1$H NMR (400 MHz, CDCl$_3$): δ 8.37 (brs, 1H), 8.00 (s, 1H), 7.93 (d, J=7.6 Hz, 1H), 7.60-7.50 (m, 3H), 7.10-7.05 (m, 2H), 6.91 (d, J=1.9 Hz, 1H), 2.58 (s, 3H); $^{13}$C NMR (100 MHz, CDCl$_3$): δ 136.9, 135.1, 133.9, 130.6, 129.9, 129.4, 128.5, 128.4, 123.9, 120.9, 120.5, 118.8, 118.7, 113.2, 102.2, 16.8; HRMS (ESI) Calcd for C$_{16}$H$_{12}$N$_2$ [M+H]$^+$ 233.1079, found 233.1075.

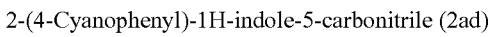

2-(4-Cyanophenyl)-1H-indole-5-carbonitrile (2ad)

White solid (74% yield, eluent=hexane/EtOAc (90:10)); Mp=306-307° C.; $^1$H NMR (400 MHz, DMSO-d$_6$): δ 12.38 (s,1H), 8.17 (s, 1H), 8.12 (d, J=8.1 Hz, 2H), 8.00 (d, J=8.2 Hz, 2H), 7.63 (d, J=8.7 Hz, 1H), 7.54 (d, J=8.4 Hz, 1H), 7.31 (s, 1H); $^{13}$C NMR (100 MHz, DMSO-d$_6$): δ 138.7, 137.7, 135.0, 132.5, 127.5, 125.8, 125.3, 124.7, 120.0, 118.3, 112.3, 109.6, 101.5, 101.5; HRMS (ESI) Calcd for C$_{16}$H$_9$N$_3$ [M+H]$^+$ 244.0875, found 244.0882.

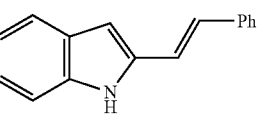

(E)-5-Methoxy-2-styryl-1H-indole (2ae)

Light brown solid (78% yield, eluent=hexane/EtOAc (92:8)); Mp=150-151° C.; $^1$H NMR (400 MHz, acetone-d$_6$): δ 10.37 (s, 1H), 7.55 (d, J=8.4 Hz, 2H), 7.34 (t, J=8.0 Hz, 2H), 7.22-7.29 (com, 3H), 7.15 (d, J=16.8 Hz, 1H), 7.00 (d, J=2.4 Hz, 1H), 6.77 (dd, J=8.8, 2.4 Hz, 1H), 6.55 (d, J=1.6 Hz, 1H), 3.78 (s, 3H); $^{13}$C NMR (100 MHz, acetone-d$_6$): δ 154.9, 138.1, 138.0, 133.4, 130.1, 129.3, 127.9, 127.3, 126.7, 120.1, 113.3, 112.1, 103.7, 102.2, 55.5; HRMS (ESI) Calcd for C$_{17}$H$_{15}$NO [M+H]$^+$ 250.1232, found 250.1224.

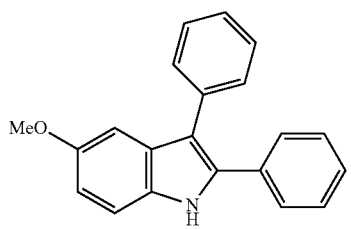 [SMILES: COc1ccc2[nH]c(-c3ccccc3)c(-c3ccccc3)c2c1]

5-Methoxy-2,3-diphenyl-1H-indole (2af)

The reaction was performed with the Pd/Cu system; White solid (86% yield, eluent=hexane/EtOAc (92:8)); Mp=159-160° C.; $^1$H NMR (400 MHz, CDCl$_3$): δ 8.13 (brs, 1H), 7.45-7.38 (m, 6H), 7.34-7.28 (m, 5H), 7.12 (d, J=2.1 Hz, 1H), 6.91 (dd, J=8.7, 2.4 Hz, 1H), 3.83 (s, 3H); $^{13}$C NMR (100 MHz, CDCl$_3$): δ 154.8, 135.2, 135.0, 132.8, 131.1, 130.1, 129.2, 128.7, 128.6, 128.1, 127.6, 126.2, 115.0, 113.1, 111.7, 101.3, 56.0; HRMS (ESI) Calcd for C$_{21}$H$_{17}$NO [M+H]$^+$ 300.1388, found 300.1386.

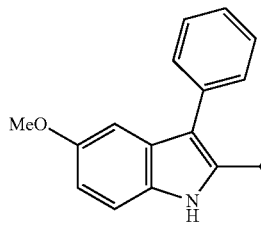

5-Methoxy-2-(4-methoxyphenyl)-3-phenyl-1H-indole (2ag)

The reaction was performed with the Pd/Cu system; White solid (82% yield, eluent=hexane/EtOAc (92:8)); Mp=58-59° C.; $^1$H NMR (400 MHz, CDCl$_3$): δ 8.09 (s, 1H), 7.46-7.38 (com, 4H), 7.34-7.29 (com, 4H), 7.14 (d, J=1.8 Hz, 1H), 6.90 (dd, J=8.7, 2.3 Hz, 1H), 6.85 (d, J=8.8 Hz, 2H), 3.84 (s, 3H), 3.1 (s, 3H); $^{13}$C NMR (100 MHz, CDCl$_3$): δ 159.1, 154.7, 135.4, 135.0, 130.9, 130.0, 129.3, 129.1, 128.5, 126.0, 125.2, 114.1, 114.0, 112.5, 111.5, 101.1, 55.9, 55.2; HRMS (ESI) Calcd for C$_{22}$H$_{19}$NO$_2$ [M+H]$^+$ 330.1494, found 330.1491.

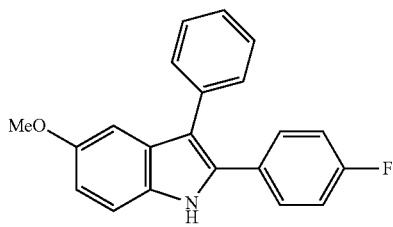 [SMILES: COc1ccc2[nH]c(-c3ccc(F)cc3)c(-c3ccccc3)c2c1]

5-Methoxy-2-(4-fluorophenyl)-3-phenyl-1H-indole (2ah)

The reaction was performed with the Pd/Cu system; White solid (74% yield, eluent=hexane/EtOAc (92:8)); Mp=140-141° C.; $^1$H NMR (400 MHz, CDCl$_3$): δ 8.07 (s, 1H), 7.40-7.37 (com, 4H), 7.33-7.26 (com, 4H), 7.10 (d, J=2.4 Hz, 1H), 6.97 (t, J=8.8 Hz, 2H), 6.89 (dd, J=8.7, 2.5 Hz, 1H), 3.80 (s, 3H); $^{13}$C NMR (100 MHz, CDCl$_3$): δ 162.3 (d, $^1J_{C\text{-}F}$=248 Hz), 154.9, 135.0, 134.1, 131.1, 130.1, 129.8 (d, $^3J_{C\text{-}F}$=7.9 Hz), 129.1, 128.8 (d, $^4J_{C\text{-}F}$=3.2 Hz), 128.7, 126.3, 115.7 (d, $^2J_{C\text{-}F}$=21.6 Hz), 115.0, 113.1, 111.8, 101.3, 56.0; HRMS (ESI) Calcd for C$_{21}$H$_{16}$FNO [M+H]$^+$ 318.1294, found 318.1292.

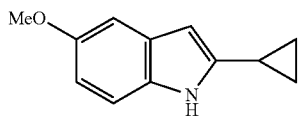 [SMILES: COc1ccc2[nH]c(C3CC3)cc2c1]

2-Cyclopropyl-5-methoxy-1H-indole (2ai)

Yellow oil (84% yield, eluent=hexane/EtOAc (92:8)); $^1$H NMR (400 MHz, CDCl$_3$): δ 7.85 (brs, 1H), 7.15 (d, J=8.7 Hz, 1H), 7.00 (d, J=2.4 Hz, 1H), 6.78 (dd, J=8.8, 2.5 Hz, 1H), 6.09 (d, J=2.0 Hz, 1H), 3.85 (s, 3H), 1.97-1.90 (m, 1H), 0.99-0.94 (m, 2H), 0.80-0.75 (m, 2H); $^{13}$C NMR (100 MHz, CDCl$_3$): δ 154.2, 142.6, 130.9, 129.2, 110.9, 110.8, 101.9, 97.6, 55.9, 9.0, 7.4; HRMS (ESI) Calcd for C$_{12}$H$_{13}$NO [M+H]$^+$ 188.1075, found 188.1082.

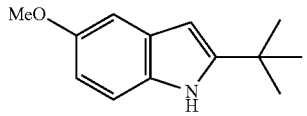

2-(tert-Butyl)-5-methoxy-1H-indole (2aj)

White solid (61% yield, eluent=hexane/EtOAc (92:8)); Mp=104-105° C.; $^1$H NMR (400 MHz, CDCl$_3$): δ 7.85 (brs, 1H), 7.18 (d, J=8.8 Hz, 1H), 7.02 (d, J=2.4 Hz, 1H), 6.78 (dd, J=8.7, 2.5 Hz, 1H), 6.19 (d, J=1.9 Hz, 1H), 3.83 (s, 3H), 1.37 (s, 9H); $^{13}$C NMR (100 MHz, CDCl$_3$): δ 154.1, 149.7, 130.9, 129.0, 111.1, 111.0, 102.2, 96.9, 56.0, 31.9, 30.3; HRMS (ESI) Calcd for C$_{13}$H$_{17}$NO [M+H]$^+$ 204.1388, found 204.1391. The $^1$H and $^{13}$C NMR spectral data are in good agreement with the literature data (Smith, K., supra).

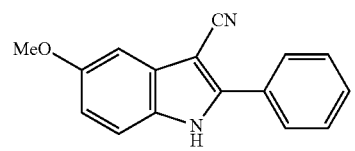 [SMILES: COc1ccc2[nH]c(-c3ccccc3)c(C#N)c2c1]

5-Methoxy-2-phenyl-1H-indole-3-carbonitrile (2ak)

The reaction was performed according to the general procedure with enamine as the starting material; White solid (85% yield, eluent=hexane/EtOAc (90:10)); Mp=251-252° C.; $^1$H NMR (400 MHz, DMSO-d$_6$): δ 12.49 (s, 1H), 7.97 (d, J=7.9 Hz, 2H), 7.63 (t, J=7.6 Hz, 2H), 7.55 (t, J=7.2 Hz, 1H), 7.47 (d, J=8.8 Hz, 1H), 7.11 (d, J=2.4 Hz, 1H), 6.96 (dd, J=8.7, 1.3 Hz, 1H), 3.85 (s, 3H); $^{13}$C NMR (100 MHz, DMSO-d$_6$): δ 156.0, 145.1, 130.9, 130.3, 130.0, 129.8, 129.7, 127.3, 117.7, 114.8, 114.1, 100.1, 81.7, 55.9; HRMS (ESI) Calcd for C$_{16}$H$_{12}$ON$_2$ [M+H]$^+$ 224.1075, found 224.1069.

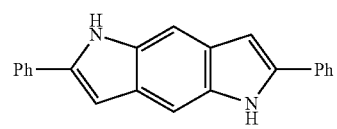

2,6-Diphenyl-1,5-dihydropyrrolo[2,3-f]indole (2al)

The reaction was performed using 20 mol % of Pd(OAc)$_2$ and 4 equiv of Bu$_4$NBr; Light brown solid (29% yield, eluent=hexane/EtOAc (90:10)); Mp=242-243° C.; $^1$H NMR (400 MHz, DMSO-d$_6$): δ 11.45 (s, 2H), 7.88 (d, J=7.32 Hz, 4H), 7.47 (t, J=7.7 Hz, 4H), 7.28 (t, J=7.7 Hz, 2H), 7.22 (s, 2H), 7.11 (d, J=2.0 Hz, 2H); $^{13}$C NMR (100 MHz, DMSO-d$_6$): δ 135.0, 132.5, 131.6, 128.6, 126.2, 124.1, 120.3, 106.9, 97.4; HRMS (ESI) Calcd for C$_{22}$H$_{16}$N$_2$ [M+H]$^+$ 309.1392, found 309.1397.

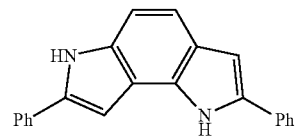 [SMILES: c1ccc(-c2cc3c(ccc4cc(-c5ccccc5)[nH]c43)[nH]2)cc1]

2,7-Diphenyl-1,6-dihydropyrrolo[2,3-e]indole (2 am)

The reaction was performed using 20 mol % of Pd(OAc)$_2$ and 4 equiv of Bu$_4$NBr; White solid (50% yield, eluent=hexane/EtOAc (90:10)); Mp=226-227° C.; $^1$H NMR (400 MHz, CDCl$_3$): δ 8.62 (s, 1H), 8.48 (s, 1H), 7.70-7.67 (com, 4H), 7.44-7.42 (com, 5H), 7.32-7.19 (com, 3H), 6.99 (s, 1H), 6.92 (s, 1H); $^{13}$C NMR (100 MHz, CDCl$_3$): δ 136.0, 134.7, 134.2, 133.0, 132.6, 129.6, 129.1, 129.0, 127.3, 126.8, 124.8, 124.6, 122.5, 116.2, 114.6, 105.7, 101.3, 96.1; HRMS (ESI) Calcd for C$_{22}$H$_{16}$N$_2$ [M+H]$^+$ 309.1392, found 309.1390.

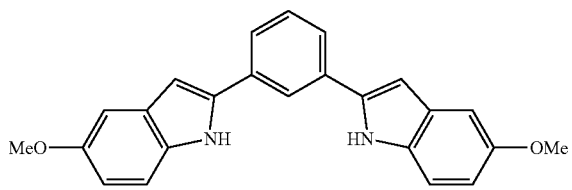 [SMILES: COc1ccc2[nH]c(-c3cccc(-c4cc5cc(OC)ccc5[nH]4)c3)cc2c1]

1,3-Bis(5-Methoxy-1H-indol-2-yl)benzene (2an)

The reaction was performed using 20 mol % of Pd(OAc)$_2$ and 4 equiv of Bu$_4$NBr; Light brown solid (90% yield, eluent=hexane/EtOAc (90:10)); Mp=223-224° C.; $^1$H NMR (400 MHz, acetone-d$_6$): δ 10.57 (s, 2H), 8.32 (s, 1H), 7.74 (dd, J=7.8, 1.3 Hz, 2H), 7.47 (t, J=7.8 Hz, 1H), 7.34 (d, J=8.7 Hz, 2H), 7.09 (d, J=2.0 Hz, 2H), 6.92 (dd, J=1.4 Hz, 2H), 6.80 (dd, J=8.7, 2.3 Hz, 2H), 3.80 (s, 6H); $^{13}$C NMR (100 MHz, acetone-d$_6$): δ 155.1, 138.9, 134.1, 133.3, 130.4, 130.1, 124.4, 122.1, 113.0, 112.4, 102.4, 100.1, 55.5; HRMS (ESI) Calcd for C$_{24}$H$_{20}$N$_2$O$_2$ [M+H]$^+$ 369.1603, found 369.1604.

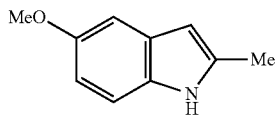 [SMILES: COc1ccc2[nH]c(C)cc2c1]

5-Methoxy-2-methyl-1H-indole (2ao)

The reaction was performed using 5 equiv of acetone (HPLC grade), 20 mol % of Pd(OAc)$_2$ and 3 equiv of Cu(OAc)$_2$; Light yellow solid (55% yield, eluent=hexane/EtOAc (92:8)); Mp=85-86° C.; $^1$H NMR (400 MHz, CDCl$_3$) δ 7.72 (brs, 1H), 7.15 (dt, J=8.7, 0.7 Hz, 1H), 6.99 (d, J=2.4 Hz, 1H), 6.76 (dd, J=8.7, 2.4 Hz, 1H), 6.14-6.13 (m, 1H), 3.83 (s, 3H), 2.41 (d, J=0.7 Hz, 3H); $^{13}$C NMR (100 MHz, CDCl$_3$) δ 154.2, 136.0, 131.2, 129.6, 110.9, 110.7, 101.9, 100.4, 56.0, 13.9; HRMS (ESI) Calcd for C$_{10}$H$_{11}$NO [M+H]$^+$ 162.0919, found 162.0923. The $^1$H and $^{13}$C NMR spectra showed good agreement with the literature data (Kasaya, Y; Hoshi, K; Terada, Y; Nishida, A.; Shuto, S.; Arisawa, M *Eur. J. Org. Chem.* 2009, 4606).

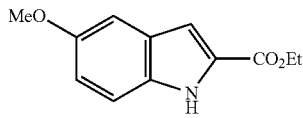 [SMILES: CCOC(=O)c1cc2cc(OC)ccc2[nH]1]

Ethyl 5-methoxy-1H-indole-2-carboxylate (2ap)

The reaction was performed using 5 equiv of ethyl pyruvate, 20 mol % of Pd(OAc)$_2$ and 3 equiv of Cu(OAc)$_2$; White solid (41% yield, eluent=hexane/EtOAc (90:10)); Mp=156-157° C.; $^1$H NMR (400 MHz, CDCl$_3$): δ 8.86 (brs, 1H), 7.31 (d, J=9.0 Hz, 1H), 7.15 (d, J=1.9 Hz, 1H), 7.08 (d, J=2.4 Hz, 1H), 7.00 (dd, J=8.9, 2.4 Hz, 1H), 4.40 (q, J=7.2 Hz, 2H), 3.85 (s, 3H), 1.41 (t, J=7.1 Hz, 3H); $^{13}$C NMR (100 MHz, CDCl$_3$): δ 161.9, 154.7, 132.1, 127.9, 127.8, 117.0, 112.7, 108.2, 102.6, 61.0, 55.7, 14.4; HRMS (ESI) Calcd for C$_{12}$H$_{13}$NO$_3$ [M+H]$^+$ 220.0974, found 220.0972.

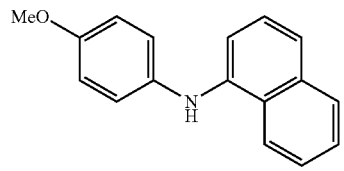 [SMILES: COc1ccc(Nc2cccc3ccccc23)cc1]

N-(4-methoxyphenyl)naphthalen-1-amine (3, Scheme 4b)

Light brown solid (78% yield, eluent=hexane/EtOAc (98:2)); Mp=111-112° C.; $^1$H NMR (400 MHz, CDCl$_3$): δ 8.02-8.00 (m, 1H), 7.87-7.83 (m, 1H), 7.52-7.47 (m, 2H), 7.45 (d, J=8.5 Hz, 1H), 7.33 (t, J=7.8 Hz, 1H), 7.11 (d, J=7.0 Hz, 1H), 7.09-7.05 (m, 2H), 6.91-6.87 (m, 2H), 5.87 (brs, 1H), 3.82 (s, 3H); $^{13}$C NMR (100 MHz, CDCl$_3$): δ 155.1, 140.9, 136.9, 134.6, 128.6, 126.2, 126.0, 125.9, 125.4, 121.9, 121.1, 120.9, 114.8, 111.7, 55.6; HRMS (ESI) Calcd for C$_{17}$H$_{15}$NO [M+H]$^+$ 250.1232, found 250.1233. The $^1$H and $^{13}$C NMR spectra showed good agreement with the literature data (Desmarets, C.; Champagne, B.; Walcarius, A.; Bellouard, C.; Omar-Amrani, R.; Ahajji, A.; Fort, Y; Schneider, R. J. *Org. Chem.* 2006, 71, 1351).

Example 6

Kinetic Isotope Effect Experiments (A) Intramolecular Competition Reaction (Scheme 3a)

The reaction of 2-deuterio-(E)-N-(1-(4-chlorophenyl)ethylidene)aniline (1aq-d, 0.2 mmol) was performed under the standard conditions for 12 h, followed by the standard workup and purification to afford a mixture of 2aq-d and 2aq in 84% yield, respectively. $^1$H NMR analysis of the mixture indicated a KIE value of 5.2 (see the spectrum as shown in FIG. 1).

(B) Intermolecular Competition (Scheme 3b)

Figure 2:
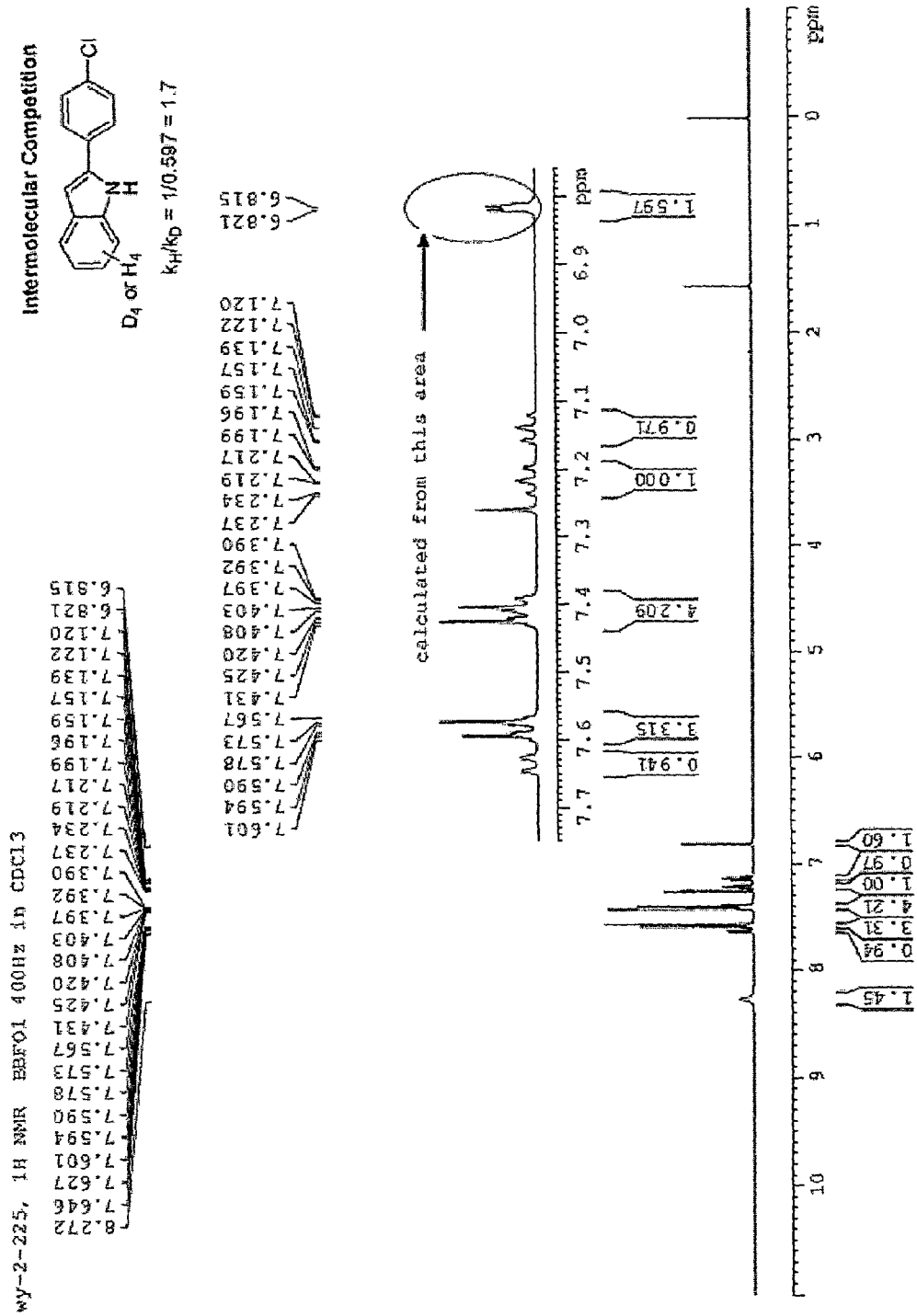
FIG. 2 is a $^1$H NMR analysis spectrum illustrating intermolecular competition based on Scheme 3b.

A mixture of 1aq and 1aq-d$_5$ (0.2 mmol each) was subjected to the standard conditions for 3 h. Purification of the crude product on silica gel afforded a mixture of 2aq and 2aq-d$_4$ in 22% combined yield, the ratio of which was determined to be 1.7:1 by $^1$H NMR analysis (see the spectrum as shown in FIG. 2).

(C) Individual Reactions of 1aq and 1aq-d$_5$ (Scheme 3c)

Figure 3:
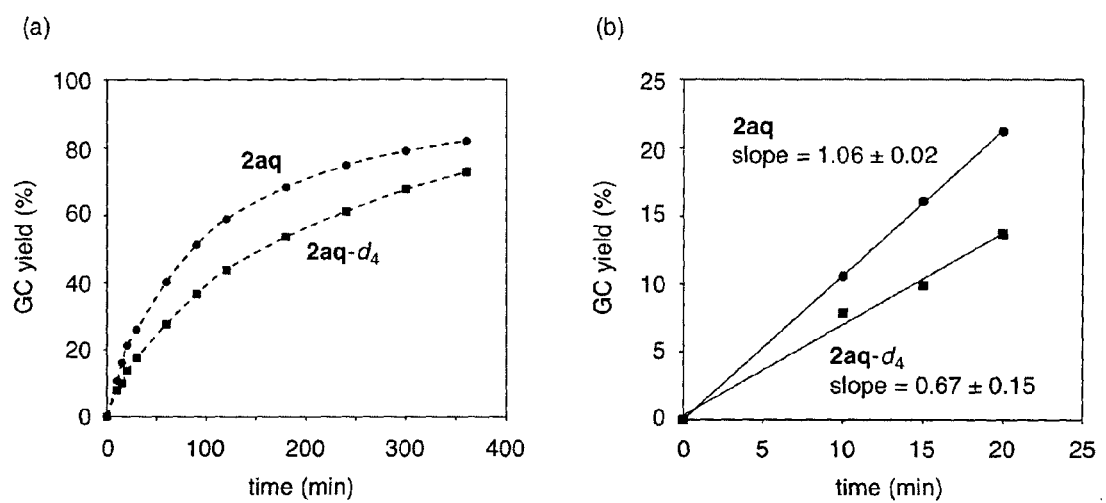
FIGS. 3A and B are graphs showing progress of individual reactions of 1aq and 1aq-d$_5$ as monitored by gas chromatography (GC) analysis.

Parallel individual reactions of 1aq and 1aq-d$_5$ under the standard conditions were monitored by GC analysis of periodically taken aliquots (0-360 min, FIG. 3A). Comparison of the reaction progress in the early stage (0-20 min) indicated a kinetic isotope effect of 1.6±0.4 (FIG. 3B).

A palladium(II)-catalyzed oxidative cyclization reaction of N-aryl imines to indoles that likely involves palladation of N-aryl enamines formed via imine-enamine tautomerization has been developed. The reaction features operational simplicity, mild aerobic conditions, and tolerance of a broad range of functional groups, thus allowing expedient and atom-economical assembly of indole rings from readily available anilines and ketones.

The inventors of the present invention made the surprising finding regarding this simple yet unprecedented transformation from imine to indole while carrying out experiments relating to ortho C—H bond functionalization of aromatic imines and oxidative palladium catalysis, with intention to oxidatively functionalize the ortho C—H bond of the phenyl ring of 1a (refer Table 2) via imine-directed cyclopalladation.

It was further noted that no products arising from ortho C—H functionalization were obtained under any conditions examined and carried out as described herein.

Example 7

Discussion and Results

Table 2 summarizes key results obtained during the optimization of the reaction on a small scale (0.2 mmol). The Pd-catalyzed reaction of 1a using $O_2$ only at 40° C. afforded 2a in 27% yield (entry 1). A clear improvement of the yield was observed when $Bu_4NBr$ (1 equiv) was added (entry 2), while other ammonium salts did not show apparent positive effects (entries 3-5). By using 2 equiv of $Bu_4NBr$, 2a was obtained in 76% and 89% yields at 25° C. and 60° C., respectively (entries 6 and 7). A change of the oxygen atmosphere to an open air in the latter case afforded 2a in 67% yield. The use of $Cu(OAc)_2$ instead of $O_2/Bu_4NBr$ also allowed efficient and scalable cyclization, affording 2a in 93% and 87% yields on 0.2 mmol and 50 mmol scales, respectively (entries 8 and 9).

To the inventors' surprise, Glorius' catalytic system which includes the use of $K_2CO_3$ additive and DMF solvent did not promote the reaction at all. Thus, DMSO appears to play an important if not critical role in the oxidative cyclization. Other oxidants examined were either poorly effective (BzOOtBu, BQ; entries 10 and 11) or entirely ineffective ($CuCl_2$, AgOAc, $PhI(OAc)_2$ etc.). 52% yield was obtained when reaction was carried out with a stoichiometric amount of $Pd(OAc)_2$ in the absence of an oxidant (entry 12).

TABLE 2

Influence of Reaction Conditions on Oxidative Cyclization of 1a[a]

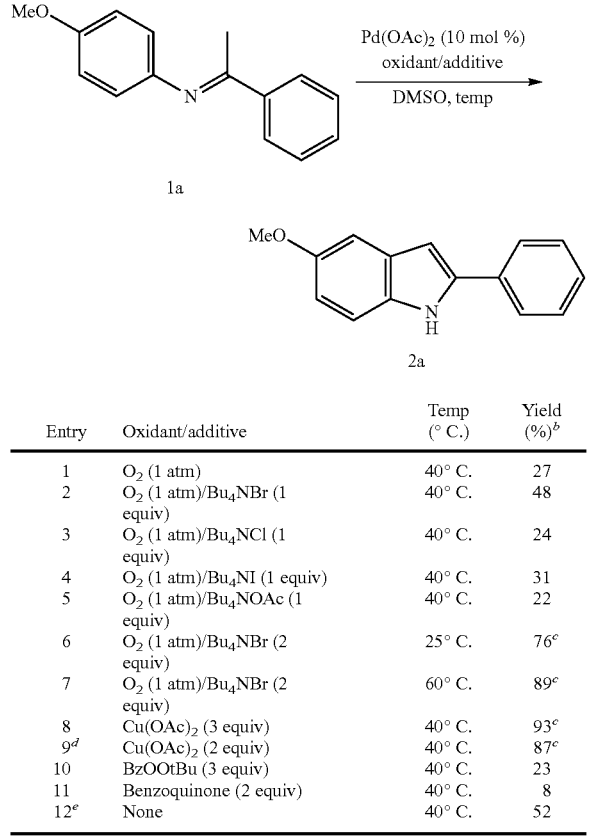

| Entry | Oxidant/additive | Temp (° C.) | Yield (%)[b] |
|---|---|---|---|
| 1 | $O_2$ (1 atm) | 40° C. | 27 |
| 2 | $O_2$ (1 atm)/$Bu_4NBr$ (1 equiv) | 40° C. | 48 |
| 3 | $O_2$ (1 atm)/$Bu_4NCl$ (1 equiv) | 40° C. | 24 |
| 4 | $O_2$ (1 atm)/$Bu_4NI$ (1 equiv) | 40° C. | 31 |
| 5 | $O_2$ (1 atm)/$Bu_4NOAc$ (1 equiv) | 40° C. | 22 |
| 6 | $O_2$ (1 atm)/$Bu_4NBr$ (2 equiv) | 25° C. | 76[c] |
| 7 | $O_2$ (1 atm)/$Bu_4NBr$ (2 equiv) | 60° C. | 89[c] |
| 8 | $Cu(OAc)_2$ (3 equiv) | 40° C. | 93[c] |
| 9[d] | $Cu(OAc)_2$ (2 equiv) | 40° C. | 87[c] |
| 10 | BzOOtBu (3 equiv) | 40° C. | 23 |
| 11 | Benzoquinone (2 equiv) | 40° C. | 8 |
| 12[e] | None | 40° C. | 52 |

[a]Reaction was performed on a 0.2 mmol scale for 12-16 h.
[b]GC yield determined using n-tridecane as an internal standard.
[c]Isolated yield.
[d]The reaction was performed on a 50 mmol scale using 5 mol % of $Pd(OAc)_2$.
[e]1 equiv of $Pd(OAc)_2$ was used.

The scope of the oxidative cyclization with the Pd/$Bu_4NBr$/$O_2$ system (Scheme 1) was explored. A series of 2-(hetero)arylindoles could be obtained in good to excellent yields from the corresponding imines derived from substituted anilines and acetophenones (2a to 2ad). A variety of electron-donating, electron-withdrawing, and potentially sensitive functional groups could be tolerated on both the aniline- and acetophenone-derived moieties, including nitro (2b and 2k), cyano (2c, 2s, 1ac, and 2ad), amide (2d and 2q), trifluoromethyl (2e, 2l, and 2z), chloro (2f and 2n), bromo (2g, 2o, and 2t), ester (2m and 2t), and fluoro (2r) groups. Note that the dicyanoindole 2ad is a precursor of an acid-sensing ion channel-3 inhibitor that was previously synthesized by Suzuki coupling of an expensive protected indole boronic acid. Heteroaryl groups such as 2-furyl, 2-benzofuryl, and 4-pyridyl groups could be tolerated (2v-2x). Imines derived from m-methoxy and -trifluoromethyl anilines underwent cyclization preferentially at the less-hindered position to afford the indoles 2y and 2z, respectively, while the former case was accompanied by a small amount (7%) of the minor regioisomer. Substituents at the ortho positions of the acetophenone- and the aniline-derived moieties (2s, 2t, and 2aa-2ac) were tolerated, while the yield was only modest for the indole derived from o-bromoacetophenone (2t).

Scheme 1' Indole Synthesis from N-Aryl Imines (excerpt of results shown in Scheme 1)

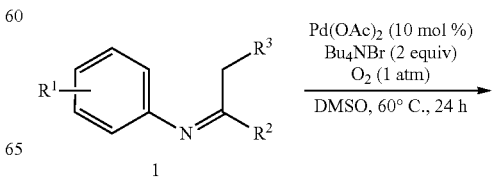

-continued
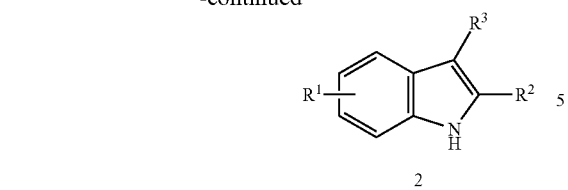
2
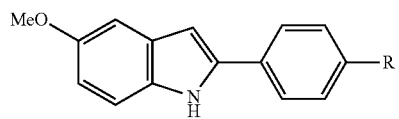
2a (R = H), 89%
2b (R = NO$_2$), 92%
2c (R = CN), 91%
2d (R = CONR'$_2$), 81%[a,b]
2e (R = CF$_3$), 86%
2f (R = Cl), 90%
2g (R = Br), 77%
2h (R = Me), 86%
2i (R = OMe), 82%
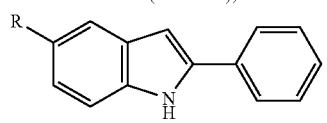
2j (R = H), 87%
2k (R = NO$_2$), 58%
2l (R = CF$_3$), 81%
2m (R = CO$_2$Et), 82%
2n (R = Cl), 88%
2o (R = Br), 93%
2p (R = Me), 92%
2q (R = NHAc), 64%
2r
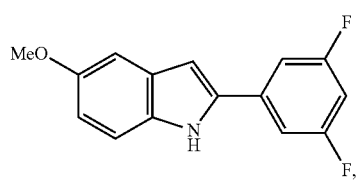
88%
2s
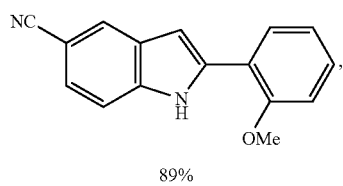
89%
2t
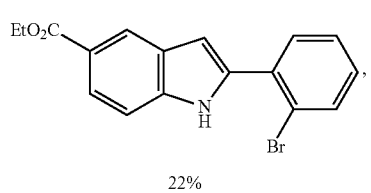
22%
2u
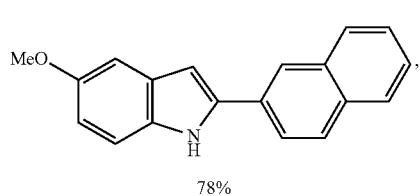
78%
2v
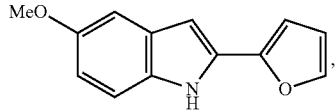
76%
2w
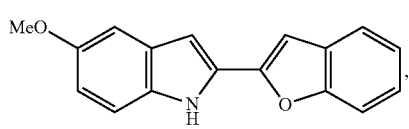
84%
2x
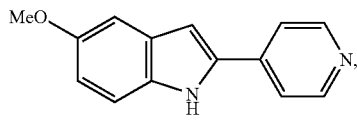
80%
2y
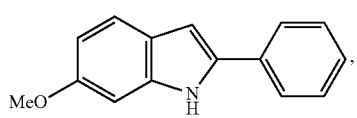
74%,[c]
2z
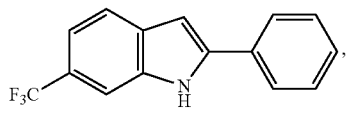
72%
2aa
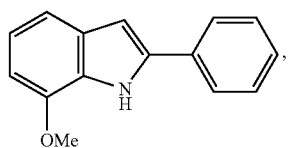
67%
2ab
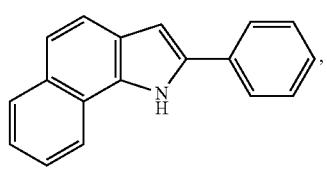
88%
2ac
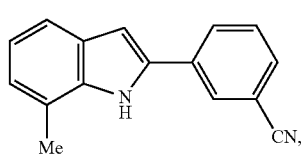
87%
2ad
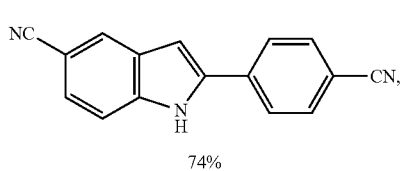
74%

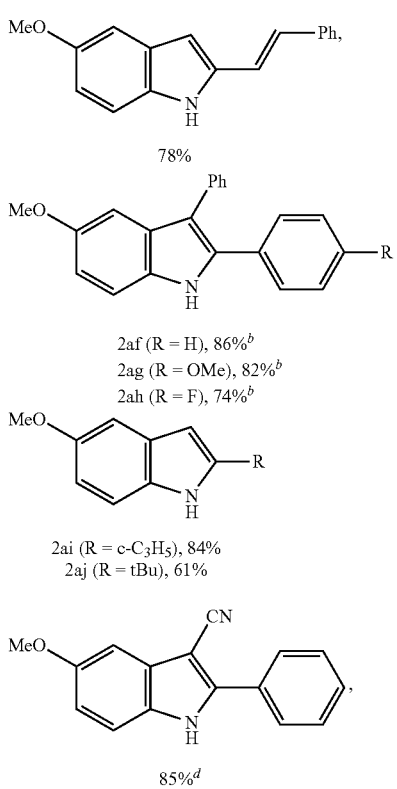

2ae, 78%

2af (R = H), 86%[b]
2ag (R = OMe), 82%[b]
2ah (R = F), 74%[b]

2ai (R = c-C$_3$H$_5$), 84%
2aj (R = tBu), 61%

2ak, 85%[d]

a NR'$_2$ is a morpholino group. b Cu(OAc)$_2$ was used as the oxidant (conditions in Table 2, entry 8). c A regioisomeric product was obtained in 7% yield. d The starting material was in the form of enamine.

An α,β-unsaturated imine underwent cyclization smoothly to give 2-alkenylindole 2ae in 78% yield. An imine derived from 2-phenylacetophenone afforded 2,3-diphenylindole 2af in 40% yield, which was accompanied by a ketone byproduct (33%) arising from benzylic oxidation. However, by using Cu(OAc)$_2$ as the oxidant, the yield of 2af was improved to 86% with a complete suppression of benzylic oxidation. Similarly, 2,3-diarylindoles 2ag and 2ah were obtained in good yields. These examples demonstrate the utility of the present cyclization for regiocontrolled synthesis of 2,3-diarylindoles, which is difficult with the Larock- and Fagnou-type annulation reactions using diarylalkynes. 2-Cyclopropyl- and 2-t-butylindoles 2ai and 2aj were also obtained in good yields from the corresponding imines, while attempts to synthesize 2-n-alkylindoles have not been successful. In addition to these examples, the present method was also applicable to an enamine derived from benzoylacetonitrile,[5] resulting in the formation of 2-phenyl-3-cyanoindole 2ak in 85% yield.

Twofold cyclization of phenylenediamine-derived diimines 1al and 1am readily provided the fused indoles 2al and 2 am, respectively, albeit in modest yields (Scheme 2'a, b). These products particularly underline the power of the present cyclization reaction, as any of conventional methods would not allow their synthesis with such great ease. The regioselectivity observed for the latter case poses an intriguing mechanistic question that cannot be answered at present. Twofold cyclization was also achieved for a diimine 1an derived from 1,3-diacetylbenzene, affording a 1,3-bis(indolyl)benzene 2an in 90% yield (Scheme 2'c). Such multifold cyclizations may serve as attractive routes to extended π-conjugated systems for potential applications in organic electronics.

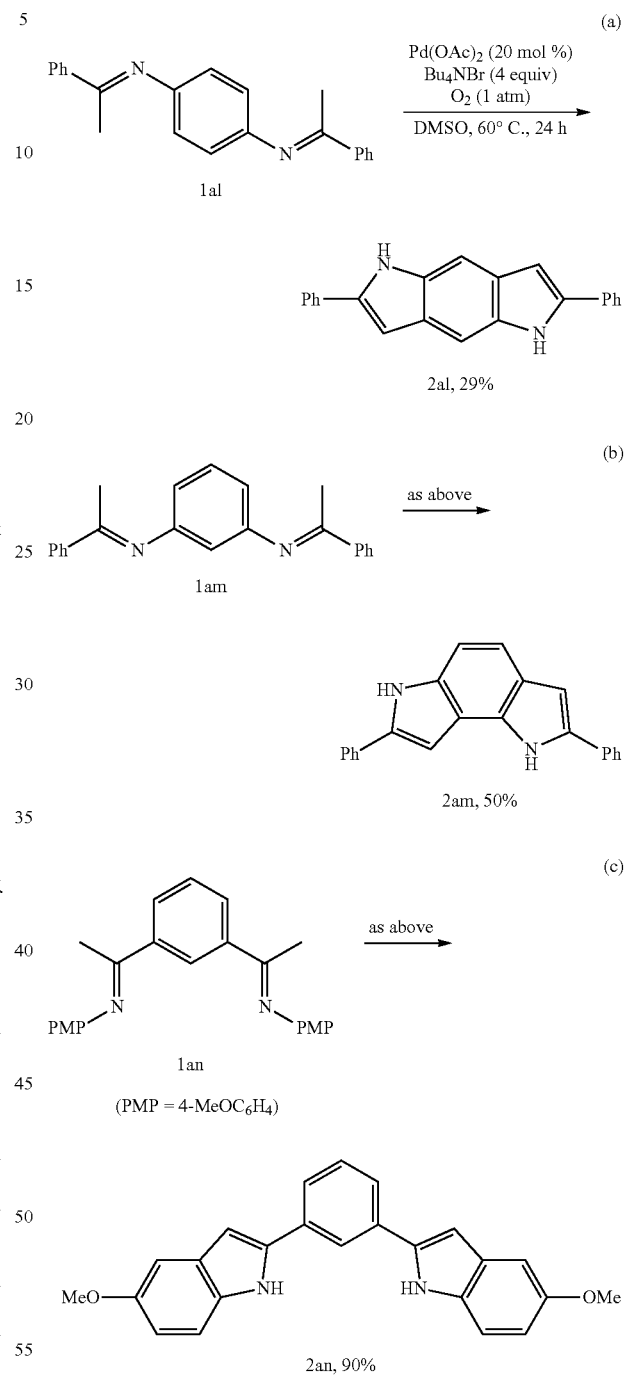

Scheme 2' Twofold Oxidative Cyclizations (excerpt of results shown in Scheme 2)

(a) 1al → 2al, 29%
Pd(OAc)$_2$ (20 mol %), Bu$_4$NBr (4 equiv), O$_2$ (1 atm), DMSO, 60° C., 24 h (b) 1am → 2am, 50% (as above)

(c) 1an (PMP = 4-MeOC$_6$H$_4$) → 2an, 90% (as above)

Feasibility of one-pot oxidative condensation of aniline and ketone is further demonstrated. Thus, with the aid of the Pd/Cu catalytic system, p-anisidine reacted with acetone and ethyl pyruvate to afford the indoles 2ao and 2ap in 55% and 41% yields, respectively (eq 2 as shown below), while no product formation was observed with the Pd/O$_2$ system. Attempts on one-pot reaction of p-anisidine and acetophenone were not successful under the standard reaction conditions, presumably because of slow formation of the imine.

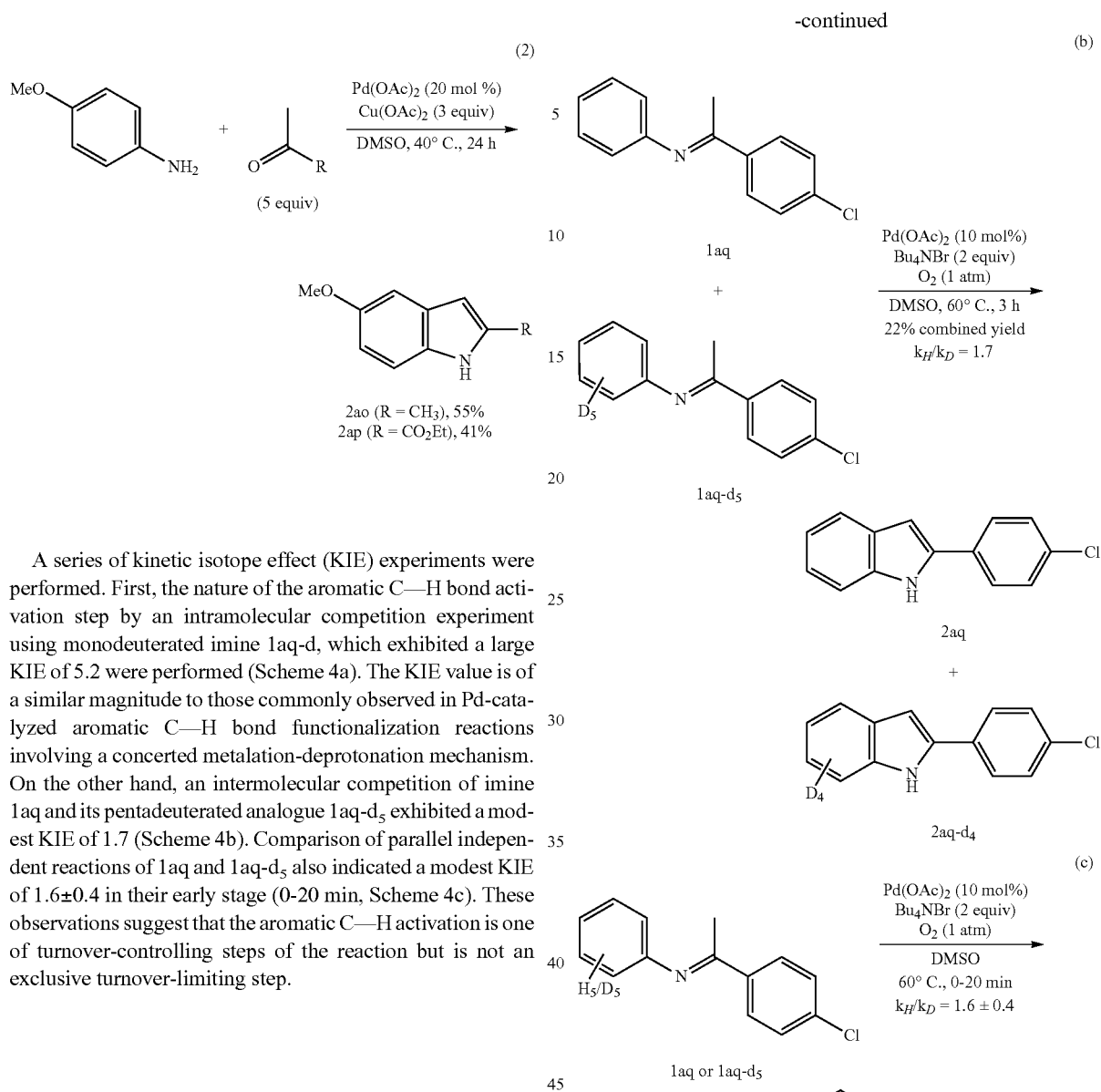

A series of kinetic isotope effect (KIE) experiments were performed. First, the nature of the aromatic C—H bond activation step by an intramolecular competition experiment using monodeuterated imine 1aq-d, which exhibited a large KIE of 5.2 were performed (Scheme 4a). The KIE value is of a similar magnitude to those commonly observed in Pd-catalyzed aromatic C—H bond functionalization reactions involving a concerted metalation-deprotonation mechanism. On the other hand, an intermolecular competition of imine 1aq and its pentadeuterated analogue 1aq-$d_5$ exhibited a modest KIE of 1.7 (Scheme 4b). Comparison of parallel independent reactions of 1aq and 1aq-$d_5$ also indicated a modest KIE of 1.6±0.4 in their early stage (0-20 min, Scheme 4c). These observations suggest that the aromatic C—H activation is one of turnover-controlling steps of the reaction but is not an exclusive turnover-limiting step.

Scheme 4. H/D Kinetic Isotope Effect Experiments

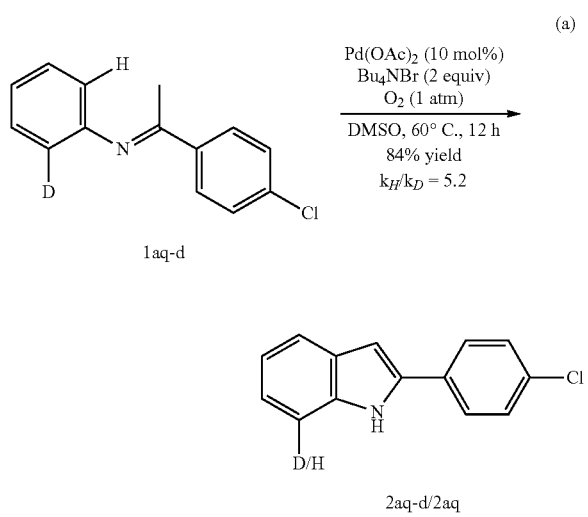

From the results obtained, and the fact that a stoichiometric amount of Pd(OAc)$_2$ promotes the reaction in the absence of oxidant (Table 2, entry 12), a possible catalytic cycle that involves a Pd(II)/Pd(0) redox process is suggested (Scheme 5a).

Enamine 1' generated via tautomerization of imine 1 would be electrophilically attacked by Pd(OAc)$_2$ (A), followed by elimination of HOAc to give an α-palladated imine B. The intermediate B would then undergo intramolecular aromatic C—H palladation to give a six-membered palladacycle C. Subsequent reductive elimination affords 3H-indole 2' and Pd(0). The former tautomerizes quickly to indole 2 while the latter is oxidized back to Pd(II) with the aid of molecular oxygen and HOAc. Note that, under the standard conditions, tetralone-derived imine 1ar underwent dehydrogenative aromatization to afford aminonaphthalene 3 presumably via β-hydride elimination of an α-palladated imine (Scheme 5b), which may indirectly support the formation of the putative C(sp³)-Pd species B in the proposed catalytic cycle. Further studies are underway to address more details of the reaction mechanism including the role of the ammonium salt.

enabling two-step assembly of substituted indoles, 2-arylindoles in particular, from readily available anilines and ketones without any non-essential prefunctionalization steps has been developed. Thus, the present method would not only serve as a practical, versatile, and atom-economical alternative to existing synthetic methods but also allow facile construction of indole skeletons that have not been easily acces-

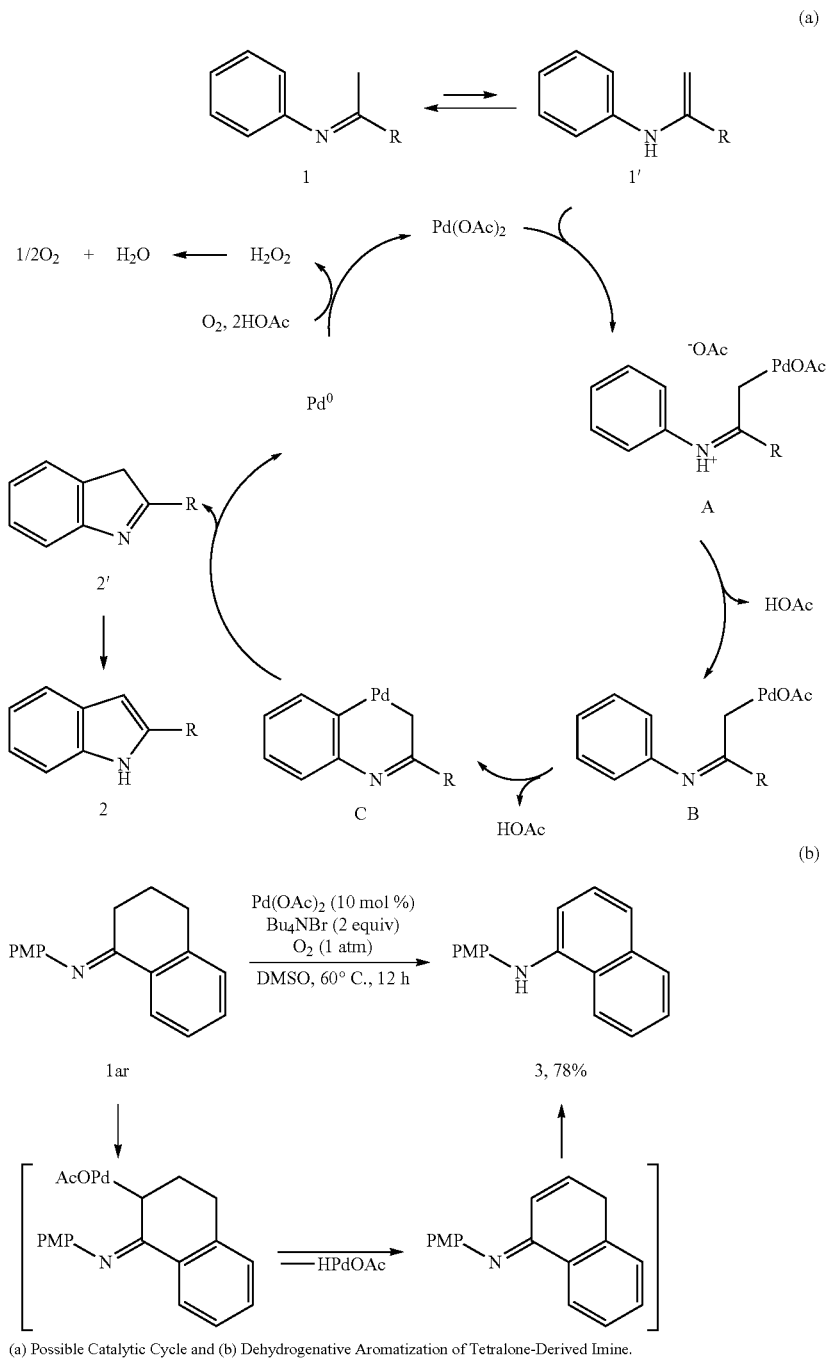

(a) Possible Catalytic Cycle and (b) Dehydrogenative Aromatization of Tetralone-Derived Imine.

In summary, a simple, mild, and scalable palladium-catalyzed aerobic oxidative cyclization reaction of N-aryl imines, sible. Further studies should lead to more robust, benign, and broadly applicable catalytic systems that could find applications in complex settings relevant to medicinal chemistry and materials science, and hence could have a significant impact on the laboratory- and industry-scale synthesis of indoles.

The invention claimed is:

1. A method for the synthesis of an indole of Formula (I) or a salt thereof,

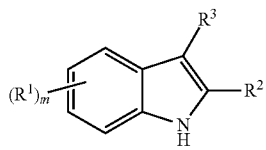
Formula (I)

the method comprising oxidizing a N-aryl imine of Formula (II)

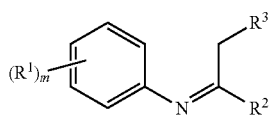
Formula (II)

in the presence of a palladium-based catalyst, an oxidant selected from the group consisting of copper (II) acetate, benzoquinone, tert-butylhydroperoxide, di-tert-butyl peroxide (tBuOOtBu), tert-butyl benzoyl peroxide (BzOOtBu), molecular oxygen ($O_2$), and air, or combinations thereof and a solvent comprising of dimethylsulfoxide, wherein the amount of oxidant is about 0.5 equivalence to about 5 equivalence of N-aryl amine;
wherein
$R^1$ at each occurrence is independently selected from the group consisting of hydrogen, optionally substituted $C_1$-$C_{20}$ alkyl, optionally substituted $C_3$-$C_{20}$ mono-, or poly-cycloalkyl, optionally substituted 2-20-membered heteroalkyl, optionally substituted 3-20-membered mono-, or poly-heterocycloalkyl, halogen, and —OR; wherein R is optionally substituted $C_1$-$C_{20}$ alkyl; wherein $R^2$ is selected from the group consisting of optionally substituted $C_2$-$C_{20}$ alkenyl, optionally substituted 2-20-membered heteroalkenyl, optionally substituted monocyclic, condensed polycyclic or bridged polycyclic $C_5$-$C_{20}$ aryl, and optionally substituted 5-20-membered monocyclic, condensed polycyclic or bridged polycyclic heteroaryl; wherein $R^3$ is selected from the group consisting of hydrogen, $C_1$-$C_{20}$ alkyl, $C_2$-$C_{20}$ alkenyl; monocyclic, condensed polycyclic or bridged polycyclic $C_5$-$C_{20}$ aryl; $C_3$-$C_{20}$ mono-, or poly-cycloalkyl; and $C_3$-$C_{20}$ mono-, or poly-cycloalkenyl;
m is 0, 1, 2, 3, or 4;
wherein
$R^1$ at each occurrence is positioned on the phenyl ring in 3-, 4-, 5-, or 6-position with respect to the bond linking the phenyl to the —N—H group according to Formula (I) or the —N═C group according to Formula (II).

2. The method according to claim 1, wherein $R^1$ at each occurrence is independently selected from the group consisting of hydrogen, alkyl, —O-alkyl, and halogen.

3. The method according to claim 1, wherein $R^1$ at each occurrence is independently selected from the group consisting of —H, —OCH$_3$, and —Cl.

4. The method according to claim 1, wherein $R^1$ is positioned on the phenyl ring in 4-position with respect to the bond linking the phenyl to the —N—H group according to Formula (I) or the —N═C group according to Formula (II).

5. The method according to claim 1, wherein $R^2$ is

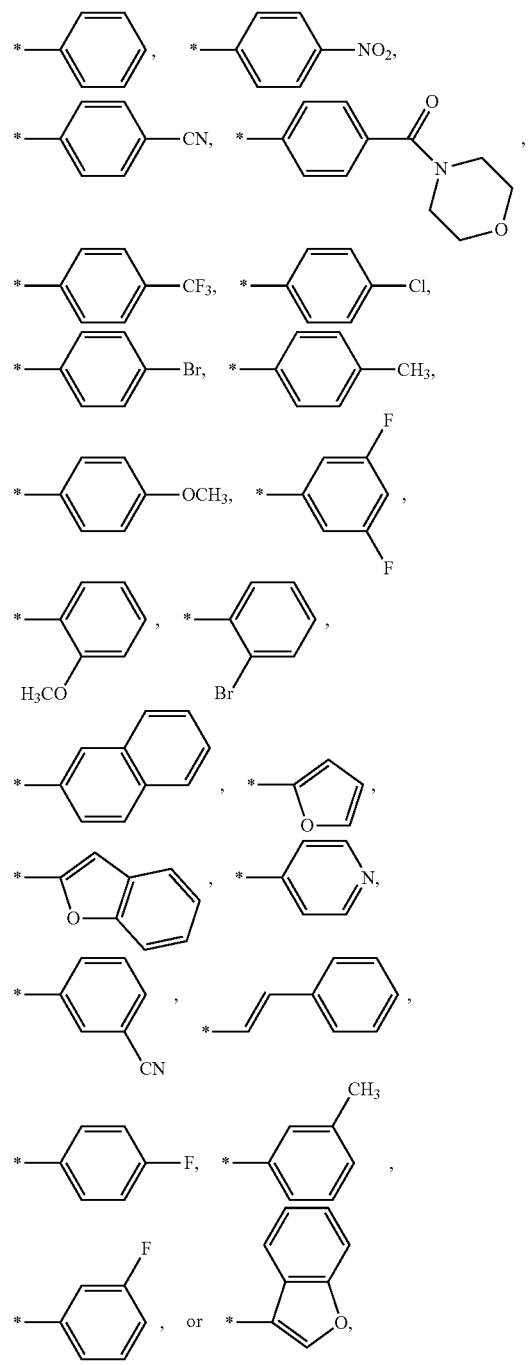

wherein * denotes the point in which $R^2$ is connected to the parent molecular moiety.

6. The method according to claim 1, wherein $R^3$ is hydrogen or phenyl.

7. The method according to claim 1, wherein the indole is 2-aryl indole, 2-alkenyl indole, 2,3-diaryl indole, 2-aryl-3-alkenyl indole, 2-alkenyl-3-aryl indole, 2,3-dialkenyl indole, 2-aryl-3-alkyl indole, or 2-alkenyl-3-alkyl indole.

8. The method according to claim 1, wherein the indole is
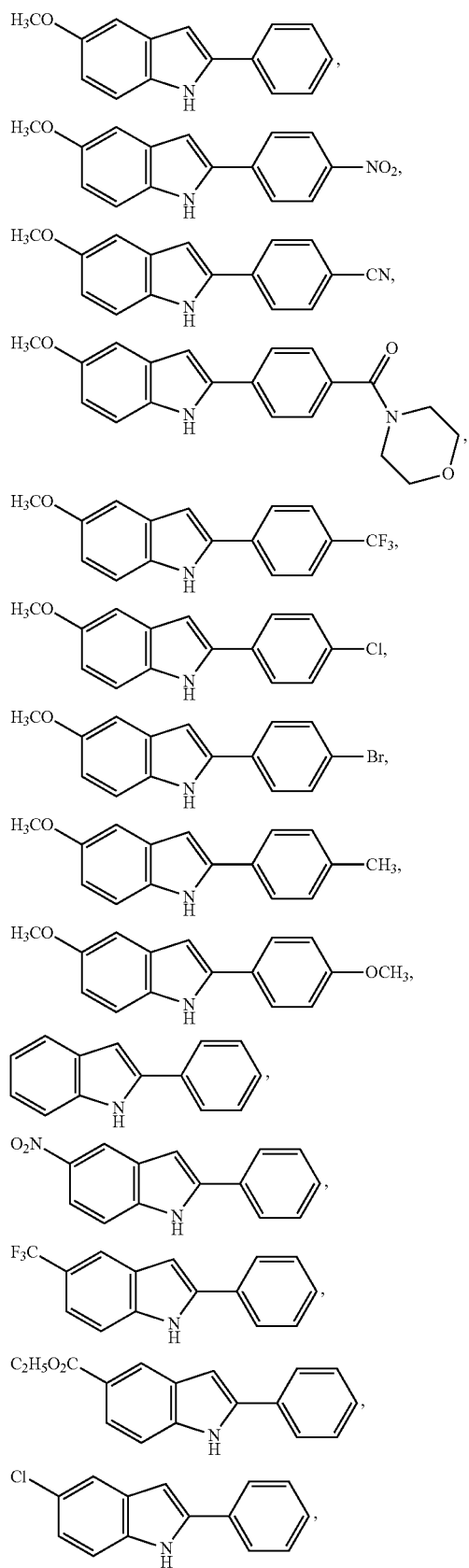
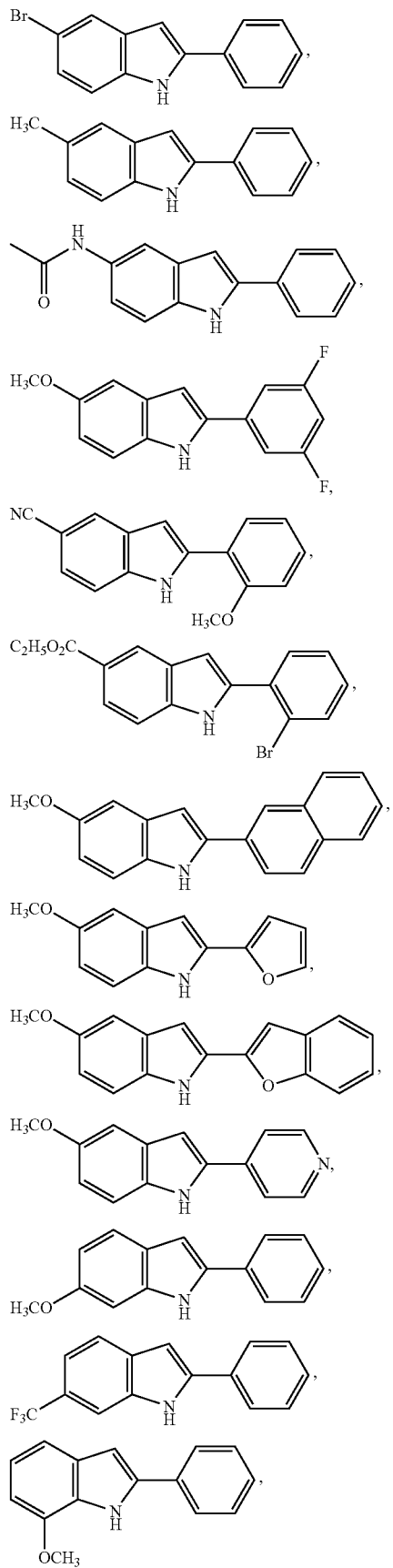

-continued

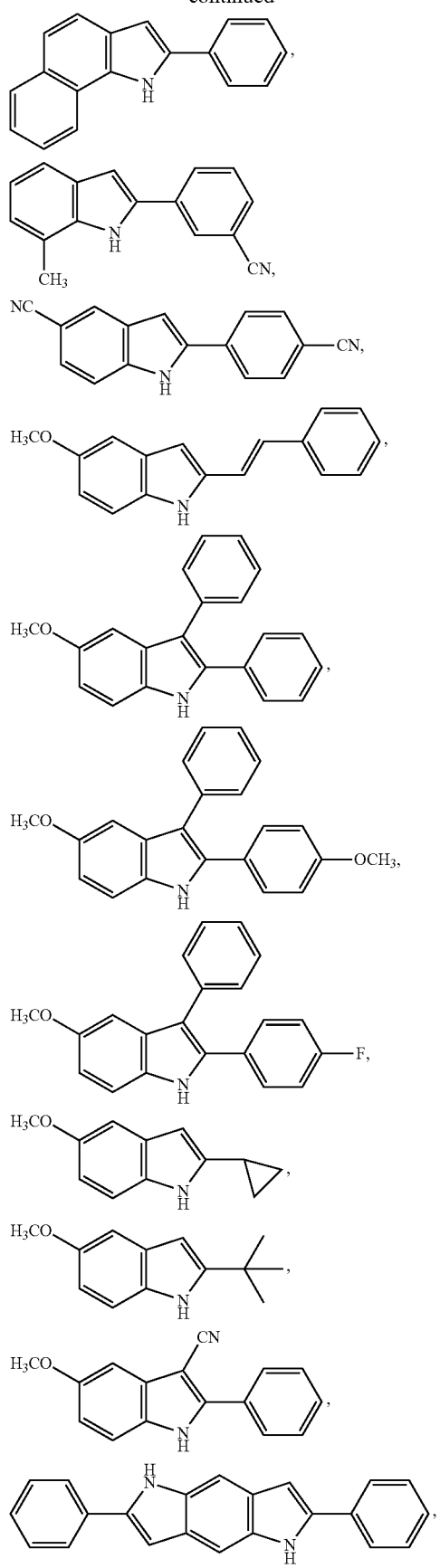

-continued

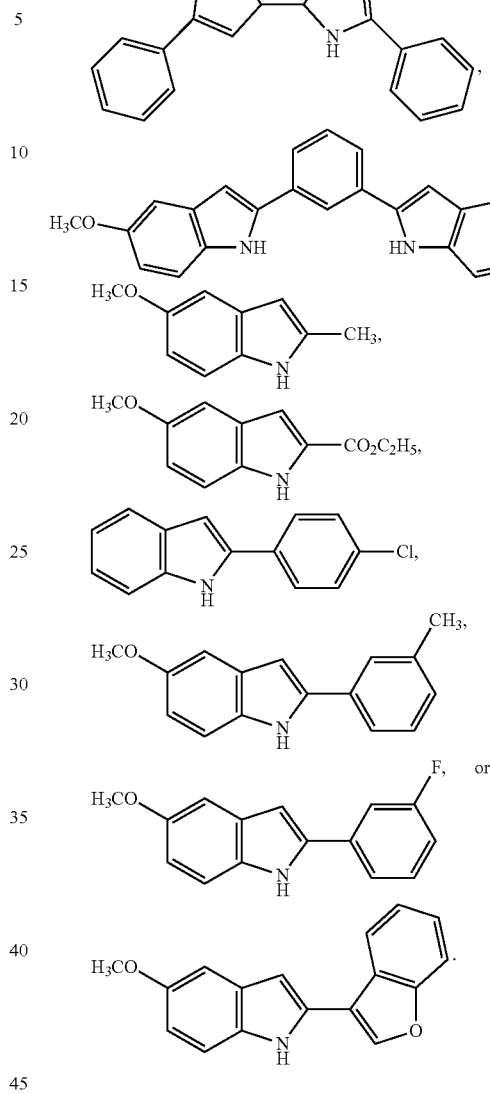

9. The method according to claim 1, wherein the palladium-based catalyst is selected from the group consisting of palladium metal, palladium (II) acetate, sodium palladium (II) chloride, palladium (II) acetylacetonate, palladium(II) trifluoroacetate, palladium hydroxide, palladium(II) bromide, palladium (II) chloride, palladium(II) cyanide, palladium(II) hexafluoroacetylacetonate, palladium(II) iodide, palladium(II) nitrate dehydrate, palladium(II) nitrate hydrate, palladium(II) oxide, palladium (II) propionate, palladium (II) sulfate, and palladium (II) sulfide, or mixtures thereof.

10. The method according to claim 9, wherein the palladium-based catalyst comprises of palladium (II) acetate.

11. The method according to claim 1, wherein the amount of palladium-based catalyst is in the range of about 0.1 mol % to about 20 mol %, with respect to the amount of N-aryl imine.

12. The method according to claim 1, wherein the oxidant comprises of copper (II) acetate.

13. The method according to claim 1, wherein the oxidant comprises of molecular oxygen ($O_2$).

14. The method according to claim 1, wherein the amount of oxidant is about 2 equivalence to about 3 equivalence, of the amount of N-aryl imine.

15. The method according to claim 1, further comprising reacting in the presence of an additive, wherein the additive comprises a quaternary ammonium salt of Formula (III)

$$(R_4)_nN-X \qquad \text{Formula (III)}$$

wherein
- $R_4$ at each occurrence is independently selected from $C_1$-$C_{20}$ alkyl;
- n is 1, 2, 3 or 4; and
- X is selected from the group consisting of a halogen and —$OCOCH_3$.

16. The method according to claim 15, wherein the additive is selected from the group consisting of $Bu_4NBr$, $Bu_4NCl$, $Bu_4NI$, and $Bu_4NOCOCH_3$.

17. The method according to claim 15, wherein the amount of additive is about 1 equivalence to about 3 equivalence of the amount of N-aryl imine.

18. The method according to claim 15, wherein the additive comprises a ligand for the palladium-based catalyst, wherein the ligand is selected from the group consisting of pyridine, 2,2'-bipyridine, 1,10-phenanthroline, $PPh_3$, dppm, dppe, dppp, dcpe, $P(c\text{-hex})_3$, $P(tBu)_3$, $P(C_6F_5)_3$, and $P(2,4,6\text{-}Me_3C_6H_2)_3$, or mixtures thereof.

19. The method according to claim 18, wherein the amount of ligand is about 1 equivalence to about 2 equivalence of the amount of palladium present in the palladium-based catalyst.

20. The method according to claim 1, wherein the method is carried out at a temperature in the range of about 0° C. to about 150° C.

* * * * *